US006919322B2

(12) United States Patent
Bookser et al.

(10) Patent No.: US 6,919,322 B2
(45) Date of Patent: Jul. 19, 2005

(54) PHENYL PHOSPHONATE FRUCTOSE-1,6-BISPHOSPHATASE INHIBITORS

(75) Inventors: Brett C. Bookser, San Diego, CA (US); Qun Dang, San Diego, CA (US); K. Raja Reddy, San Diego, CA (US)

(73) Assignee: Metabasis Therapeutics, Inc., San Diego, CA (US)

( * ) Notice: Subject to any disclaimer, the term of this patent is extended or adjusted under 35 U.S.C. 154(b) by 0 days.

(21) Appl. No.: 09/801,933

(22) Filed: Mar. 7, 2001

(65) Prior Publication Data

US 2002/0040014 A1 Apr. 4, 2002

Related U.S. Application Data

(60) Provisional application No. 60/187,750, filed on Mar. 8, 2000.

(51) Int. Cl.[7] .............................. C07F 9/38; C07F 9/547; C07F 9/6587; A61K 31/662; A61K 31/675
(52) U.S. Cl. .............................. 514/85; 514/86; 514/87; 514/89; 514/92; 514/94; 514/95; 514/99; 514/110; 514/114; 514/118; 514/120; 514/124; 514/125; 514/134; 514/135; 514/137; 514/138; 514/141; 544/243; 544/337; 546/21; 548/111; 549/6; 549/216; 558/81; 558/83; 562/8; 562/11; 562/15; 562/16; 562/23; 562/24; 562/25; 564/13
(58) Field of Search ................................. 544/243, 337; 546/21; 548/111; 549/6, 216; 558/80, 81, 83, 178, 179, 215, 216, 190, 193, 194, 195, 199; 564/13, 14, 12, 8, 10, 15

(56) References Cited

U.S. PATENT DOCUMENTS

| | | | |
|---|---|---|---|
| 3,524,846 A | | 8/1970 | Moffat et al. |
| 4,640,701 A | * | 2/1987 | Diel et al. ...................... 71/86 |
| 4,968,790 A | | 11/1990 | DeVries et al. |
| 5,045,557 A | * | 9/1991 | Buss et al. ................... 514/397 |
| 5,157,027 A | | 10/1992 | Biller et al. |
| 5,278,153 A | * | 1/1994 | Biller ......................... 514/107 |
| 5,658,889 A | | 8/1997 | Gruber et al. |
| 6,054,587 A | | 4/2000 | Reddy et al. |
| 6,110,903 A | | 8/2000 | Kasibhatla et al. |
| 6,284,748 B1 | | 9/2001 | Dang et al. |
| 6,294,672 B1 | | 9/2001 | Reddy et al. |
| 6,312,662 B1 | | 11/2001 | Erion et al. |
| 6,399,782 B1 | | 6/2002 | Kasibhatla et al. |
| 6,489,476 B1 | | 12/2002 | Dang et al. |

FOREIGN PATENT DOCUMENTS

| | | |
|---|---|---|
| EP | 0 427 799 | 11/1994 |
| EP | 0 632 048 | 1/1995 |
| WO | WO 90/08155 | 7/1990 |
| WO | WO 90/10636 | 9/1990 |
| WO | WO 91/19721 | 12/1991 |
| WO | WO 95/07920 | 3/1995 |
| WO | WO 98/39342 | 9/1998 |
| WO | WO 98/39343 | 9/1998 |
| WO | WO 98/39344 | 9/1998 |
| WO | WO 99/47549 A1 | 9/1999 |
| WO | WO 00/14095 | 3/2000 |
| WO | WO 00/38666 | 7/2000 |
| WO | WO 00/52015 | 9/2000 |
| WO | WO 2001089457 A2 * | 11/2001 |

OTHER PUBLICATIONS

Shan, Daxian, et al, J. Pharmaceutical Sci., 1997, 86, pp. 765–767.*
Hawley, Gessner, "The Condensed Chemical Dictonary", 1977, Van Nostrand, New York, p. 25.*
Stedman's (Medical Dictionary, 26th Ed.), Williams & Wilkins, Baltimore, 1995, p. 733.*
Wolff, Manfred E. "Burger's Medicinal Chemistry, 5ed, Part I", John Wiley & Sons, 1995, pp. 975–977.*
Banker, G.S. et al, "Modern Pharmaceutics, 3ed.", Marcel Dekker, New York, 1996, p. 596.*
Sanchez, J.P. et al, J. Med. Chem, vol. 35, 1992, pp. 1764–1773.*
Bundgaard, H. et al, J. Med. Chem., vol. 30, 1987, pp. 454–455.*
Krecmerova, Marcela; Holy, Antonin, Collection of Czechoslovak Chemical Communications, 60(4), 659–69 (English) 1995.*
Huang, Weisheng; Yuan, Chengye Synthesis (4), 511–13 (English) 1996.*
Shaw, J.P et al, Pharm. Res., vol. 14, 1997, 1824–1829.*
Alexander, et al., "Preparation or 9–(2–Phosphonomethoxyethyl)adenine Esters as Potential Prodrugs," *Collect. Czech. Chem. Commun.*, 59:1853–1869 (1994).
Athmani, et al., "Azoles. Part 9.[1] Synthesis of Derivatives of Thieno[2,3–d]thiazole, 4H–Pyrrolo–[2.3–d]thiazole, 2H–Pyrazolo[3,4–d]thiazole from Thiazolidine–2,4–dione." *J. Chem. Soc., Perkin Trans. 1*, 973–977 (1992).
Barluenga, et al., "Substituted Organolithium Compounds. New Reagents for Synthesis," *J. Org. Chem.*, 44(26):4798–4801 (1979).

(Continued)

*Primary Examiner*—Thomas C. McKenzie
(74) *Attorney, Agent, or Firm*—Paul, Hastings, Janofsky & Walker LLP

(57) ABSTRACT

Novel FBPase inhibitors of the formula I

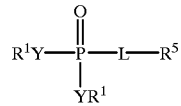

are useful in the treatment of diabetes and other conditions associated with elevated blood glucose.

56 Claims, No Drawings

OTHER PUBLICATIONS

Benzaria, et al. "Synthesis in vitro Antiviral Evaluation, and Stability Studies of Bis(S–acyl–2–thioethyl) Ester Derivatives of 9–[2–(Phosphonomethoxy)ethyl]adenine (PMEA) as Potential PMEA Prodrugs with improved Oral Bioavailability," *J. Med. Chem.*, 39:4958–4965 (1996).

Bhongle, et al., "Expedient and High–Yield Synthesis of Alkylphosphonyl Dichlorides Under Mild, Neutral Conditions: Reaction of Bis(Trimethylsilyl)Alkyl Phosphonates with Oxalyl Chloride/Dimethylformamide," *Synth. Commun.*, 17(9):1071–1076 (1987).

Brinton, et al., "Characterization of Murine Caraparu *Bunyavirus* Liver Infection and Immunomodulator–Mediated Antiviral Protection," *Antiviral Res.*, 20:155–171 (1992).

Campagne, et al., "Synthesis of Mixed Phosphonate Diester Analogues of Dipeptides using BOP or PyBOP Reagents," *Tetrahedron Lett.*, 34:6743–6744 (1993).

Campbell, et al., "The Synthesis cf Phosphonate Esters, an Extension of the Mitsunobu Reaction," *J. Org. Chem.*, 57:6331–6335 (1992).

Canas, et al., "Regioselective Ring Opening of Chiral Epoxyalcohols by Primary Amines," *Tetrahedron Lett.*, 32:6931–6934 (1991).

Casara, et al., "Synthesis of Acid Stable 5'–O–Fluoromethyl Phosphonates of Nucleosides. Evaluation as Inhibitors of Reverse Transcriptase," *Bioorg. Med. Chem. Lett.*, 2:145–148 (1992).

Claus, et al., "Mechanism of the Acute Action of Insulin On Hepatic Gluconeogenesis," *Mechanisms of Insulin Action*, pp. 305–321, Elsevier Science, (1992).

Commercon, et al., "Diastereoselective Chlorocyclofunctionalization of N–allylic Trichloroacetamides: Synthesis of an Analogue and Potential Precurser of RP49532," *Tetrahedron Lett.*, 31:3871–3874 (1990).

Corey, et al., "Enantioselective and Practical Synthesis of R– and S–Fluoxetines," *Tetrahedron Lett.*, 30:5207–5210 (1989).

Curran, Thermolysis of Bis[2—[(trimethylsilyl)oxy] prop–2–yI] fuxoran (TOP–furoxan). The First Practical Method for Intermolecular Cycloaddition of an in Situ Nitrile Oxide with 1,2–Di and Trisubstituted Olefins, *J. Am Chem. Soc.*, 107:6023–6028 (1985).

De Lombaert, et al., "N–Phosphonomethyl Dipeptides and Their Phosphonate Prodrugs, a New Generation of Neutral Endopeptidase (NEP, EC 3.4.24.11). Inhibitors," *J. Med. Chem.*, 37:498–511 (1994).

Dickson, et al., "Orally Active Squalene Synthase Inhibitors: Bis(acyloxy) Prodrugs of the α–Phosphonosulfonic Acid Moiety," *J. Med. Chem.*, 39:661–664 (1996).

Egron, et al., "Synthesis and Anti–HIV Activity of Some S–Acyl–2–Thioethyl (SATE) Phosphoramidate Derivatives of 3'–Azido–2',3'–Dideoxythymidine," *Nucleosides and Nucleotides*, 18:981–982 (1999).

Elhaddadi, et al., "A Convenient Synthesis of Alkyl and Dialkyl 1–Benzyloxyamino Alkyl Phosphonates and Phosphinates," *Phosphorus, Sulfur and Silicon*, 54(1–4):143–150 (1990).

Farquhar, et al., "Biologically Reversible Phosphate–Protective Groups," *J. Pharm. Sci.*, 72:324–325 (1983).

Ferres, H., "Pro–Drugs of β–Lactam Antibiotics," *Drugs of Today*, 19:499–538 (1983).

Folsom, et al., "Relation of Carotid artery Wall Thickness to Diabetes Mellitus, Fasting Glucose and Insulin, Body Size, and Physical Activity," *Stroke*, 25:66–73 (1994).

Freed, et al., "Evidence for Acyloxymethyl Esters of Pyrimidine 5'–Deoxyribonucleotides as Extracellular Sources of Active 5'–Deoxyribonucleotides in Cultured Cells," *Biochem. Pharmacol.*, 38:3193–3198 (1989).

Haddad, et al., "Stereocontrolled Reductive Amination of 3–Hydroxy Ketones," *Tetrahedron Lett.*, 38:5981–5984 (1997).

Hoffmann, M., "A Simple, Efficient Synthesis of Dibenzyl and Di–p–nitroben 1–Hydroxyalkanephosphonates," *Synthesis*, pp. 62–64 (1988).

Hori, et al., "Palladium (II)–Catalyzed Asymmetric 1,3–Dipolar Cycloaddition of Nitrones to 3–Alkenoyl–1, 3–oxazodilin2–ones," *J. Org. Chem.*, 64:5017–5023 (1999).

Howard, G. et al., "Insulin Sensitivity and Atherosclerosis," *Circulation*, 93:1809–1817 (1996).

Iyer, et al., "Synthesis of Acyloxyalkyl Acylphosphonates as Potential Prodrugs of the Antiviral, Trisodium Phosphonoformate (Foscarnet Sodium)," *Tetrahedron Lett.*, 30:7141–7144 (1989).

Khamnei, et al., "Neighboring Group Catalysis in the Design of Nucleotide Prodrugs," *J. Med. Chem.*, 39:4109–4115 (1996).

Colen, "Complete Regio– and Stereospecificity in the Lewis Acid Catalyzed Diels–Alder Reactions of (Z) 2–Methoxy–1(phenolthio)–1,3–butadienes. Conversion of the CS Configuration of an Adduct to the CC Configuration at the Allylic Position by a [2,3] Sigmatropic Rearrangement," *J. Org. Chem.* 47:4005–4008 (1982).

Martin, et al., "Synthesis and Antiviral Activity of Various Esters of 9–[(1,3–Dihydroxy–2–propoxy)methyl]guanine," *J. Pharm.Sci.*, 76(2):180–184 (1987).

Maryanoff, "Stereoselective Synthesis and Biological Activity of β– and α–D–Arabinose 1,5–Diphosphate: Analogues of a Potent Metabolic Regulator," *J. Am. Chem. Soc.*, 106:7851–7853 (1984).

McGuigan, et al., "Synthesis and Anti–HIV Activity of Some Haloalkyl Phosphoramidate Derivatives of 3'–Azido–3'–Deoxythymidine (AZT): Potent Activity of the Trichloroethyl Methoxyalaninyl Compound," *Antiviral Research*, 15, 255–263 (1991).

Meier, C., et al., Cyclic Saligenyl Phosphotriesters of 2',3'–DIdeoxy–2',3'–didehydrothymidine (d4T)—A New Pro–Nucleotide Approach, *Bioorg. Med. Chem. Lett.*, 7:99–104 (1997).

Mitchell, et al., "Bioreversible Protection for the Phospho Group: Bioactivation of the Di(4–acyloxybenzyl) and Mono(4–acyloxybenzyl) Phosphoesters of Methylphosphonate and Phosphonoacetate,". *J. Chem. Soc., Perkin Trans. 1*, 38:2345–2353 (1992).

Mitsunobo, et al., "The Use of Diethyl Azodicarboxylate and Triphenylphosphine in Synthesis and Transformation of Natural Products," *Synthesis*, pp. 1–28 (1981).

Mukaiyama, et al., "Synthesis of Oligothymidylates and Nucleoside Cyclic Phosphates by Oxidation–Reduction Condensation," *J. Am. Chem. Soc.*, 94:8528–8532 (1972).

Nishimura, et al., "Orally Active 1–(Cyclohexyloxycarbonyloxy)Alkyl Ester Prodrugs of Cefotiam," *J. Antibiot.*, 40(1):81 –90 (1987).

Patois, et al., "Easy Preparation of Alkylphosphonyl Dichlorides," *Bull. Soc. Chim. Fr.*, 130:485–487 (1993).

Pilkis, et al., "Hormonal Regulation of Hepatic Gluconeogenisis and Glycolysis," *Ann. Rev. Biochem.*, 57:755–783 (1988).

Posner, et al., "3–Bromo–2–Pyrone: An Easily Prepared Chameleon Diene And A Synthetic Equivalent Of 2–Pyrone in Thermal Diels–Alder Cycloadditions," *Tetrahedron Lett.*, 39:5295–5298 (1991).

Puech, et al., "Intracellular Delivery of Nucleoside Monophosphates Through a Reductase–Mediated Activation Process," *Antiviral Res.*, 22:155–174 (1993).

Quast, et al., "Herstelling von Methylphosphonsaure–diclorid," *Synthesis*, pp. 461–538 (1974).

Rao, et al., "Studies Directed Towards The Synthesis of Immunosuppressive Agent FK–506: Synthesis of the Entire Top–Half," *Tetrahedron Lett.*, 32:547–550 (1991).

Regen, et al., "Sensitivity of Pathway Rate to Activities of Substrate–Cycle Enzymes: Application to Gluconeogenesis and Glycolysis," *J. Theor. Biol.*, 111:635–658 (1984).

Serafinowska, et al., "Synthesis and In Vivo Evaluation of Prodrugs of 9–[2–(Phosphonomethoxy)ethoxy]adenine," *J. Med. Chem.*, 38:1372–1379 (1995).

Shaw, et al., "Metabolism and Pharmacokinetics of Novel Oral Prodrugs of 9–[(R)–2–(phosphonomethoxy)propyl]adenine (PMPA) in Dogs," *Pharm. Res.*, 14:(12) 1824–1829 (1997).

Shulman, et al., "Pathways of Glycogen Repletion," *Physiol. Rev.*, 72(4):1019–1035 (1992).

Siddiqui, et al., "The Presence of Substituents on the Aryl Moiety of the Aryl Phosphoramidate Derivative of d4T Enhances Anti–HIV Efficacy In Cell Culture: A Structure Activity Relationship," *J. Med. Chem.*, 42:393–399 (1999).

Srivastva, et al., "Bioreversible Phosphate Protective Groups: Synthesis and Stability of Model Acyloxymethyl Phosphates," *Bioorg. Chem.*, 12:118–129 (1984).

Starrett, et al., "Synthesis, Oral Bioavailability Determination, and in Vitro Evaluation of Prodrugs of the Antiviral Agent 9–[2–(Phosphonomethoxy)ethyl]adenine (PMEA)," *J. Med. Chem.*, 37:1857–1864 (1994).

Still, et al., "Direct Synthesis of Z–Unsaturated Esters. A Useful Modification of the Homer–Emmons Olefination," *Tetrahedron Lett.*, 24:4405–4408 (1983).

Stowell, et al., "The Mild Preparaton of Synthetically Useful Phosphonic Dichlorides: Application to the Synthesis of Cyclic Phosphonic Diesters and Diamides," *Tetrahedren Lett.*, 31:3261–3262 (1990).

U.K. Prospective Diabetes Group, U.K. Prospective Diabetes Study 16. "Overview of 6 Years' Therapy of Type II Diabetes: A Progressive Disease," *Diabetes*, 44:1249–1258 (1995).

* cited by examiner

PHENYL PHOSPHONATE FRUCTOSE-1,6-BISPHOSPHATASE INHIBITORS

RELATED APPLICATION

The present application claims the benefit of priority to U.S. Provisional Application No. 60/187,750, filed on Mar. 8, 2000 and is incorporated by reference in its entirety.

FIELD OF THE INVENTION

This invention relates to novel aryl containing compounds that possess a phosphonate group that are inhibitors of Fructose-1,6-bisphosphatase. The invention also relates to the preparation and use of these compounds in the treatment of diabetes, and other diseases where the inhibition of gluconeogenesis, control of blood glucose levels, reduction in glycogen storage, or reduction in insulin levels is beneficial.

BACKGROUND AND INTRODUCTION TO THE INVENTION

The following description of the background of the invention is provided to aid in understanding the invention, but is not admitted to be, or to describe, prior art to the invention. All cited publications are incorporated by reference herein in their entirety.

Diabetes mellitus (or diabetes) is one of the most prevalent diseases in the world today. Diabetic patients have been divided into two classes, namely type I or insulin-dependent diabetes mellitus and type II or non-insulin dependent diabetes mellitus (NIDDM). NIDDM accounts for approximately 90% of all diabetics and is estimated to affect 12–14 million adults in the U.S. alone (6.6% of the population). NIDDM is characterized by both fasting hyperglycemia and exaggerated postprandial increases in plasma glucose levels. NIDDM is associated with a variety of long-term complications, including microvascular diseases such as retinopathy, nephropathy and neuropathy, and macrovascular diseases such as coronary heart disease. Numerous studies in animal models demonstrate a causal relationship between long term hyperglycemia and complications. Results from the Diabetes Control and Complications Trial (DCCT) and the Stockholm Prospective Study demonstrate this relationship for the first time in man by showing that insulin-dependent diabetics with tighter glycemic control are at substantially lower risk for the development and progression of these complications. Tighter control is also expected to benefit NIDDM patients.

Current therapies used to treat NIDDM patients entail both controlling lifestyle risk factors and pharmaceutical intervention. First-line therapy for NIDDM is typically a tightly-controlled regimen of diet and exercise since an overwhelming number of NIDDM patients are overweight or obese (67%) and since weight loss can improve insulin secretion, insulin sensitivity and lead to normoglycemia. Normalization of blood glucose occurs in less than 30% of these patients due to poor compliance and poor response. Patients with hyperglycemia not controlled by diet alone are subsequently treated with oral hypoglycemics or insulin. Until recently, the sulfonylureas were the only class of oral hypoglycemic agents available for NIDDM. Treatment with sulfonylureas leads to effective blood glucose lowering in only 70% of patients and only 40% after 10 years of therapy. Patients that fail to respond to diet and sulfonylureas are subsequently treated with daily insulin injections to gain adequate glycemic control.

Although the sulfonylureas represent a major therapy for NIDDM patients, four factors limit their overall success. First, as mentioned above, a large segment of the NIDDM population do not respond adequately to sulfonylurea therapy (i.e. primary failures) or become resistant (i.e. secondary failures). This is particularly true in NIDDM patients with advanced NIDDM since these patients have severely impaired insulin secretion. Second, sulfonylurea therapy is associated with an increased risk of severe hypoglycemic episodes. Third, chronic hyperinsulinemia has been associated with increased cardiovascular disease although this relationship is considered controversial and unproven. Last, sulfonylureas are associated with weight gain, which leads to worsening of peripheral insulin sensitivity and thereby can accelerate the progression of the disease.

Results from the U.K. Diabetes Prospective Study also showed that patients undergoing maximal therapy of a sulfonylurea, metformin, or a combination of the two, were unable to maintain normal fasting glycemia over the six year period of the study. U.K. Prospective Diabetes Study 16. *Diabetes*, 44:1249–158 (1995). These results further illustrate the great need for alternative therapies.

Gluconeogenesis from pyruvate and other 3-carbon precursors is a highly regulated biosynthetic pathway requiring eleven enzymes. Seven enzymes catalyze reversible reactions and are common to both gluconeogenesis and glycolysis. Four enzymes catalyze reactions unique to gluconeogenesis, namely pyruvate carboxylase, phosphoenolpyruvate carboxykinase, fructose-1,6-bisphosphatase and glucose-6-phosphatase. Overall flux through the pathway is controlled by the specific activities of these enzymes, the enzymes that catalyzed the corresponding steps in the glycolytic direction, and by substrate availability. Dietary factors (glucose, fat) and hormones (insulin, glucagon, glucocorticoids, epinephrine) coordinatively regulate enzyme activities in the gluconeogenesis and glycolysis pathways through gene expression and post-translational mechanisms.

Of the four enzymes specific to gluconeogenesis, fructose-1,6-bisphosphatase (hereinafter "FBPase") is the most suitable target for a gluconeogenesis inhibitor based on efficacy and safety considerations. Studies indicate that nature uses the FBPase/PFK cycle as a major control point (metabolic switch) responsible for determining whether metabolic flux proceeds in the direction of glycolysis or gluconeogenesis. Claus, et al., *Mechanisms of Insulin Action*, Belfrage, P. editor, pp.305–321, Elsevier Science 1992; Regen, et al. *J. Theor. Biol.*, 111:635–658 (1984); Pilkis, et al. *Annu. Rev. Biochem*, 57:755–783 (1988). FBPase is inhibited by fructose-2,6-bisphosphate in the cell. Fructose-2,6-bisphosphate binds to the substrate site of the enzyme. AMP binds to an allosteric site on the enzyme.

Synthetic inhibitors of FBPase have also been reported. Maryanoff reported that fructose-2,6-bisphosphate analogs inhibit FBPase by binding to the substrate site. *J. Am. Chem. Soc.*, 106:7851–7853 (1984); U.S. Pat. No. 4,968,790. These compounds, however, were relatively weak and did not inhibit glucose production in hepatocytes, presumably due to poor cell penetration.

Gruber reported that some nucleosides can lower blood glucose in the whole animal through inhibition of FBPase. These compounds exert their activity by first undergoing phosphorylation to the corresponding monophosphate. EP 0 427 799 B1.

Gruber et al. U.S. Pat. No. 5,658,889 described the use of inhibitors of the AMP site of FBPase to treat diabetes. WO 98/39344, WO 98/39343, WO 98/39342 and WO 00/14095 describe specific inhibitors of FBPase to treat diabetes.

SUMMARY OF THE INVENTION

The present invention is directed towards novel aryl compounds containing a phosphonate or phosphoramidate group and are potent FBPase inhibitors. In another aspect, the present invention is directed to the preparation of this type of compound and to the in vitro and in vivo FBPase inhibitory activity of these compounds. Another aspect of the present invention is directed to the clinical use of these FBPase inhibitors as a method of treatment or prevention of diseases responsive to inhibition of gluconeogenesis and in diseases responsive to lowered blood glucose levels.

The compounds are also useful in treating or preventing glycogen storage diseases and diseases such as cardiovascular diseases including atherosclerosis, myocardial ischemic injury, and diseases such as metabolic disorders such as hypercholesterolemia, hyperlipidemia which are exacerbated by hyperinsulinema and hyperglycemia.

The invention also comprises the novel compounds and methods of using them as specified below in formula I. Also included in the scope of the present invention are prodrugs of the compounds of formula I.

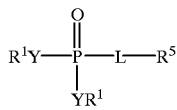

Since these compounds may have asymmetric centers, the present invention is directed not only to racemic mixtures of these compounds, but also to individual stereoisomers. The present invention also includes pharmaceutically acceptable and/or useful salts of the compounds of formula I, including acid addition salts. The present inventions also encompass prodrugs of compounds of formula I.

DETAILED DESCRIPTION

Definitions

In accordance with the present invention and as used herein, the following terms are defined with the following meanings, unless explicitly stated otherwise.

L group nomenclature as used herein in formula I begins with the group attached to the phosphorous and ends with the group attached to the aryl ring. For example, when L is -alkylcarbonylamino-, the following structure is intended:

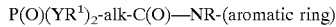

For $J^2$, $J^3$, $J^4$, $J^5$, and $J^6$ groups and other substituents of the $R^5$ aromatic ring, the substituents are described in such a way that the term ends with the group attached to the aromatic ring. Generally, substituents are named such that the term ends with the group at the point of attachment. For example, when $J^2$ is alkylaryl, the intended structure is alkyl-aryl-$G^2$ in the ring.

The term "aryl" refers to aromatic groups which have 5–14 ring atoms and at least one ring having a conjugated pi electron system and includes carbocyclic aryl, heterocyclic aryl and biaryl groups, all of which may be optionally substituted. Suitable aryl groups include phenyl and furan-2,5-diyl.

Carbocyclic aryl groups are groups wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl or heteroaryl groups are groups having from 1 to 4 heteroatoms as ring atoms in the aromatic ring and the remainder of the ring atoms being carbon atoms. Suitable heteroatoms include oxygen, sulfur, nitrogen, and selenium. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "biaryl" represents aryl groups containing more than one aromatic ring including both fused ring systems and aryl groups substituted with other aryl groups. Such groups may be optionally substituted. Suitable biaryl groups include naphthyl and biphenyl.

The term "alicyclic" means compounds which combine the properties of aliphatic and cyclic compounds. Such cyclic compounds include but are not limited to, aromatic, cycloalkyl and bridged cycloalkyl compounds. The cyclic compound includes heterocycles. Cyclohexenylethyl and cyclohexylethyl are suitable alicyclic groups. Such groups may be optionally substituted.

The term "optionally substituted" or "substituted" includes groups substituted by one to four substituents, independently selected from lower alkyl, lower aryl, lower aralkyl, lower alicyclic, heterocyclic alkyl, hydroxy, lower alkoxy, lower aryloxy, perhaloalkoxy, aralkoxy, heteroaryl, heteroaryloxy, heteroarylalkyl, heteroaralkoxy, azido, amino, guanidino, amidino, halo, lower alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, phosphono, sulfonyl, -carboxamidoalkylaryl, -carboxamidoaryl, hydroxyalkyl, haloalkyl, alkylaminoalkylcarboxy-, aminocarboxamidoalkyl-, cyano, lower alkoxyalkyl, lower perhaloalkyl, and arylalkyloxyalkyl. These optional substituents may not be optionally substituted. "Substituted aryl" and "substituted heteroaryl" refers to aryl and heteroaryl groups substituted with 1–3 substituents. In one aspect, suitable substituents are selected from the group consisting of lower alkyl, lower alkoxy, lower perhaloalkyl, halo, hydroxy, and amino. "Substituted" when describing an $R^5$ group does not include annulation.

The term "aralkyl" refers to an alkyl group substituted with an aryl group. Suitable aralkyl groups include benzyl, picolyl, and the like, and may be optionally substituted. The term "-aralkyl-" refers to a divalent group -aryl-alkylene-. Thus, "aralkyl" is synonymous with "aralkylene." "Heteroarylalkyl" refers to an alkylene group substituted with a heteroaryl group.

The term "-alkylaryl-" refers to the group -alk-aryl- where "alk" is an alkylene group. Thus, "-alkylaryl-" is synonymous with "-alkylenearyl-." "Lower -alkylaryl-" refers to such groups where alkylene is lower alkylene.

The term "lower" referred to herein in connection with organic radicals or compounds respectively defines such as with up to and including 10, or up to and including 6, or one to four carbon atoms. Such groups may be straight chain, branched, or cyclic.

The terms "arylamino" (a), and "aralkylamino" (b), respectively, refer to the group —NRR' wherein respectively, (a) R is aryl and R' is hydrogen, alkyl, aralkyl or aryl, and (b) R is aralkyl and R' is hydrogen or aralkyl, aryl, alkyl.

The term "acyl" refers to —C(O)R where R is alkyl or aryl.

The term "carboxy esters" refers to —C(O)OR where R is alkyl, aryl, aralkyl, or alicyclic, all optionally substituted.

The term "carboxyl" refers to —C(O)OH.

The term "oxo" refers to =O in an alkyl group.

The term "amino" refers to —NRR' where R and R' are independently selected from hydrogen, alkyl, aryl, aralkyl and alicyclic, all except H are optionally substituted; and R and R' can form a cyclic ring system.

The term "carbonylamino" and "-carbonylamino-" refers to RCONR— and —CONR—, respectively, where each R is independently hydrogen or alkyl.

The term "halogen" or "halo" refers to —F, —Cl, —Br and —I.

The term "-oxyalkylamino-" refers to —O-alk-NR—, where "alk" is an alkylene group and R is H or alkyl. Thus, "-oxyalkylamino-" is synonymous with "-oxyalkyleneamino-."

The term "-alkylaminoalkylcarboxy-" refers to the group -alk-NR-alk-C(O)—O— where "alk" is an alkylene group, and R is a H or lower alkyl. Thus, "-alkylaminoalkylcarboxy-" is synonymous with "-alkyleneaminoalkylenecarboxy-."

The term "-alkylaminocarbonyl-" refers to the group -alk-NR—C(O)— where "alk" is an alkylene group, and R is a H or lower alkyl. Thus, "-alkylaminocarbonyl-" is synonymous with "-alkyleneaminocarbonyl-."

The term "-oxyalkyl-" refers to the group —O-alk- where "alk" is an alkylene group. Thus, "-oxyalkyl-" is synonymous with "-oxyalkylene-."

The term "-alkylcarboxyalkyl-" refers to the group -alk-C(O)—O-alk- where each alk is independently an alkylene group. Thus, "-alkylcarboxyalkyl-" is synonymous with "-alkylenecarboxyalkylene-."

The term "alkyl" refers to saturated aliphatic groups including straight-chain, branched chain and cyclic groups. Alkyl groups may be optionally substituted. Suitable alkyl groups include methyl, isopropyl, and cyclopropyl.

The term "cyclic alkyl" or "cycloalkyl" refers to alkyl groups that are cyclic groups of 3 to 6 or 3 to 10 atoms. Suitable cyclic groups include norbornyl and cyclopropyl. Such groups may be substituted.

The term "heterocyclic" and "heterocyclic alkyl" refer to cyclic groups of 3 to 6 atoms, or 3 to 10 atoms, containing at least one heteroatom. In one aspect, these groups contain 1 to 3 heteroatoms. Suitable heteroatoms include oxygen, sulfur, and nitrogen. Heterocyclic groups may be attached through a nitrogen or through a carbon atom in the ring. Suitable heterocyclic groups include pyrrolidinyl, morpholino, morpholinoethyl, and pyridyl. Such groups may be substituted.

The term "phosphono" refers to —PO$_3$R$_2$, where R is selected from the group consisting of —H, alkyl, aryl, aralkyl, and alicyclic.

The term "sulphonyl" or "sulfonyl" refers to —S(O)$_2$OR, where R is selected from the group of H, alkyl, aryl, aralkyl, or alicyclic.

The term "alkenyl" refers to unsaturated groups which contain at least one carbon-carbon double bond and includes straight-chain, branched-chain and cyclic groups. Alkenyl groups may be optionally substituted. Suitable alkenyl groups include allyl. "1-alkenyl" refers to alkenyl groups where the double bond is between the first and second carbon atom. If the 1-alkenyl group is attached to another group, e.g. it is a W substituent attached to the cyclic phosphonate or phosphoramidate, it is attached at the first carbon.

The term "alkynyl" refers to unsaturated groups which contain at least one carbon-carbon triple bond and includes straight-chain, branched-chain and cyclic groups. Alkynyl groups maybe optionally substituted. Suitable alkynyl groups include ethynyl. "1-alkynyl" refers to alkynyl groups where the triple bond is between the first and second carbon atom. If the 1-alkynyl group is attached to another group, e.g. it is a W substituent attached to the cyclic phosphonate or phosphoramidate, it is attached at the first carbon.

The term "alkylene" refers to a divalent straight chain, branched chain or cyclic saturated aliphatic group.

The term "-cycloalkylene-COOR$^3$" refers to a divalent cyclic alkyl group or heterocyclic group containing 4 to 6 atoms in the ring, with 0–1 heteroatoms selected from O, N, and S. The cyclic alkyl or heterocyclic group is substituted with —COOR$^3$.

The term "acyloxy" refers to the ester group —O—C(O) R, where R is H, alkyl, alkenyl, alkynyl, aryl, aralkyl, or alicyclic.

The term "aminoalkyl-" refers to the group NR$_2$-alk- wherein "alk" is an alkylene group and R is selected from the group of H, alkyl, aryl, aralkyl, and alicyclic.

The term "alkylaminoalkyl-" refers to the group alkyl-NR-alk- wherein each "alk" is an independently selected alkylene, and R is H or lower alkyl. Thus, "alkylaminoalkyl-" is synonymous with "alkylaminoalkylene-." "Lower alkylaminoalkyl-" refers to groups where each alkylene group is lower alkylene.

The term "arylaminoalkyl-" refers to the group aryl-NR-alk- wherein "alk" is an alkylene group and R is H, alkyl, aryl, aralkyl, and alicyclic. Thus, "arylaminoalkyl-" is synonymous with "arylaminoalkylene-." In "lower arylaminoalkyl-", the alkylene group is lower alkylene.

The term "alkylaminoaryl-" refers to the group alkyl-NR-aryl- wherein "aryl" is a divalent group and R is H, alkyl, aralkyl, and alicyclic. In "lower alkylaminoaryl-", the alkyl group is lower alkyl.

The term "alkyloxyaryl-" refers to an aryl group substituted with an alkyloxy group. In "lower alkyloxyaryl-", the alkyl group is lower alkyl.

The term "aryloxyalkyl-" refers to an alkyl group substituted with an aryloxy group. Thus, "aryloxyalkyl-" is synonymous with "aryloxyalkylene-."

The term "aralkyloxyalkyl-" refers to the group aryl-alk-O-alk- wherein "alk" is an alkylene group. Thus, "aralkyloxyalkyl-" is synonymous with "aralkyloxyalkylene-." "Lower aralkyloxyalkyl-" refers to such groups where the alkylene groups are lower alkylene.

The term "-alkoxy-" or "-alkyloxy-" refers to the group -alk—O— wherein "alk" is an alkylene group. Thus, "-alkoxy-" and "-alkyloxy-" are synonymous with "-alkyleneoxy-." The term "alkoxy-" refers to the group alkyl-O—.

The term "-alkoxyalkyl-" or "-alkyloxyalkyl-" refer to the group -alk-O-alk-wherein each "alk" is an independently selected alkylene group. Thus, "-alkoxyalkyl-" and "-alkyloxyalkyl-" are synonymous with "-alkyleneoxyalkylene-." In "lower -alkoxyalkyl-", each alkylene is lower alkylene.

The terms "alkylthio-" and "-alkylthio-" refer to the groups alkyl-S—, and -alk-S—, respectively, wherein "alk" is alkylene group. Thus, "-alkylthio-" is synonymous with "-alkylenethio-."

The term "-alkylthioalkyl-" refers to the group -alk-S-alk- wherein each "alk" is an independently selected alkylene group. Thus, "-alkylthioalkyl-" is synonymous with "-alkylenethioalkylene-." In "lower -alkylthioalkyl-" each alkylene is lower alkylene.

The term "alkoxycarbonyloxy-" refers to alkyl-O—C(O)—O—.

The term "aryloxycarbonyloxy-" refers to aryl-O—C(O)—O—.

The term "alkylthiocarbonyloxy-" refers to alkyl-S—C(O)—O—.

The term "-alkoxycarbonylamino-" refers to -alk-O—C(O)—NR$^1$—, where "alk" is alkylene and R$^1$ includes —H, alkyl, aryl, alicyclic, and aralkyl. Thus, "-alkoxycarbonylamino-" is synonymous with "-alkyleneoxycarbonylamino-."

The term "-alkylaminocarbonylamino-" refers to -alk-NR$^1$—C(O)—NR$^1$—, where "alk" is alkylene and R$^1$ is independently selected from H, alkyl, aryl, aralkyl, and alicyclic. Thus, "-alkylaminocarbonylamino-" is synonymous with "-alkyleneaminocarbonylamino-."

The terms "amido" or "carboxamido" refer to NR$_2$—C(O)— and RC(O)—NR$^1$—, where R and R$^1$ include H, alkyl, aryl, aralkyl, and alicyclic. The term does not include urea, —NR—C(O)—NR—.

The terms "carboxamidoalkylaryl" and "carboxamidoaryl" refer to an ar-alk-NR$^1$—C(O)—, and ar-NR$^1$—C(O)—, respectively, where "ar" is aryl, and "alk" is alkylene, R$^1$ and R include H, alkyl, aryl, aralkyl, and alicyclic. Thus, "carboxamidoalkylaryl" is synonymous with "carboxamidoalkylenearyl."

The term "-alkylcarboxamido-" or "-alkylcarbonylamino-" refers to the group -alk-C(O)N(R)— wherein "alk" is an alkylene group and R is H or lower alkyl. Thus, "-alkylcarboxamido-" and "-alkylcarbonylamino-" are synonymous with "-alkylenecarboxamido-" and "-alkylenecarbonylamino-," respectively.

The term "-alkylaminocarbonyl-" refers to the group -alk-NR—C(O)— wherein "alk" is an alkylene group and R is H or lower alkyl. Thus, "-alkylaminocarbonyl-" is synonymous with "-alkyleneaminocarbonyl-."

The term "aminocarboxamidoalkyl-" refers to the group NR$_2$—C(O)—N(R)-alk- wherein R is an alkyl group or H and "alk" is an alkylene group. Thus, "aminocarboxamidoalkyl-" is synonymous with "aminocarboxamidoalkylene-." "Lower aminocarboxamidoalkyl-" refers to such groups wherein "alk" is lower alkylene.

The term "thiocarbonate" refers to —O—C(S)—O— either in a chain or in a cyclic group.

The term "hydroxyalkyl" refers to an alkyl group substituted with one —OH.

The term "haloalkyl" refers to an alkyl group substituted with one halo, selected from the group I, Cl, Br, F.

The term "cyano" refers to —C≡N.

The term "nitro" refers to —NO$_2$.

The term "acylalkyl" refers to an alkyl-C(O)-alk-, where "alk" is alkylene. Thus, "acylalkyl" is synonymous with "acylalkylene."

The term "heteroarylalkyl" refers to an alkyl group substituted with a heteroaryl group.

The term "perhalo" refers to groups wherein every C—H bond has been replaced with a C-halo bond on an aliphatic or aryl group. Suitable perhaloalkyl groups include —CF$_3$ and —CFCl$_2$.

The term "guanidino" refers to both —NR—C(NR)—NR$_2$ as well as —N═C(NR$_2$)$_2$ where each R group is independently selected from the group of —H, alkyl, alkenyl, alkynyl, aryl, and alicyclic, all except —H are optionally substituted.

The term "amidino" refers to —C(NR)—NR$_2$ where each R group is independently selected from the group of —H, alkyl, alkenyl, alkynyl, aryl, and alicyclic, all except —H are optionally substituted.

The term "pharmaceutically acceptable salt" includes salts of compounds of formula I and its prodrugs derived from the combination of a compound of this invention and an organic or inorganic acid or base. Suitable acids include hydrochloric acid, hydrobromic acid, acetic acid, trifluoroacetic acid, methanesulfonic acid, p-toluenesulfonic acid and maleic acid.

The term "prodrug" as used herein refers to any compound that when administered to a biological system generates the "drug" substance (a biologically active compound) in one or more steps involving spontaneous chemical reaction(s), enzyme catalyzed chemical reaction (s), or both. Standard prodrugs are formed using groups attached to functionality, e.g. HO—, HS—, HOOC—, R$_2$N—, associated with the FBPase inhibitor, that cleave in vivo. Prodrugs for these groups are well known in the art and are often used to enhance oral bioavailability or other properties beneficial to the formulation, delivery, or activity of the drug. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Standard prodrugs of phosphonic acids are also included and may be represented by R$^1$ in formula I. The groups illustrated are exemplary, not exhaustive, and one skilled in the art could prepare other known varieties of prodrugs. Such prodrugs of the compounds of formula I fall within the scope of the present invention. Prodrugs must undergo some form of a chemical transformation to produce the compound that is biologically active. In some cases, the prodrug is biologically active usually less than the drug itself, and serves to improve efficacy or safety through improved oral bioavailability, pharmacodynamic half-life, etc.

The term "prodrug ester" as employed herein refers to esters of phosphonic acids or phosphoramic acids and includes, but is not limited to, the following groups and combinations of these groups:

[1] Acyloxyalkyl esters which are well described in the literature (Farquhar et al., *J. Pharm. Sci.* 72, 324–325 (1983)) and are represented by formula A

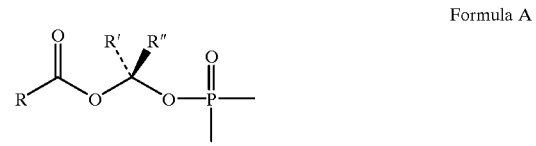

Formula A wherein R, R', and R" are independently H, alkyl, aryl, alkylaryl, and alicyclic; (see WO 90/08155; WO 90/10636).

[2] Other acyloxyalkyl esters are possible in which an alicyclic ring is formed such as shown in formula B. These esters have been shown to generate phosphorus-containing nucleotides inside cells through a postulated sequence of reactions beginning with deesterification and followed by a series of elimination reactions (e.g. Freed et al., *Biochem. Pharm.* 38: 3193–3198 (1989)).

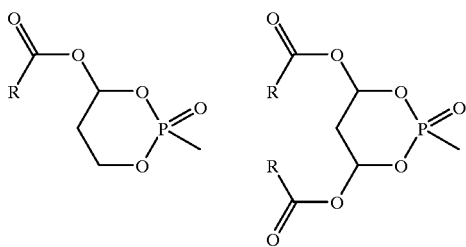

Formula B wherein R is —H, alkyl, aryl, alkylaryl, alkoxy, aryloxy, alkylthio, arylthio, alkylamino, arylamino, cycloalkyl, or alicyclic.

[3] Another class of these double esters known as alkyloxycarbonyloxymethyl esters, as shown in formula A, where R is alkoxy, aryloxy, alkylthio, arylthio, alkylamino, and arylamino; R', and R" are independently H, alkyl, aryl, alkylaryl, and alicyclic, have been studied in the area of β-lactam antibiotics (Tatsuo Nishimura et al. *J. Antibiotics*, 1987, 40(1), 81–90; for a review see Ferres, H., *Drugs of Today*, 1983,19, 499.). More recently Cathy, M. S., et al. (Abstract from AAPS Western Regional Meeting, April, 1997) showed that these alkyloxycarbonyloxymethyl ester prodrugs on (9-[(R)-2-phosphonomethoxy)propyl]adenine (PMPA) are bioavailable up to 30% in dogs.

[4] Aryl esters have also been used as phosphonate prodrugs (e.g. Erion, DeLambert et al., *J. Med. Chem.* 37: 498, 1994; Serafinowska et al., *J. Med. Chem.* 38: 1372, 1995). Phenyl as well as mono and poly-substituted phenyl proesters have generated the parent phosphonic acid in studies conducted in animals and in man (Formula C). Another approach has been described where Y is a carboxylic ester ortho to the phosphate. Khamnei and Torrence, *J. Med. Chem.*; 39:4109–4115 (1996).

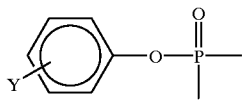

Formula C wherein: Y is H, alkyl, aryl, alkylaryl, alkoxy, acyloxy, halogen, amino, alkoxycarbonyl, hydroxy, cyano, and alicyclic.

[5] Benzyl esters have also been reported to generate the parent phosphonic acid. In some cases, using substituents at the para-position can accelerate the hydrolysis. Benzyl analogs with 4-acyloxy or 4-alkyloxy group [Formula D, X=H, OR or O(CO)R or O(CO)OR] can generate the 4-hydroxy compound more readily through the action of enzymes, e.g. oxidases, esterases, etc. Examples of this class of prodrugs are described in Mitchell et al., *J. Chem. Soc. Perkin Trans.* I 2345 (1992); Brook, et al. WO 91/19721.

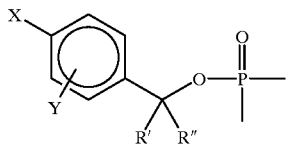

Formula D wherein X and Y are independently H, alkyl, aryl, alkylaryl, alkoxy, acyloxy, hydroxy, cyano, nitro, perhaloalkyl, halo, or alkyloxycarbonyl; and R' and R" are independently H, alkyl, aryl, alkylaryl, halogen, and alicyclic.

[6] Thio-containing phosphonate proesters have been described that are useful in the delivery of FBPase inhibitors to hepatocytes. These proesters contain a protected thioethyl moiety as shown in formula E. One or more of the oxygens of the phosphonate can be esterified. Since the mechanism that results in de-esterification requires the generation of a free thiolate, a variety of thiol protecting groups are possible. For example, the disulfide is reduced by a reductase-mediated process (Puech et al., *Antiviral Res.*, 22: 155–174 (1993)). Thioesters will also generate free thiolates after esterase-mediated hydrolysis. Benzaria, et al., *J. Med. Chem.*, 39:4958 (1996). Cyclic analogs are also possible and were shown to liberate phosphonate in isolated rat hepatocytes. The cyclic disulfide shown below has not been previously described and is novel.

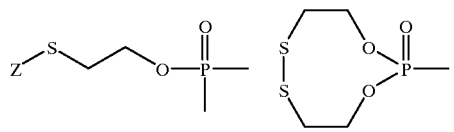

Formula E wherein Z is alkylcarbonyl, alkoxycarbonyl, arylcarbonyl, aryloxycarbonyl, or alkylthio.

Other examples of suitable prodrugs include proester classes exemplified by Biller and Magnin (U.S. Pat. No. 5,157,027); Serafinowska et al. (*J. Med. Chem.* 38, 1372 (1995)); Starrett et al. (*J. Med. Chem.* 37, 1857 (1994)); Martin et al. *J. Pharm. Sci.* 76, 180 (1987); Alexander et al., *Collect. Czech. Chem. Commun,* 59, 1853 (1994)); and EPO patent application 0 632 048 A1. Some of the structural classes described are optionally substituted, including fused lactones attached at the omega position (formulae E-1 and E-2) and optionally substituted 2-oxo-1,3-dioxolenes attached through a methylene to the phosphorus oxygen (formula E-3) such as:

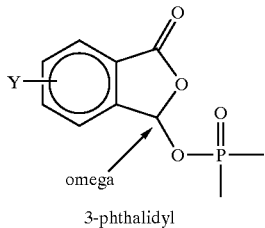

E-1

3-phthalidyl

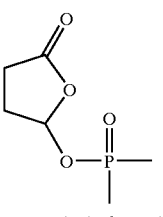

E-2

2-oxotetrahydrofuran-5-yl

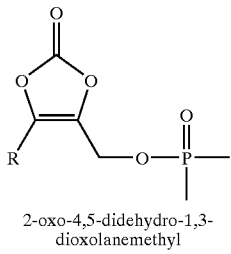

2-oxo-4,5-didehydro-1,3-
dioxolanemethyl wherein R is —H, alkyl, cycloalkyl, or alicyclic; and wherein Y is —H, alkyl, aryl, alkylaryl, cyano, alkoxy, acyloxy, halogen, amino, alicyclic, and alkoxycarbonyl.

The prodrugs of Formula E-3 are an example of "optionally substituted alicyclic where the cyclic moiety contains a carbonate or thiocarbonate."

[7] Propyl phosphonate proesters can also be used to deliver FBPase inhibitors into hepatocytes. These proesters may contain a hydroxyl and hydroxyl group derivatives at the 3-position of the propyl group as shown in formula F. The R and X groups can form a cyclic ring system as shown in formula F. One or more of the oxygens of the phosphonate can be esterified.

Formula F

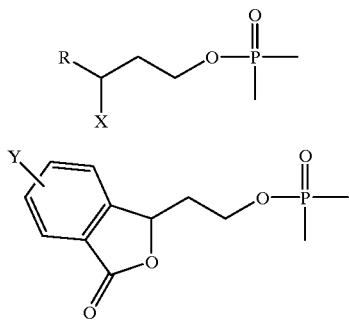

wherein R is alky, aryl, heteroaryl; X is hydrogen, alkylcarbonyloxy, alkyloxycarbonyloxy; and Y is alkyl, aryl, heteroaryl, alkoxy, alkylamino, alkylthio, halogen, hydrogen, hydroxy, acyloxy, amino.

[8] Phosphoramidate derivatives have been explored as phosphate prodrugs (e.g. McGuigan et al., *J. Med. Chem.*, 1999, 42: 393 and references cited therein) as shown in Formula G and H.

Formula G

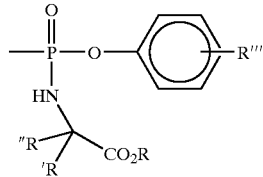

Formula H

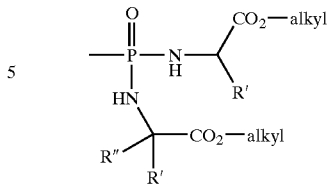

Cyclic phosphoramidates have also been studied as phosphonate prodrugs because of their speculated higher stability compared to non-cyclic phosphoramidates (e.g. Starrett et al., *J. Med. Chem.*, 1994, 37: 1857.

Another type of nucleotide prodrug was reported as the combination of S-acyl-2-thioethyl ester and phosphoramidate (Egron et al., *Nucleosides & Nucleotides*, 1999, 18, 981) as shown in Formula I.

Formula I

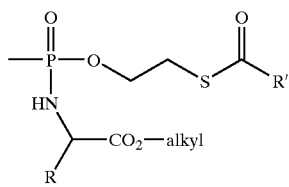

Other prodrugs are possible based on literature reports such as substituted ethyls for example, bis(trichloroethyl) esters as disclosed by McGuigan, et al. *Bioorg Med. Chem. Lett.*, 3:1207–1210 (1993), and the phenyl and benzyl combined nucleotide esters reported by Meier, C. et al. *Bioorg. Med. Chem. Lett.*, 7:99–104 (1997).

The structure

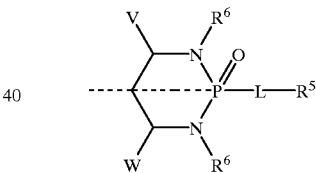

has a plane of symmetry running through the phosphorus-oxygen double bond when $R^6=R^6$, $V=W$, and V and W are either both pointing up or both pointing down. The same is true of structures where each —$NR^6$ is replaced with —O—. The stereochemistry where V is trans to the phosphorus-oxygen double bond is envisioned.

The term "cyclic 1',3'-propane ester", "cyclic 1,3-propane ester", "cyclic 1',3'-propanyl ester", and "cyclic 1,3-propanyl ester" refers to the following:

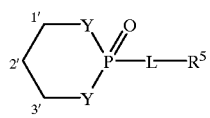

The phrase "together $V^2$ and $Z^2$ are connected via an additional 3–5 atoms to form a cyclic group containing 5–7 ring atoms, optionally containing 1 heteroatom, substituted with hydroxy, acyloxy, alkoxycarbonyloxy, or aryloxycarbonyloxy attached to a carbon atom that is three atoms from both Y groups attached to the phosphorus" includes the following:

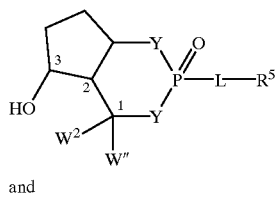

and

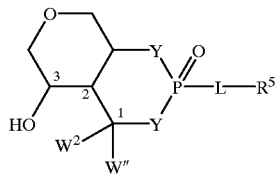

The structure shown above (left) has an additional 3 carbon atoms that forms a five member cyclic group. Such cyclic groups must possess the listed substitution to be oxidized.

The phrase "together V and Z are connected via an additional 3–5 atoms to form a cyclic group, optionally containing one heteroatom, said cyclic group is fused to an aryl group at the beta and gamma position to the Y adjacent to V includes the following:

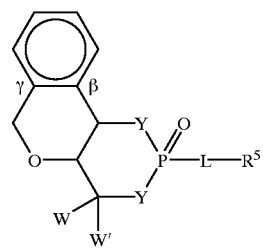

The phrase "together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a Y attached to the phosphorus" includes the following:

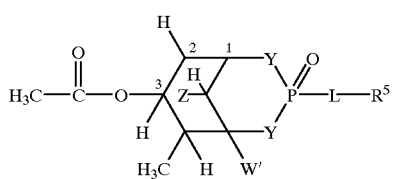

The structure above has an acyloxy substituent that is three carbon atoms from a Y, and an optional substituent, —$CH_3$, on the new 6-membered ring. There has to be at least one hydrogen at each of the following positions: the carbon attached to Z; both carbons alpha to the carbon labeled "3"; and the carbon attached to "OC(O)$CH_3$" above.

The phrase "together W and W' are connected via an additional 2–5 atoms to form a cyclic group, optionally containing 0–2 heteroatoms, and V must be aryl, substituted aryl, heteroaryl, or substituted heteroaryl" includes the following:

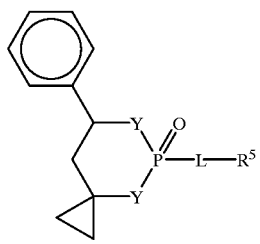

The structure above has V=aryl, a spiro-fused cyclopropyl group for W and W', and Z=H.

The term "cyclic phosphonate" or "cyclic phosphoramidate" refers to

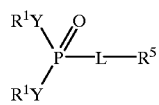

where together $R^1$ and $R^1$ are

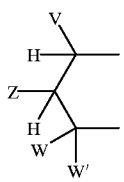

or

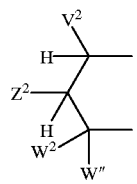

or

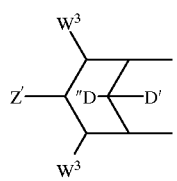

where Y is independently —O— or —$NR^6$—. The carbon attached to Z' must have a C—H bond.

The term "enhancing" refers to increasing or improving a specific property.

The term "enhanced oral bioavailability" refers to an increase of at least 50% of the absorption of the dose of the parent drug or prodrug (not of this invention) from the gastrointestinal tract. In some cases it is at least 100%. Measurement of oral bioavailability usually refers to measurements of the prodrug, drug, or drug metabolite in blood, tissues, or urine following oral administration compared to measurements following systemic administration.

The term "parent drug" refers to any compound which delivers the same biologically active compound. The parent drug form is P(O)(OH)$_2$—L—$R^5$ and standard prodrugs, such as esters.

The term "drug metabolite" refers to any compound produced in vivo or in vitro from the parent drug, which can include the biologically active drug.

The term "biologically active drug or agent" refers to the chemical entity that produces a biological effect. Thus, active drugs or agents include compounds which as P(O)(OH)$_2$—L—R$^5$ are biologically active.

The term "therapeutically effective amount" refers to an amount that has any beneficial effect in treating a disease or condition.

Compounds of Formula I

Suitable alkyl groups include groups having from 1 to about 20 carbon atoms. Suitable aryl groups include groups having from 1 to about 20 carbon atoms. Suitable aralkyl groups include groups having from 2 to about 21 carbon atoms. Suitable acyloxy groups include groups having from 1 to about 20 carbon atoms. Suitable alkylene groups include groups having from 1 to about 20 carbon atoms. Suitable alicyclic groups include groups having 3 to about 20 carbon atoms. Suitable heteroaryl groups include groups having from 1 to about 20 carbon atoms and from 1 to 4 heteroatoms, independently selected from nitrogen, oxygen, phosphorous, and sulfur. Suitable heteroalicyclic groups include groups having from 2 to about twenty carbon atoms and from 1 to 5 heteroatoms, independently selected from nitrogen, oxygen, phosphorous, and sulfur.

In the method claims, representative are the following compounds of formula (I):

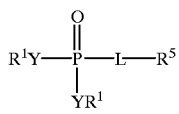
(I)

wherein R$^5$ is selected from the group consisting of:

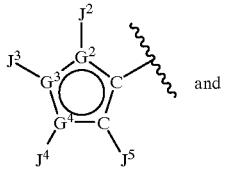
I(a)

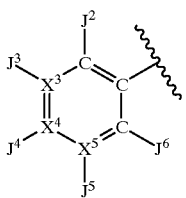
I(b)

wherein:

G$^2$ is selected from the group consisting of C, O, and S;

G$^3$ and G$^4$ are independently selected from the group consisting of C, N, O, and S;

wherein a) not more than one of G$^2$, G$^3$, and G$^4$ may be O, or S; b) when G$^2$ is O or S, not more than one of G$^3$ and G$^4$ is N; c) at least one of G$^2$, G$^3$, and G$^4$ is C; and d) G$^2$, G$^3$, and G$^4$ are not all C;

X$^3$, X$^4$, and X$^5$ are independently selected from the group consisting of C and N, wherein no more than two of X$^3$, X$^4$, and X$^5$ may be N;

J$^2$, J$^3$, J$^4$, J$^5$, and J$^6$ are independently selected from the group consisting of —H, —NR$^4$$_2$, —CONR$^4$$_2$, —CO$_2$R$^3$, halo, —S(O)$_2$NR$^4$$_2$, —S(O)R$^3$, —SO$_2$R$^3$, alkyl, alkenyl, alkynyl, alkylaryl, perhaloalkyl, haloalkyl, aryl, heteroaryl, alkylene-OH, —C(O)R$^{11}$, —OR$^{11}$, -alkylene-NR$^4$$_2$, -alkylene-CN, —CN, —C(S)NR$^4$$_2$, —OR$^2$, —SR$^2$, —N$^3$, —NO$_2$, —NHC(S)NR$^4$$_2$, and —NR$^{18}$COR$^2$;

L is selected from the group consisting of:

i) a linking group having 2–4 atoms measured by the fewest number of atoms connecting the carbon of the aromatic ring and the phosphorus atom and is selected from the group consisting of -furanyl-, -thienyl-, -pyridyl-, -oxazolyl-, -imidazolyl-, -phenyl-, -pyrimidinyl-, -pyrazinyl-, and -alkynyl-, all of which may be optionally substituted; and ii) a linking group having 3–4 atoms measured by the fewest number of atoms connecting the carbon of the aromatic ring and the phosphorus atom and is selected from the group consisting of -alkylcarbonylamino-, -alkylaminocarbonyl-, -alkoxycarbonyl-, -alkoxy-, -alkylthio-, -alkylcarbonyloxy-, -alkyl-S(O)—, -alkyl-S(O)$_2$—, and -alkoxyalkyl-, all of which may be optionally substituted;

Y is independently selected from the group consisting of —O—, and —NR$^6$—;

when Y is —O—, then R$^1$ attached to —O— is independently selected from the group consisting of —H, alkyl, optionally substituted aryl, optionally substituted alicyclic where the cyclic moiety contains a carbonate or thiocarbonate, optionally substituted arylalkylene-, —C(R$^2$)$_2$OC(O)NR$^2$$_2$, —NR$^2$—C(O)—R$^3$, —C(R$^2$)$_2$—OC(O)R$^3$, —C(R$^2$)$_2$—O—C(O)OR$^3$, —C(R$^2$)$_2$OC(O)SR$^3$, -alkyl-S—C(O)R$^3$, -alkyl-S—S-alkylhydroxy, and -alkyl-S—S—S-alkylhydroxy, when one Y is —NR$^6$—, and R$^1$ attached to it is —(CR$^{12}$R$^{13}$)$_n$—C(O)—R$^{14}$, then the other —YR$^1$ is selected from the group consisting of —NR$^{15}$R$^{16}$, —OR$^7$, and NR$^6$—(CR$^{12}$R$^{13}$)$_n$—C(O)—R$^{14}$;

or when either Y is independently selected from —O— and —NR$^6$—, then together R$^1$ and R$^1$ are -alkyl-S—S-alkyl- to form a cyclic group, or together R$^1$ and R$^1$ are

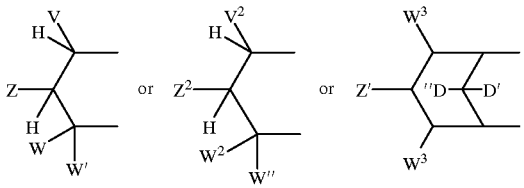

wherein a) V is selected from the group of aryl, substituted aryl, heteroaryl, substituted heteroaryl, 1-alkynyl and 1-alkenyl;

Z is selected from the group of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R, —OR$^2$, —SR$^2$, —CHR$^2$N$_3$, —CH$_2$aryl, —CH(aryl)OH, —CH(CH=CR$^2$$_2$)OH, —CH(C≡CR$^2$)OH, —R$^2$, —NR$^2$$_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^{19}$, and —(CH$_2$)$_p$—SR$^{19}$; or together V and Z are connected via an additional 3–5 atoms to form a cyclic group, optionally containing 1 heteroatom, said cyclic group is fused to an aryl group at the beta and gamma position to the Y adjacent to V; or together Z and W are connected via an additional 3–5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl and —R$^9$; or together W and W' are connected via an additional 2–5 atoms to form a cyclic group, optionally containing 0–2 heteroatoms, and V must be aryl, substituted aryl, heteroaryl, or substituted heteroaryl; or b) $V^2$, $W^2$ and $W'''$ are independently selected from the group of —H, alkyl, aralkyl, alicyclic, aryl, substituted aryl, heteroaryl, substituted heteroaryl, 1-alkenyl, and 1-alkynyl;

$Z^2$ is selected from the group of —$CHR^2OH$, —$CHR^2OC(O)R^3$, —$CHR^2OC(S)R^3$, —$CHR^2OCO_2R^3$, —$CHR^2OC(O)SR^3$, —$CHR^2OC(S)OR^3$, —$CH(aryl)OH$, —$CH(CH=CR^2{}_2)OH$, —$CH(C\equiv CR^2)OH$, —$SR^2$, —$CH_2NHaryl$, —$CH_2aryl$; or together $V^2$ and $Z^2$ are connected via an additional 3–5 atoms to form a cyclic group containing 5–7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —$OC(O)R^3$, —$OCO_2R^3$, and —$OC(O)SR^3$;

D' is —H;

D'' is selected from the group of —H, alkyl, —$OR^2$, —OH, and —$OC(O)R^3$;

each $W^3$ is independently selected from the group consisting of —H, alkyl, aralkyl, alicyclic, aryl, substituted aryl, heteroaryl, substituted heteroaryl, 1-alkenyl, and 1-alkynyl;

p is an integer 2 or 3;

with the provisos that:

a) V, Z, W, W' are not all —H and $V^2$, $Z^2$, $W^2$, $W'''$ are not all —H; and $R^2$ is selected from the group consisting of $R^3$ and —H;

$R^3$ is selected from the group consisting of alkyl, aryl, alicyclic, and aralkyl;

each $R^4$ is independently selected from the group consisting of —H, alkyl, -alkylenearyl, and aryl, or together $R^4$ and $R^4$ are connected via 2–6 atoms, optionally including one heteroatom selected from the group consisting of O, N, and S;

$R^6$ is selected from the group consisting of —H, lower alkyl, acyloxyalkyl, aryl, aralkyl, alkoxycarbonyloxyalkyl, and lower acyl, or together with $R^{12}$ is connected via 1–4 carbon atoms to form a cyclic group;

$R^7$ is lower $R^3$;

each $R^9$ is independently selected from the group consisting of —H, alkyl, aralkyl, and alicyclic, or together $R^9$ and $R^9$ form a cyclic alkyl group;

$R^{11}$ is selected from the group consisting of alkyl, aryl, —$NR^2{}_2$, and —$OR^2$; and each $R^{12}$ and $R^{13}$ is independently selected from the group consisting of H, lower alkyl, lower aryl, lower aralkyl, all optionally substituted, or $R^{12}$ and $R^{13}$ together are connected via a chain of 2–6 atoms, optionally including 1 heteroatom selected from the group consisting of O, N, and S, to form a cyclic group;

each $R^{14}$ is independently selected from the group consisting of —$OR^{17}$, —$N(R^{17})_2$, —$NHR^{17}$, —$SR^{17}$, and —$NR^2OR^{20}$;

$R^{15}$ is selected from the group consisting of —H, lower aralkyl, lower aryl, lower aralkyl, or together with $R^{16}$ is connected via 2–6 atoms, optionally including 1 heteroatom selected from the group consisting of O, N, and S;

$R^{16}$ is selected from the group consisting of —$CR^{12}R^{13})_n$—$C(O)$—$R^{14}$, —H, lower alkyl, lower aryl, lower aralkyl, or together with $R^{15}$ is connected via 2–6 atoms, optionally including 1 heteroatom selected from the group consisting of O, N, and S;

each $R^{17}$ is independently selected from the group consisting of lower alkyl, lower aryl, and lower aralkyl, or together $R^{17}$ and $R^{17}$ on N is connected via 2–6 atoms, optionally including 1 heteroatom selected from the group consisting of O, N, and S;

$R^{18}$ is selected from the group consisting of —H and lower $R^3$;

$R^{19}$ is selected from the group consisting of —H, and lower acyl;

$R^{20}$ is selected from the group consisting of —H, and lower $R^3$, and —C(O)-(lower $R^3$);

n is an integer from 1 to 3;

with the provisos that:

1) when $X^3$, $X^4$, or $X^5$ is N, then the respective $J^3$, $J^4$, or $J^5$ is null;

2) when $G^2$, $G^3$, or $G^4$ is O or S, then the respective $J^2$, $J^3$, or $J^4$ is null;

3) when $G^3$ or $G^4$ is N, then the respective $J^3$ or $J^4$ is not halogen or a group directly bonded to $G^3$ or $G^4$ via a heteroatom;

4) if both Y groups are —$NR^6$—, and $R^1$ and $R^1$ are not connected to form a cyclic phosphoramidate, then at least one $R^1$ is —$(CR^{12}R^{13})_n$—$C(O)$—$R^{14}$;

5) $R^1$ can be selected from the lower alkyl only when the other $YR^1$ is —$NR^6$—$C(R^{12}R^{13})_n$—$C(O)$—$R^{14}$;

and pharmaceutically acceptable prodrugs and salts thereof.

In the method claims, suitable L groups include i) a linking group having 2–4 atoms measured by the fewest number of atoms connecting the carbon of the aromatic ring and the phosphorus atom and is selected from the group consisting of -furanyl-, -thienyl-, -pyridyl-, -oxazolyl-, -imidazolyl-, -pyrimidinyl-, -pyrazinyl-, and -alkynyl-, all of which may be optionally substituted; and ii) a linking group having 3–4 atoms measured by the fewest number of atoms connecting the carbon of the aromatic ring and the phosphorus atom and is selected from the group consisting of -alkylcarbonylamino-, alkylaminocarbonyl-, -alkoxycarbonyl-, -alkoxy-, -alkylthio-, -alkylcarbonyloxy-, -alkyl-S(O)—, -alkyl-S(O)$_2$—, and -alkoxyalkyl-, all of which may be optionally substituted;

In one aspect of the invention in the method claims and in the compound claims are the following compounds:

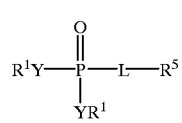

(1)

wherein $R^5$ is selected from the group consisting of:

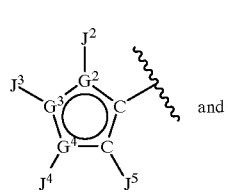

I(a)

and

-continued

I(b)

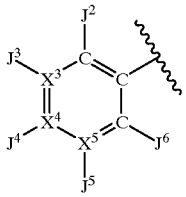

wherein:

G² is selected from the group consisting of C, O, and S;

G³ and G⁴ are independently selected from the group consisting of C, N, O, and S; wherein a) not more than one of G², G³, and G⁴ may be O, or S; b) when G² is O or S, not more than one of G³ and G⁴ is N; c) at least one of G², G³, and G⁴ is C; and d) G², G³, and G⁴ are not all C;

X³, X⁴, and X⁵ are independently selected from the group consisting of C and N, wherein no more than two of X³, X⁴, and X⁵ may be N;

J², J³, J⁴, J⁵, and J⁶ are independently selected from the group consisting of —H, —NR⁴₂, —CONR⁴₂, —CO₂R³, halo, —S(O)₂NR⁴₂, —S(O)R³, —SO₂R³, alkyl, alkenyl, alkynyl, alkylaryl, perhaloalkyl, haloalkyl, aryl, heteroaryl, alkylene-OH, —C(O)R¹¹, —OR¹¹, -alkylene-NR⁴₂, -alkylene-CN, —CN, —C(S)NR⁴₂, —OR², —SR², —N₃, —NO₂, —NHC(S)NR⁴₂, and —NR¹⁸COR²;

L is selected from the group consisting of:

i) a linking group having 2–4 atoms measured by the fewest number of atoms connecting the carbon of the aromatic ring and the phosphorus atom and is selected from the group consisting of -furanyl-, -thienyl-, -pyridyl-, -oxazolyl-, -imidazolyl-, -phenyl-, -pyrimidinyl-, -pyrazinyl-, and -alkynyl-, all of which may be optionally substituted; and ii) a linking group having 3–4 atoms measured by the fewest number of atoms connecting the carbon of the aromatic ring and the phosphorus atom and is selected from the group consisting of -alkylcarbonylamino-, -alkylaminocarbonyl-, -alkoxycarbonyl-, -alkoxy-, and -alkoxyalkyl-, all of which may be optionally substituted;

Y is independently selected from the group consisting of —O—, and —NR⁶—;

when Y is —O—, then R¹ attached to —O— is independently selected from the group consisting of —H, alkyl, optionally substituted aryl, optionally substituted alicyclic where the cyclic moiety contains a carbonate or thiocarbonate, optionally substituted arylalkylene-, —C(R²)₂OC(O)NR²₂, —NR²—C(O)—R³, —C(R²)₂—OC(O)R³, —C(R²)₂—O—C(O)OR³, —C(R²)₂OC(O)SR³, -alkyl-S—C(O)R³, -alkyl-S—S-alkylhydroxy, and -alkyl-S—S—S-alkylhydroxy, when one Y is —NR⁶—, and R¹ attached to it is —(CR¹²R¹³)ₙ—C(O)—R¹⁴, then the other YR¹ is selected from the group consisting of —NR¹⁵R¹⁶, —OR⁷, and NR⁶—(CR¹²R¹³)ₙ—C(O)—R¹⁴;

or when either Y is independently selected from —O— and —NR⁶—, then together R¹ and R¹ are -alkyl-S—S-alkyl- to form a cyclic group, or together R¹ and R' are

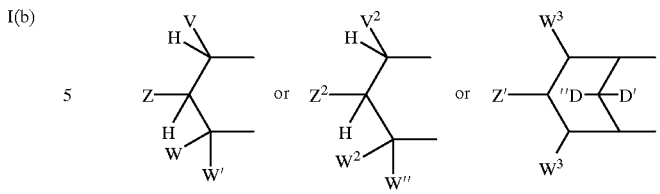

wherein a) V is selected from the group of aryl, substituted aryl, heteroaryl, substituted heteroaryl, 1-alkynyl and 1-alkenyl;

Z is selected from the group of —CHR²OH, —CHR²OC(O)R³, —CHR²OC(S)R³, —CHR²OC(S)OR³, —CHR²OC(O)SR³, —CHR²OCO₂R³, —OR², —SR², —CHR²N₃, —CH₂aryl, —CH(aryl)OH, —CH(CH=CR²₂)OH, —CH(C≡CR²)OH, —R², —NR²₂, —OCOR³, —OCO₂R³, —SCOR³, —SCO₂R³, —NHCOR², —NHCO₂R³, —CH₂NHaryl, —(CH₂)ₚ—OR¹⁹, and —(CH₂)ₚ—SR¹⁹; or together V and Z are connected via an additional 3–5 atoms to form a cyclic group, optionally containing 1 heteroatom, said cyclic group is fused to an aryl group at the beta and gamma position to the Y adjacent to V; or together Z and W are connected via an additional 3–5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl and —R⁹; or together W and W' are connected via an additional 2–5 atoms to form a cyclic group, optionally containing 0–2 heteroatoms, and V must be aryl, substituted aryl, heteroaryl, or substituted heteroaryl;

b) V², W² and W''' are independently selected from the group of —H, alkyl, aralkyl, alicyclic, aryl, substituted aryl, heteroaryl, substituted heteroaryl, 1-alkenyl, and 1-alkynyl;

Z² is selected from the group of —CHR²OH, —CHR²OC(O)R³, —CHR²OC(S)R³, —CHR²OCO₂R³, —CHR²OC(O)SR³, —CHR²OC(S)OR³, —CH(aryl)OH, —CH(CH=CR²₂)OH, —CH(C≡CR²)OH, —SR², —CH₂NHaryl, —CH₂aryl; or together V² and Z² are connected via an additional 3–5 atoms to form a cyclic group containing 5–7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —OC(O)R³, —OCO₂R³, and —OC(O)SR³;

D' is —H;

D'' is selected from the group of —H, alkyl, —OR², —OH, and —OC(O)R³;

each W³ is independently selected from the group consisting of —H, alkyl, aralkyl, alicyclic, aryl, substituted aryl, heteroaryl, substituted heteroaryl, 1-alkenyl, and 1-alkynyl;

p is an integer 2 or 3;

with the provisos that:

a) V, Z, W, W' are not all —H and V², Z², W², W''' are not all —H; and

R² is selected from the group consisting of R³ and —H;

R³ is selected from the group consisting of alkyl, aryl, alicyclic, and aralkyl;

each R⁴ is independently selected from the group consisting of —H, alkyl, -alkylenearyl, and aryl, or together R⁴ and R⁴ are connected via 2–6 atoms, optionally including one heteroatom selected from the group consisting of O, N, and S;

R$^6$ is selected from the group consisting of —H, lower alkyl, acyloxyalkyl, aryl, aralkyl, alkoxycarbonyloxyalkyl, and lower acyl, or together with R$^{12}$ is connected via 1–4 carbon atoms to form a cyclic group;

R$^7$ is lower R$^3$;

each R$^9$ is independently selected from the group consisting of —H, alkyl, aralkyl, and alicyclic, or together R$^9$ and R$^9$ form a cyclic alkyl group;

R$^{11}$ is selected from the group consisting of alkyl, aryl, —NR$^2_2$, and —OR$^2$; and each R$^{12}$ and R$^{13}$ is independently selected from the group consisting of H, lower alkyl, lower aryl, lower aralkyl, all optionally substituted, or R$^{12}$ and R$^{13}$ together are connected via a chain of 2–6 atoms, optionally including 1 heteroatom selected from the group consisting of O, N, and S, to form a cyclic group;

each R$^{14}$ is independently selected from the group consisting of —OR$^{17}$, —N(R$^{17}$)$_2$, —NHR$^{17}$, —SR$^{17}$, and —NR$^2$OR$^{20}$;

R$^{15}$ is selected from the group consisting of —H, lower aralkyl, lower aryl, lower aralkyl, or together with R$^{16}$ is connected via 2–6 atoms, optionally including 1 heteroatom selected from the group consisting of O, N, and S;

R$^{16}$ is selected from the group consisting of —(CR$^{12}$R$^{13}$)$_n$—C(O)—R$^{14}$, —H, lower alkyl, lower aryl, lower aralkyl, or together with R$^{15}$ is connected via 2–6 atoms, optionally including 1 heteroatom selected from the group consisting of O, N, and S;

each R$^{17}$ is independently selected from the group consisting of lower alkyl, lower aryl, and lower aralkyl, or together R$^{17}$ and R$^{17}$ on N is connected via 2–6 atoms, optionally including 1 heteroatom selected from the group consisting of O, N, and S;

R$^{18}$ is selected from the group consisting of —H and lower R$^3$;

R$^{19}$ is selected from the group consisting of —H, and lower acyl;

R$^{20}$ is selected from the group consisting of —H, lower R$^3$, and —C(O)-(lower R$^3$);

n is an integer from 1 to 3;

with the provisos that:

1) when X$^3$, X$^4$, or X$^5$ is N, then the respective J$^3$, J$^4$, or J$^5$ is null;

2) when L is substituted furanyl, then at least one of J$^2$, J$^3$, J$^4$, and J$^5$ is not —H or null;

3) when L is not substituted furanyl, then at least two of J$^2$, J$^3$, J$^4$, and J$^5$ on formula I(a) or J$^2$, J$^3$, J$^4$, J$^5$, and J$^6$ on formula I(b) are not —H or null;

4) when G$^2$, G$^3$, or G$^4$ is O or S, then the respective J$^2$, J$^3$, or J$^4$ is null;

5) when G$^3$ or G$^4$ is N, then the respective J$^3$ or J$^4$ is not halogen or a group directly bonded to G$^3$ or G$^4$ via a heteroatom;

6) if both Y groups are —NR$^6$—, and R$^1$ and R$^1$ are not connected to form a cyclic phosphoramidate, then at least one R$^1$ is —(CR$^{12}$R$^{13}$)—C(O)$_n$—R$^{14}$;

7) when L is -alkylcarbonylamino- or -alkylaminocarbonyl-, then X$^3$, X$^4$, and X$^5$ are not all C;

8) when L is -alkoxyalkyl-, and X$^3$, X$^4$, and X$^5$ are all C, then neither J$^3$ nor J$^5$ can be substituted with an acylated amine;

9) when R$^5$ is substituted phenyl, then J$^3$, J$^4$, and J$^5$ is not purinyl, purinylalkylene, deaza-purinyl, or deazapurinylalkylene;

10) R$^1$ can be lower alkyl only when the other YR$^1$ is —NR$^6$—C(R$^{12}$ R$^{13}$ )$_n$—C(O)—R$^{14}$;

11) when R$^5$ is substituted phenyl and L is 1,2-ethynyl, then J$^3$ or J$^5$ is not a heterocyclic group;

12) when L is 1,2-ethynyl, then X$^3$ or X$^5$ cannot be N;

and pharmaceutically acceptable prodrugs and salts thereof.

In one aspect of the present invention compounds of formula Ia are envisioned.

In one aspect of the present invention compounds of formula Ib are envisioned.

In one aspect of the present invention compounds of formula I are envisioned with the further proviso that when L is -alkoxyalkyl-, and R$^5$ is substituted thienyl, substituted furanyl, or substituted phenyl, then J$^3$, J$^4$, or J$^5$ is not halo or alkenyl.

In another aspect are compounds of formula I with the further proviso that when L is -alkoxyalkyl-, then R$^5$ is not substituted thienyl, substituted furanyl, or substituted phenyl.

In yet another aspect are compounds of formula I with the further proviso that when L is -alkoxycarbonyl-, and X$^3$, X$^4$, and X$^5$ are all C, then neither J$^2$ nor J$^6$ is a group attached through a nitrogen atom.

In another aspect are compounds of formula I with the further proviso that when L is -alkoxyalkyl- or -alkoxycarbonyl-, then R$^5$ is not substituted phenyl.

In one aspect of the invention are compounds of formula I wherein said prodrug is a compound of formula VI:

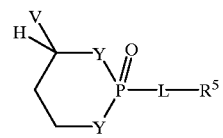

VI wherein

V is selected from the group consisting of aryl, substituted aryl, heteroaryl, and substituted heteroaryl. In another aspect are such compounds wherein V is selected from the group consisting of phenyl and substituted phenyl. In yet another aspect are such compounds wherein V is selected from the group consisting of 3,5-dichlorophenyl, 3-bromo-4-fluorophenyl, 3-chlorophenyl, 2-bromophenyl, 3-bromophenyl, and 4-pyridyl.

In one aspect of the invention are compounds of formula I wherein said prodrug is a compound of formula VII:

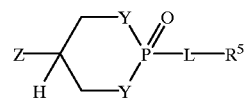

VII wherein

Z$^2$ is selected from the group consisting of —CHR$^2$OH, —CHR$^2$OC(O)R$^3$, —CHR$^2$OC(S)R$^3$, —CHR$^2$OCO$_2$R$^3$, —CHR$^2$OC(O)SR$^3$, —CHR$^2$OC(S)OR$^3$, and —CH$_2$aryl. In another aspect, are such compounds wherein Z$^2$ is selected from the group consisting of —CHR$^2$OH, —CHR$^2$OC(O) R$^3$, and —CHR$^2$OCO$_2$R$^3$. In yet another aspect are such compounds wherein R$^2$ is —H.

In another aspect of the invention are compounds of formula I wherein said prodrug is a compound of formula VIII:

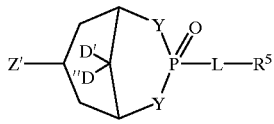

VIII wherein

Z' is selected from the group consisting of —OH, —OC(O)R³, —OCO₂ R³, and —OC(O)S R³;

D' is —H; and

D" is selected from the group consisting of —H, alkyl, —OH, and —OC(O)R³.

In another aspect of the invention are compounds wherein W' and Z are —H, W and V are both the same aryl, substituted aryl, heteroaryl, or substituted heteroaryl, and both Y groups are the same —NR⁶—, such that the phosphonate or phosphoramidate prodrug moiety:

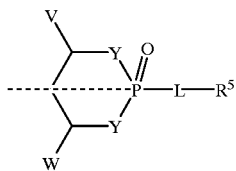

has a plane of symmetry through the phosphorus-oxygen double bond.

In one aspect of the invention are compounds of formula I wherein when Y is —O—, then R¹ attached to —O— is independently selected from the group consisting of —H, optionally substituted aryl, optionally substituted alicyclic where the cyclic moiety contains a carbonate or thiocarbonate, optionally substituted arlyalkylene-, —C(R²)₂ OC(O)R³, —C(R²)₂—O—C(O)OR³, —C(R²)₂OC(O)SR³, - alkyl-S—C(O)R³, and -alkyl-S—S-alkylhydroxy;

when Y is —NR⁶—, then R¹ attached to —NR⁶— is independently selected from the group consisting of —H, and —(CR¹²R¹³)ₙ—C(O)R¹⁴;

or when either Y is independently selected from —O— and —NR⁶—, then together R¹ and R¹ are

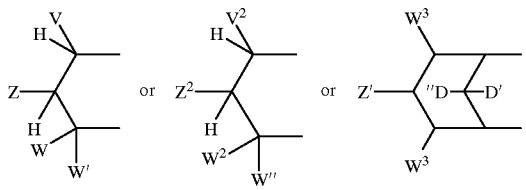

wherein a) V is selected from the group of aryl, substituted aryl, heteroaryl, substituted heteroaryl, 1-alkynyl and 1-alkenyl;

Z is selected from the group of —CHR²OH, —CHR²OC(O)R³, —CHR²OC(S)R³, —CHR²OC(S)OR³, —CHR²OC(O)SR³, —CHR²OCO₂R³, —OR², —SR², —CHR²N₃, —CH₂aryl, —CH(aryl)OH, —CH(CH=CR²₂)OH, —CH(C≡CR²)OH, —R², —NR²₂, —OCOR³, —OCO₂R³, —SCOR³, —SCO₂R³, —NHCOR², —NHCO₂R³, —CH₂NHaryl, —(CH₂)ₚ—OR¹⁹, and —(CH₂)ₚ—SR¹⁹; or together V and Z are connected via an additional 3–5 atoms to form a cyclic group, optionally containing 1 heteroatom, said cyclic group is fused to an aryl group at the beta and gamma position to the Y adjacent to V; or together Z and W are connected via an additional 3–5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl and —R⁹; or together W and W' are connected via an additional 2–5 atoms to form a cyclic group, optionally containing 0–2 heteroatoms, and V must be aryl, substituted aryl, heteroaryl, or substituted heteroaryl;

b) V², W² and W" are independently selected from the group of —H, alkyl, aralkyl, alicyclic, aryl, substituted aryl, heteroaryl, substituted heteroaryl, 1-alkenyl, and 1-alkynyl;

Z² is selected from the group of —CHR²OH, —CHR²OC(O)R³, —CHR²OC(S)R³, —CHR²OCO₂R³, —CHR²OC(O)SR³, —CHR²OC(S)OR³, —CH(aryl)OH, —CH(CH=CR²₂)OH, —CH(C≡CR²)OH, —SR², —CH₂NHaryl, —CH₂aryl; or together V² and Z² are connected via an additional 3–5 atoms to form a cyclic group containing 5–7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —OC(O)R³, —OCO₂R³, and —OC(O)SR³;

D' is —H;

D" is selected from the group of —H, alkyl, —OR², —OH, and —OC(O)R³;

each W³ is independently selected from the group consisting of —H, alkyl, aralkyl, alicyclic, aryl, substituted aryl, heteroaryl, substituted heteroaryl, 1-alkenyl, and 1-alkynyl;

p is an integer 2 or 3;

with the provisos that:

a) V, Z, W, W' are not all —H and V², Z², W², W" are not all —H; and b) both Y groups are not —NR⁶—;

R² is selected from the group consisting of R³ and —H;

R³ is selected from the group consisting of alkyl, aryl, alicyclic, and aralkyl;

R⁶ is selected from the group consisting of —H, and lower alkyl.

In another aspect of the invention are such compounds wherein when both Y groups are —O—, then R¹ is independently selected from the group consisting of optionally substituted aryl, optionally substituted benzyl, —C(R²)₂OC(O)R³, —C(R²)₂OC(O)OR³, and —H; or when Y is —NR⁶—, then the R¹ attached to said —NR⁶— group is selected from the group consisting of —C(R⁴)₂—C(O)OR³, and —C(R²)₂C(O)OR³; or the other Y group is —O— and then R¹ attached to said —O— is selected from the group consisting of optionally substituted aryl, —C(R²)₂OC(O)R³, and —C(R²)₂OC(O)OR³. Within such group are compounds wherein both Y groups are —O—, and R¹ is H.

In another aspect of the invention are compounds wherein at least one Y is —O—, and together R¹ and R¹ are

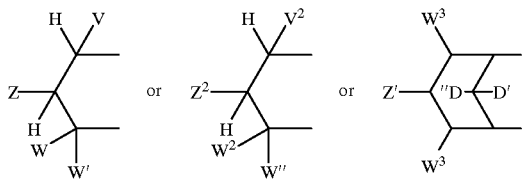

wherein
a) V is selected from the group of aryl, substituted aryl, heteroaryl, substituted heteroaryl, 1-alkynyl and 1-alkenyl;

Z is selected from the group of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2$$_2$)OH, —CH(C≡CR$^2$)OH, —R$^2$, —NR$^2$$_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^{19}$, and —(CH$_2$)$_p$—SR$^{19}$; or together V and Z are connected via an additional 3–5 atoms to form a cyclic group, optionally containing 1 heteroatom, said cyclic group is fused to an aryl group at the beta and gamma position to the Y adjacent to V; or together Z and W are connected via an additional 3–5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl and —R$^9$; or together W and W' are connected via an additional 2–5 atoms to form a cyclic group, optionally containing 0–2 heteroatoms, and V must be aryl, substituted aryl, heteroaryl, or substituted heteroaryl;

b) V$^2$, W$^2$ and W" are independently selected from the group of —H, alkyl, aralkyl, alicyclic, aryl, substituted aryl, heteroaryl, substituted heteroaryl, 1-alkenyl, and 1-alkynyl;

Z$^2$ is selected from the group of —CHR$^2$OH, —CHR$^2$OC(O)R$^3$, —CHR$^2$OC(S)R$^3$, —CHR$^2$OCO$_2$R$^3$, —CHR$^2$OC(O)SR$^3$, —CHR$^2$OC(S)OR$^3$, —CH(aryl)OH, —CH(CH=CR$^2$$_2$)OH, —CH(C≡CR$^2$)OH, —SR$^2$, —CH$_2$NHaryl, —CH$_2$aryl; or together V$^2$ and Z$^2$ are connected via an additional 3–5 atoms to form a cyclic group containing 5–7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —OC(O)R$^3$, —OCO$_2$R$^3$, and —OC(O)SR;

D' is —H;

D" is selected from the group of —H, alkyl, —OR$^2$, —OH, and —OC(O)R$^3$;

each W$^3$ is independently selected from the group consisting of —H, alkyl, aralkyl, alicyclic, aryl, substituted aryl, heteroaryl, substituted heteroaryl, 1-alkenyl, and 1-alkynyl;

p is an integer 2 or 3; with the provisos that:
a) V, Z, W, W' are not all —H and V$^2$, Z$^2$, W$^2$, W" are not all —H; and
b) both Y groups are not —NR$^6$—;

R$^2$ is selected from the group consisting of R$^3$ and —H;
R$^3$ is selected from the group consisting of alkyl, aryl, alicyclic, and aralkyl;
R$^6$ is selected from the group consisting of —H, and lower alkyl.

In another aspect of the invention are compounds wherein one Y is —O—, and R$^1$ is optionally substituted aryl; and the other Y is —NR$^6$—, where R$^1$ attached to said —NR$^6$— is selected from the group consisting of —C(R$^4$)$_2$C(O)OR$^3$, and —C(R$^2$)$_2$C(O)OR$^3$. In another aspect are such compounds wherein R$^1$ attached to —O— is selected from the group consisting of phenyl, and phenyl substituted with 1–2 substituents selected from the group consisting of —NHC(O)CH$_3$, —F, —Cl, —Br, —C(O)OCH$_2$CH$_3$, and —CH$_3$; and wherein R$^1$ attached to —NR$^6$— is —C(R$^2$)$_2$C(O)OR$^3$; each R$^2$ is independently selected from the group consisting of —CH$_3$, —CH$_2$CH$_3$, and —H. Within such a group are compounds wherein the substituents of said substituted phenyl are selected from the group consisting of 4-NHC(O)CH$_3$, —Cl, —Br, 2-C(O)OCH$_2$CH$_3$, and —CH$_3$.

In another aspect of the invention are compounds of formula I wherein

J$^2$, J$^3$, J$^4$, J$^5$, and J$^6$ are independently selected from the group consisting of —H, —NR$^4$$_2$, —CONR$^4$$_2$, —CO$_2$R$^3$, halo, —SO$_2$NR$^4$$_2$, lower alkyl, lower alkenyl, lower alkylaryl, lower alkynyl, lower perhaloalkyl, lower haloalkyl, lower aryl, lower alkylene-OH, —OR$^{11}$, —CR$^2$$_2$NR$^4$$_2$, —CN, —C(S)NR$^4$$_2$, —OR$^2$, —SR$^2$, —N$_3$, —NO$_2$, —NHC(S)NR$^4$$_2$, —NR$^{18}$COR$^2$, —CR$^2$$_2$CN;

L is selected from the group consisting of
i) 2,5-furanyl, 2,5-thienyl, 1,3-phenyl, 2,6-pyridyl, 2,5-oxazolyl, 5,2-oxazolyl, 2,4-oxazolyl, 4,2-oxazolyl, 2,4-imidazolyl, 2,6-pyrimidinyl, 2,6-pyrazinyl;
ii) 1,2-ethynyl; and
iii) a linking group having 3 atoms measured by the fewest number of atoms connecting the carbon of the aromatic ring and the phosphorus atom and is selected from the group consisting of alkylcarbonylamino-, -alkylaminocarbonyl-, -alkoxycarbonyl-, and -alkoxyalkyl-;

when both Y groups are —O—, then R$^1$ is independently selected from the group consisting of optionally substituted aryl, optionally substituted benzyl, —C(R$^2$)$_2$OC(O)R$^3$, —C(R$^2$)$_2$OC(O)OR$^3$, and —H; or when one Y is —O—, then R$^1$ attached to —O— is optionally substituted aryl; and the other Y is —NR$^6$—, then R$^1$ attached to —NR$^6$—is selected from the group consisting of —C(R$^4$)$_2$C(O)OR$^3$, and —C(R$^2$)$_2$C(O)OR$^3$; or when Y is —O— or —NR$^6$—, then together R$^1$ and R$^1$ are

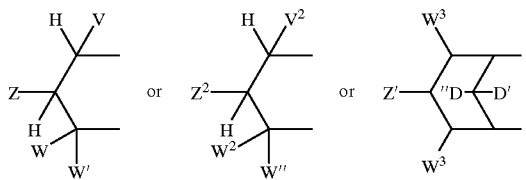

wherein
a) V is selected from the group of aryl, substituted aryl, heteroaryl, substituted heteroaryl, 1-alkynyl and 1-alkenyl;

Z is selected from the group of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2$$_2$)OH, —CH(C≡CR$^2$)OH, —R, —NR$^2$$_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^{19}$, and —(CH$_2$)$_p$—SR$^{19}$; or together V and Z are connected via an additional 3–5 atoms to form a cyclic group, optionally containing 1 heteroatom, said cyclic group is fused to an aryl group at the beta and gamma position to the Y adjacent to V; or together Z and W are connected via an additional 3–5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl and —R⁹; or together W and W' are connected via an additional 2–5 atoms to form a cyclic group, optionally containing 0–2 heteroatoms, and V must be aryl, substituted aryl, heteroaryl, or substituted heteroaryl;

b) V², W² and W" are independently selected from the group of —H, alkyl, aralkyl, alicyclic, aryl, substituted aryl, heteroaryl, substituted heteroaryl, 1-alkenyl, and 1-alkynyl;

Z² is selected from the group of —CHR²OH, —CHR²OC(O)R³, —CHR²OC(S)R³, —CHR²OCO₂R³, —CHR²OC(O)SR³, —CHR²OC(S)OR³, —CH(aryl)OH, —CH(CH=CR²₂)OH, —CH(C≡CR²)OH, —SR², —CH₂NHaryl, —CH₂aryl; or together V² and Z² are connected via an additional 3–5 atoms to form a cyclic group containing 5–7 ring atoms, optionally containing 1 heteroatom, and substituted with hydroxy, acyloxy, alkoxycarbonyloxy, or aryloxycarbonyloxy attached to a carbon atom that is three atoms from a Y attached to phosphorus;

c) Z' is selected from the group of —OH, —OC(O)R³, —OCO₂R³, and —OC(O)SR³;

D' is —H;

D" is selected from the group of —H, alkyl, —OR², —OH, and —OC(O)R³;

each W³ is independently selected from the group consisting of —H, alkyl, aralkyl, alicyclic, aryl, substituted aryl, heteroaryl, substituted heteroaryl, 1-alkenyl, and 1-alkynyl;

p is an integer 2 or 3;

with the provisos that:

a) V, Z, W, W' are not all —H and V², Z², W², W" are not all —H; and b) both Y groups are not —NR⁶—;

R² is selected from the group consisting of R³ and —H;

R³ is selected from the group consisting of alkyl, aryl, alicyclic, and aralkyl;

R⁶ is selected from the group consisting of —H, and lower alkyl.

In another aspect, R⁵ is substituted phenyl;

L is furan-2,5-diyl; J², J³, J⁴, J⁵, and J⁶ are independently selected from the group consisting of —OR³, —SO₂NHR⁷, —CN, —H, halo, —NR⁴₂, —(CH₂)₂aryl, —(CH₂)NH-aryl and —NO₂; at least one Y group is —O—; and pharmaceutically acceptable salts and prodrugs thereof.

In another aspect of the invention are such compounds wherein when Y is —O—, then R¹ attached to —O— is independently selected from the group consisting of —H, optionally substituted phenyl, —CH₂OC(O)—tBu, —CH₂OC(O)OEt, and —CH₂OC(O)OiPr;

when Y is —NR⁶—, then R¹ is attached to —NR⁶— independently selected from the group consisting of —C(R²)₂C(O)OR³, —C(R⁴)₂C(O)OR³, or when Y is —O— or —NR⁶—, and at least one Y is —O—, then together R¹ and R¹ are

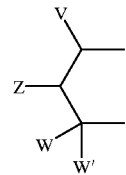

wherein

V is selected from the group consisting of optionally substituted aryl, and optionally substituted heteroaryl; and Z, W', and W are H; and R⁶ is selected from the group consisting of —H, and lower alkyl.

In one aspect of the invention are compounds wherein both Y groups are —O— and R¹ is —H. In another aspect are compounds of claim 45 wherein both Y groups are —O—, and R¹ is —CH₂OC(O)OEt. In yet another aspect are compounds are such wherein both Y groups are —O—, and R¹ and R¹ together are

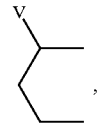

and V is phenyl substituted with 1–3 halogens. Within such a group are compounds wherein V is selected from the group consisting of 3,5-dichlorophenyl, 3-bromo-4-fluorophenyl, 3-chlorophenyl, 2-bromophenyl, and 3-bromophenyl.

In one aspect of the invention are such compounds wherein n is 1, and the carbon attached to R¹² and R¹³ has S stereochemistry.

In another aspect of the invention are compounds wherein R¹⁵ is not H.

In yet another aspect of the invention are compounds of formula I wherein —NR¹⁵R¹⁶ is a cyclic amine. Within such a group are compounds wherein —NR¹⁵R¹⁶ is selected from the group consisting of morpholinyl and pyrrolidinyl. In another aspect of the invention, R¹⁶ groups include —(CR¹²R¹³)ₙ—C(O)—R¹⁴. In yet another aspect are compounds with the formula

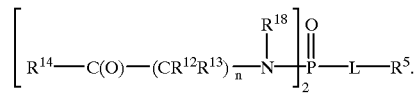

Within such a group are compounds wherein n is 1. In one aspect of the invention compounds are envisioned wherein when R¹² and R¹³ are not the same, then R¹⁴—C(O)—CR¹²R¹³—NH₂ is an ester or thioester of a naturally occurring amino acid; and R¹⁴ is selected from the group consisting of —OR¹⁷ and —SR¹⁷.

In one aspect of the invention are compounds wherein one Y is —O— and its corresponding R¹ is optionally substituted phenyl, while the other Y is —NH—, and its corresponding R¹ is —C(R²)₂—COOR³. When R¹ is —CHR³COOR³, then the corresponding —NR⁶— *CHR³COOR³, generally has L stereochemistry.

In general, substituents V, Z, W, W', V², Z², W², W", Z', D', D", and W³ of formula I are chosen such that they exhibit one or more of the following properties:

(1) enhance the oxidation reaction since this reaction is likely to be the rate determining step and therefore must compete with drug elimination processes.

(2) enhance stability in aqueous solution and in the presence of other non-p450 enzymes;

(3) enhance cell penetration, e.g. substituents are not charged or of high molecular weight since both properties can limit oral bioavailability as well as cell penetration;

(4) promote the β-elimination reaction following the initial oxidation by producing ring-opened products that have one or more of the following properties:
 a) fail to recyclize;
 b) undergo limited covalent hydration;
 c) promote β-elimination by assisting in the proton abstraction;
 d) impede addition reactions that form stable adducts, e.g. thiols to the initial hydroxylated product or nucleophilic addition to the carbonyl generated after ring opening; and
 e) limit metabolism of reaction intermediates (e.g. ring-opened ketone);

(5) lead to a non-toxic and non-mutagenic by-product with one or more of the following characteristics. Both properties can be minimized by using substituents that limit Michael additions, reactions, e.g.
 a) electron donating Z groups that decrease double bond polarization;
 b) W groups that sterically block nucleophilic addition to β-carbon;
 c) Z groups that eliminate the double bond after the elimination reaction either through retautomerization (enol->keto) or hydrolysis (e.g. enamine);
 d) V groups that contain groups that add to the α,β-unsaturated ketone to form a ring;
 e) Z groups that form a stable ring via Michael addition to double bond; and
 f) groups that enhance detoxification of the by-product by one or more of the following characteristics:
  (i) confine to liver; and
  (ii) make susceptible to detoxification reactions (e.g. ketone reduction); and (6) capable of generating a pharmacologically active product.

In one aspect of the invention, V groups of formula VI are aryl, substituted aryl, heteroaryl, and substituted heteroaryl. Within such a group aryl and substituted aryl groups include phenyl, and phenyl substituted with 1–3 halogens. Within such a group are 3,5-dichlorophenyl, 3-bromo-4-fluorophenyl, 3-chlorophenyl, 2-bromophenyl, and 3-bromophenyl. In another aspect of the invention, Y is —O—. In yet another aspect of the invention V is selected from the group consisting of monocyclic heteroaryl and monocyclic substituted heteroaryl containing at least one nitrogen atom. Within such a group such a heteroaryl and substituted heteroaryl is 4-pyridyl and 3-bromopyridyl, respectively.

In yet another aspect of the invention, when together V and Z are connected via an additional 3–5 atoms to form a cyclic group, optionally containing 1 heteroatom, said cyclic group is fused to an aryl group at the beta and gamma positions to the Y attached to phosphorus. In such compounds it is envisioned that said aryl group may be an optionally substituted monocyclic aryl group and the connection between Z and the gamma position of the aryl group is selected from the group consisting of O, $CH_2$, $CH_2CH_2$, $OCH_2$ or $CH_2O$.

In another aspect, together V and W are connected via an additional 3 carbon atoms to form an optionally substituted cyclic group containing 6 carbon atoms and monosubstituted with one substituent selected from the group consisting of hydroxy, acyloxy, alkoxycarbonyloxy, alkylthiocarbonyloxy, and aryloxycarbonyloxy attached to one of said additional carbon atoms that is three atoms from a Y attached to the phosphorus. In such compounds, it is envisioned that together V and W may form a cyclic group selected from the group consisting of —$CH_2$—CH(OH)—$CH_2$—, $CH_2$CH($OCOR^3$)—$CH_2$—, and —$CH_2$CH($OCO_2R^3$)—$CH_2$—.

In another aspect, V group is 1-alkene. Oxidation by p450 enzymes is known to occur at benzylic and allylic carbons.

In yet another aspect of the invention, prodrugs of formula VI are:

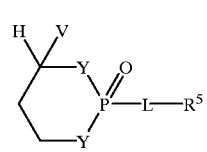

VI wherein

V is selected from the group consisting of aryl, substituted aryl, heteroaryl, and substituted heteroaryl, 1-alkenyl, and 1-alkynyl. In another aspect V groups of formula VI are aryl, substituted, heteroaryl, and substituted heteroaryl. Within such a group aryl and substituted aryl groups include phenyl and substituted phenyl. Within such a group heteroaryl groups include monocyclic substituted and unsubstituted heteroaryl groups. Such heteroaryls include 4-pyridyl and 3-bromopyridyl. In another aspect of the invention, y is —O—.

In one aspect, the compounds of formula I have a group Z which is —H, alkyl, alicyclic, hydroxy, alkoxy,

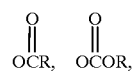

or —NHCOR. Within such a group are compounds in which Z decreases the propensity of the byproduct, vinyl aryl ketone to undergo Michael additions. Such Z groups are groups that donate electrons to the vinyl group which is a known strategy for decreasing the propensity of α,β-unsaturated carbonyl compounds to undergo a Michael addition. For example, a methyl group in a similar position on acrylamide results in no mutagenic activity whereas the unsubstituted vinyl analog is highly mutagenic. Other groups could serve a similar function, e.g. Z=OR, NHAc, etc. Other groups may also prevent the Michael addition especially groups that result in removal of the double bond altogether such as Z=OH, —OC(O)R, —$OCO_2R$, and $NH_2$, which will rapidly undergo retautomerization after the elimination reaction. Certain W and W' groups are also advantageous in this role since the group(s) impede the addition reaction to the β-carbon or destabilize the product. Another suitable Z group is one that contains a nucleophilic group capable of adding to the α,β-unsaturated double bond after the elimination reaction i.e. $(CH_2)_p$—SH or $(CH_2)_p$—OH where p is 2 or 3. Yet another suitable group is a group attached to V which is capable of adding to the α,β-unsaturated double bond after the elimination reaction:

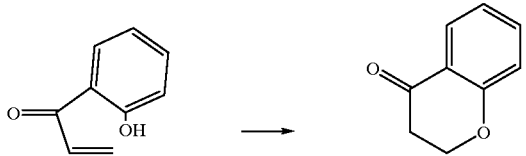

In another aspect of the invention are prodrugs of formula VII:

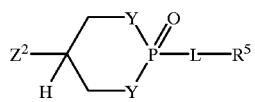

VII wherein
Z² is selected from the group consisting of —CHR²OH, —CHR²OCOR³, —CHR²OC(S)R³, —CHR²OCO₂R³, —CHR²OC(O)SR³, and —CHR²OC(S)OR³. Within such a group, Z² may be selected from the group of —CHR²OH, —CHR²OC(O)R³, and —CHR²OCO₂R³. In one aspect of the invention, Y is —O—.

In another aspect of the invention are prodrugs of formula VIII:

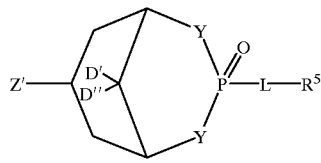

VIII wherein
Z' is selected from the group consisting of —OH, —OC(O)R³, —OCO₂R³, and —OC(O)SR³;
D' is —H; and
D" is selected from the group consisting of —H, alkyl, —OR², —OH, and —OC(O)R³. In one aspect of the invention Y is —O—.

In one embodiment, W' and Z are —H, W and V are both the same aryl, substituted aryl, heteroaryl, or substituted heteroaryl such that the phosphonate prodrug moiety:

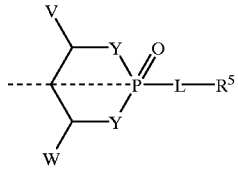

has a plane of symmetry. In one aspect of the invention Y is —O—.

In one aspect, oral bioavailability is at least 5%. In another aspect, oral bioavailability is at least 10%.

p450 oxidation can be sensitive to stereochemistry which might either be at phosphorus or at the carbon bearing the aromatic group. The prodrugs of the present invention have two isomeric forms around the phosphorus. One aspect of the invention is the stereochemistry that enables both oxidation and the elimination reaction. Within such a group are the compounds where V is trans to the phosphorous-oxygen double bond.

It is envisioned that compounds of formula VIII may utilize a Z' group that is capable of undergoing an oxidative reaction that yields an unstable intermediate which via elimination reactions breaks down to the corresponding $P(O)(O^-)_2$—L—$R^5$, $P(O)(NHR^6)_2$—$R^5$, or $P(O)(O^-)(NHR^6)$—L—$R^5$. Within such a group, the Z' group is OH. Group D" may be hydrogen, alkyl, and —OR², —OC(O)R³.

With regard to the foregoing aspect of the invention, the inventors contemplate any combination of the Markush groups as set forth above and the sub-Markush groups for any variable as described in the following Tables A–Q.

TABLE A

Table of Sub-Markush Groups for the Variable $R^1$

| Sub-Markush Group | $R^1$ |
|---|---|
| 1 | optionally substituted aryl, optionally substituted benzyl, —C(R²)₂OC(O)R³, —C(R²)₂O—C(O)OR³ and —H |
| 2 | optionally substituted aryl, —C(R²)₂OC(O)R³, and —C(R²)₂O—C(O)OR³ |
| 3 | aryl and —C(R²)₂-aryl |
| 4 | -alkylene-S—S-alkylene-hydroxyl, -alkylene-S—C(O)R³ and -alkylene-S—S—S-alkylenehydroxy or together $R^1$ and $R^1$ alkylene-S—S-alkylene to form a cyclic group |
| 5 | —H |
| 6 | —C(R²)₂C(O)OR³ |
| 7 | —C(R⁴)₂—C(O)OR³, —C(R²)₂C(O)OR³ |
| 8 | —C(R²)₂OC(O)R³, —C(R²)₂OC(O)OR³ |
| 9 | optionally substituted aryl, |
| 10 | together $R^1$ and $R^1$ are alkyl-S—S-alkyl- to form a cyclic group |
| 11 | optionally substituted phenyl, —CH₂OC(O)-t-Bu, —CH₂OC(O)OEt, —CH₂OC(O)O-iPr, and H |
| 12 | H, optionally substituted aryl, optionally substituted alicyclic where the cyclic moiety contains a carbonate or thiocarbonate, optionally substituted -alkylenearyl, —C(R²)₂OC(O)R³, —C(R²)₂—O—C(O)OR³, —C(R²)₂OC(O)SR³, -alkylene-S—C(O)R³, and -alkylene-S—S-alkylenehydroxy |

TABLE A-continued

Table of Sub-Markush Groups for the Variable $R^1$

| Sub-Markush Group | $R^1$ |
|---|---|
| 13 | H and —$(CR^{12}R^{13})_n$—$C(O)R^{14}$ |
| 14 | 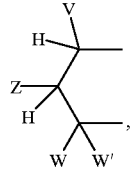 |
| 15 | 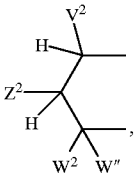 |
| 16 | 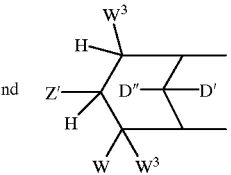 |
| 17 | 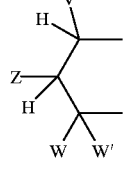 |
| 18 | —$(CR^{12}R^{13})_n$—$C(O)R^{14}$ |
| 19 | $R^1$ is selected from the group consisting of phenyl, and phenyl substituted with 1–2 substituents selected from the group consisting of —NHC(O)CH$_3$, —F, —Cl, —Br, —C(O)OCH$_2$CH$_3$, and —CH$_3$ |
| 20 | $R^1$ attached to —NR$^6$— is —C(R$^2$)$_2$C(O)OR$^3$, and each $R^2$ is independently selected from the group consisting of —CH$_3$, —CH$_2$CH$_3$, and —H |
| 21 | phenyl substituted with 1–2 substituents selected from the group of 4-NHC(O)CH$_3$, —Cl, —Br, 2-C(O)OCH$_2$CH$_3$ and —CH$_3$. |
| 22 | substituted phenyl |
| 23 | —CH$_2$OC(O)OEt |
| 24 | , where V is phenyl substituted with 1–3 halogens |

TABLE B

Table of Sub-Markush Groups for the Variable $R^4$

| Sub-Markush Group | $R^4$ |
|---|---|
| 1 | —H, lower alkyl and lower aryl |
| 2 | —H, C1–C4 alkyl |
| 3 | H |
| 4 | substituted phenyl |
| 5 | 4-hydroxy phenyl |

TABLE B-continued

Table of Sub-Markush Groups for the Variable $R^4$

| Sub-Markush Group | $R^4$ |
|---|---|
| 6 | together $R^4$ and $R^4$ are connected via 2–5 atoms, optionally including one heteroatom selected from the group of O, N and S |
| 7 | together $R^4$ and $R^4$ are connected via 2–5 atoms, optionally including one O |

TABLE C

Table of Sub-Markush Groups for the Variable $R^{12}$

| Sub-Markush Group | $R^{12}$ |
|---|---|
| 1 | —H, methyl, ethyl, n-propyl, i-propyl, n-butyl, i-butyl, —CH$_2$CH$_2$—SCH$_3$, phenyl, and benzyl |
| 2 | —H, methyl, i-propyl, i-butyl, and benzyl |
| 3 | —H, methyl, i-propyl and benzyl |
| 4 | -methyl |
| 5 | —H |
| 6 | together $R^{12}$ and $R^{13}$ are connected via 2–5 carbon atoms to form a cycloalkyl group |
| 7 | together $R^{12}$ and $R^{13}$ are connected via 4 carbon atoms to form a cyclopentyl group |
| 8 | not the same as $R^{13}$, and $R^{14}$—C(O)—CR$^{12}$R$^{13}$—NH$_2$ is an ester or thioester of a naturally occurring amino acid, and $R^{14}$ is selected from the group of OR$^{17}$ and SR$^{17}$ |

TABLE D

Table of Sub-Markush Groups for the Variable $R^{13}$

| Sub-Markush Group | $R^{13}$ |
|---|---|
| 1 | —H, methyl, ethyl, n-propyl, i-propyl, n-butyl, i-butyl, —CH$_2$CH$_2$—SCH$_3$, phenyl, and benzyl |
| 2 | —H, methyl, i-propyl, i-butyl, and benzyl |
| 3 | —H, methyl, i-propyl and benzyl |
| 4 | methyl, i-propyl and benzyl |
| 5 | -methyl |
| 6 | —H |
| 7 | together $R^{12}$ and $R^{13}$ are connected via 2–5 carbon atoms to form a cycloalkyl group |
| 8 | together $R^{12}$ and $R^{13}$ are connected via 4 carbon atoms to form a cyclopentyl group |
| 9 | not the same as $R^{12}$, and $R^{14}$—C(O)—CR$^{12}$R$^{13}$—NH$_2$ is an ester or thioester of a naturally occurring amino acid, and $R^{14}$ is selected from the group of OR$^{17}$ and SR$^{17}$ |

TABLE E

Table of Sub-Markush Groups for the Variable $R^{15}$

| Sub-Markush Group | $R^{15}$ |
|---|---|
| 1 | lower alkyl and lower aralkyl |
| 2 | C1–C6 alkyl |
| 3 | methyl, ethyl and propyl |
| 4 | together $R^{15}$ and $R^{16}$ are connected via 2–6 atoms, optionally including 1 heteroatom selected from the group consisting of O, N and S |
| 5 | together $R^{15}$ and $R^{16}$ are connected via 2–6 atoms, optionally including 1 heteroatom selected from the group consisting of O and N |

TABLE F

Table of Sub-Markush Groups for the Variable $R^{16}$

| Sub-Markush Group | $R^{16}$ |
|---|---|
| 1 | lower alkyl and lower aralkyl |
| 2 | C1–C6 alkyl |
| 3 | C1–C3 alkyl |
| 4 | together $R^{15}$ and $R^{16}$ are connected via 2–6 atoms, optionally including 1 heteroatom selected from the group consisting of O, N and S |
| 5 | together $R^{15}$ and $R^{16}$ are connected via 2–6 atoms, optionally including 1 heteroatom selected from the group consisting of O and N |
| 6 | lower alkyl |

TABLE G

Table of Sub-Markush Groups for the L Variable

| Sub-Markush Group | L |
|---|---|
| 1 | 2,5-furanyl, 2,5-thienyl, 2,6-pyridyl, 2,5-oxazolyl, 5,2-oxazolyl, 2,4-oxazolyl, 4,2-oxazolyl, 2,4-imidazolyl, 2,6-pyrimidinyl, 2,6-pyrazinyl, and 1,3-phenyl |
| 2 | 2,5-furanyl, 2,6-pyridyl, 2,5-oxazolyl, 2,4-imidazolyl, and 1,3-phenyl |
| 3 | 2,5-furanyl, methyleneoxycarbonyl, methyleneoxymethylene, and methylene-aminocarbonyl |
| 4 | 2,5-furanyl |
| 5 | 1,2-ethynyl |
| 6 | -alkylenecarbonylamino-, -alkyleneaminocarbonyl-, -alkyleneoxycarbonyl-, and -alkyleneoxyalkylene |
| 7 | -methylenecarbonylamino-, -methyleneaminocarbonyl-, -methyleneoxycarbonyl-, and -methyleneoxymethylene |
| 8 | alkyleneoxyalkylene |
| 9 | alkyleneoxycarbonyl |
| 10 | alkyleneoxyalkylene and alkyleneoxycarbonyl |

TABLE H

Table of Sub-Markush Groups for the V Variable

| Sub-Markush Group | V |
|---|---|
| 1 | —H, alkyl, aralkyl, alicyclic, aryl, substituted aryl, heteroaryl, substituted heteroaryl, 1-alkenyl, and 1-alkynyl |
| 2 | aryl, substituted aryl, heteroaryl, substituted heteroaryl, 1-alkynyl and 1-alkenyl |
| 3 | aryl, substituted aryl, heteroaryl, and substituted heteroaryl, |
| 4 | aryl and substituted aryl |
| 5 | heteroaryl and substituted heteroaryl |
| 6 | optionally substituted monocyclic heteroaryl containing at least one nitrogen atom |
| 7 | phenyl and substituted phenyl |
| 8 | 3,5-dichlorophenyl, 3-bromo-4-fluorophenyl, 3-chlorophenyl, 2-bromophenyl, 3,5-difluorophenyl and 3-bromophenyl, and this group is trans to the phophorus-oxygen double bond |
| 9 | 3,5-dichlorophenyl, 3-bromo-4-fluorophenyl, 3-chlorophenyl, 2-bromophenyl, 3,5-difluorophenyl, phenyl and 3-bromophenyl |
| 10 | 3,5-dichlorophenyl, 3-bromo-4-fluorophenyl, 3-chlorophenyl, 3,5-difluorophenyl, and 3-bromophenyl |
| 11 | 4-pyridyl |
| 12 | —H |
| 13 | together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a Y attached to the phosphorus |
| 14 | together V and W are connected via an additional 3 carbon atoms to form a cyclic substituted group containing 6 carbon atoms and mono-substituted with a substituent selected from the group consisting of hydroxyl, acyloxy, alkoxycarbonyloxy, alkylthiocarbonyloxy, and aryloxycarbonyloxy, attached to one of said additional carbon atoms that is three atoms from a Y attached to the phosphorus |
| 15 | together V and W form a cyclic group selected from the group of —CH$_2$—CH(OH)—CH$_2$—, —CH$_2$CH—(OCOR$^3$)—CH$_2$— and —CH$_2$CH—(OCO$_2$R$^3$)—CH$_2$— |
| 16 | together V and Z are connected via an additional 3–5 atoms, optionally including 1 heteroatom, to form a cyclic group that is fused to an aryl group at the beta and gamma position to the Y group |
| 17 | together V and Z are connected via an additional 3–5 atoms, optionally including 1 heteroatom, to form a cyclic group that is fused to an aryl group at the beta and gamma position to the Y group, and the aryl group is an optionally substituted monocyclic aryl group and the connection between Z and the aryl group is selected from the group consisting of —O, —CH$_2$CH$_2$, —OCH$_2$ and —CH$_2$O |
| 18 | same aryl, substituted aryl, heteroaryl or substituted heteroaryl as W, and V is cis to W |
| 19 | optionally substituted aryl and optionally substituted heteroaryl |

TABLE I

Table of Sub-Markush Groups for the Variable V$^2$

| Sub-Markush Group | V$^2$ |
|---|---|
| 1 | —H, alkyl, aralkyl, alicyclic, aryl, substituted aryl, heteroaryl, substituted heteroaryl, 1-alkenyl, and 1-alkynyl |
| 2 | H, alkyl, alicyclic, aralkyl, aryl, substituted aryl, heteroaryl, and substituted heteroaryl |
| 3 | aryl, substituted aryl, heteroaryl, and substituted heteroaryl |
| 4 | aryl and substituted aryl |
| 5 | heteroaryl, substituted heteroaryl |
| 6 | optionally substituted monocyclic heteroaryl containing at least one nitrogen atom |
| 7 | phenyl and substituted phenyl |
| 8 | 3,5-dichloro-phenyl, 3-bromo-4-fluorophenyl, 3-chloro-phenyl, 3-bromo-phenyl, 2-bromorphenyl and 3,5-difluoro-phenyl |
| 9 | 4-pyridyl |
| 10 | together V$^2$ and W$^2$ are connected via an additional 3 carbon atoms to form an optionally substituted cyclic group containing 6 carbon atoms and substituted with one substituent selected from the group consisting of hydroxy, acyloxy, alkoxycarbonyl-oxy, alkylthio-carbonyloxy, and aryloxy-carbonyloxy, attached to one of said additional carbon atoms that is three atoms from a Y attached to the phosphorus |

TABLE I-continued

Table of Sub-Markush Groups for the Variable $V^2$

| Sub-Markush Group | $V^2$ |
|---|---|
| 11 | together $V^2$ and $W^2$ are connected via an additional 3 carbon atoms to form a cyclic substituted group containing 6 carbon atoms and mono-substituted with a substituent selected from the group consisting of hydroxyl, acyloxy, alkoxycarbonyl-oxy, alkylthio-carbonyloxy, and aryloxy-carbonyloxy, attached to one of said additional carbon atoms that is three atoms from a Y attached to the phosphorus |
| 12 | together $V^2$ and $W^2$ form a cyclic group selected from the group of —$CH_2$—$CH(OH)$—$CH_2$—, —$CH_2CH$—$(OCOR^3)$—$CH_2$— and —$CH_2CH$—$(OCO_2R^3)$—$CH_2$— |
| 13 | together $V^2$ and $Z^2$ are connected via an additional 3–5 atoms to form a cyclic group containing 5–7 ring atoms, optionally containing 1 heteroatom, and substituted with hydroxy, acylocy, alkoxy carbonyloxy, oraryloxycarbon yloxy attached to a carbon atom that is three atoms from a Y attached to phosphorus |
| 14 | —H |

TABLE J

Table of Sub-Markush Groups for the W Variable

| Sub-Markush Group | W |
|---|---|
| 1 | —H, alkyl, aralkyl, alicyclic, aryl, substituted aryl, heteroaryl, substituted heteroaryl, 1-alkenyl, and 1-alkynyl |
| 2 | —H, alkyl, aralkyl, alicyclic, aryl, substituted aryl, heteroaryl, substituted heteroaryl |
| 3 | —H, —$R^3$, aryl, substituted aryl, heteroaryl, and substituted heteroaryl |
| 4 | aryl, substituted aryl, heteroaryl and substituted heteroaryl |
| 5 | same as W' |
| 6 | —H |
| 7 | together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthio-carbonyloxy, and aryloxy-carbonyloxy, attached to one of said additional carbon atoms that is three atoms from a Y attached to the phosphorus |
| 8 | together V and W are connected via an additional 3 carbon atoms to form a cyclic substituted group containing 6 carbon atoms and mono-substituted with a substituent selected from the group consisting of hydroxyl, acyloxy, alkoxycarbonyl-oxy, alkylthio-carbonyloxy, and aryloxy-carbonyloxy, attached to one of said additional carbon atoms that is three atoms from a Y attached to the phosphorus |
| 9 | together V and W form a cyclic group selected from the group of —$CH_2$—$CH(OH)$—$CH_2$—, —$CH_2CH$—$(OCOR^3)CH_2$—, and —$CH_2CH$—$(OCO_2R^3)$—$CH_2$— |
| 10 | together V and W form a cyclic group selected from the group of —$CH_2$—$CH(OH)$—$CH_2$—, —$CH_2CH$—$(OCOR^3)$—$CH_2$— and —$CH_2CH$—$(OCO_2R^3)$—$CH_2$— |
| 11 | together W and W' are connected via an additional 2–5 atoms to form a cyclic group, optionally containing 0–2 heteroatoms, and V is aryl, substituted aryl heteroaryl or substituted heteroaryl |
| 12 | same aryl, substituted aryl, heteroaryl or substituted heteroaryl as V, and W is cis to V |

TABLE K

Table of Sub-Markush Groups for the W' Variable

| Sub-Markush Group | W' |
|---|---|
| 1 | —H, alkyl, aralkyl, alicyclic, aryl, substituted aryl, heteroaryl, substituted heteroaryl, 1-alkenyl, and 1-alkynyl |
| 2 | —H, alkyl, aralkyl, alicyclic, aryl, substituted aryl, heteroaryl, substituted heteroaryl |
| 3 | —H, —$R^3$, aryl, substituted aryl, heteroaryl, and substituted heteroaryl |
| 4 | same as W |
| 5 | —H |
| 6 | together W and W' are connected via an additional 2–5 atoms to form a cyclic group, optionally containing 0–2 heteroatoms, and V is aryl, substituted aryl, heteroaryl or substituted heteroaryl |

TABLE L

Table of Sub-Markush Groups for the $W^2$ Variable

| Sub-Markush Group | $W^2$ |
|---|---|
| 1 | —H, alkyl, aralkyl, alicyclic, aryl, substituted aryl, heteroaryl, substituted heteroaryl, 1-alkenyl, and 1-alkynyl |
| 2 | —H, alkyl, aralkyl, alicyclic, aryl, substituted aryl, heteroaryl, substituted heteroaryl |
| 3 | —H, —$R^3$, aryl, substituted aryl, heteroaryl, and substituted heteroaryl |
| 4 | aryl, substituted aryl, heteroaryl and substituted heteroaryl |
| 5 | same as W" |
| 6 | —H |
| 7 | together $V^2$ and $W^2$ are connected via an additional 3 carbon atoms to form an optionally substituted cyclic group containing 6 carbon atoms and substituted with one substituent selected from the group consisting of hydroxy, acyloxy, alkoxycarbonyloxy, alkylthio-carbonyloxy, and aryloxy-carbonyloxy, attached to one of said additional carbon atoms that is three atoms from a Y attached to the phosphorus |
| 8 | together $V^2$ and $W^2$ are connected via an additional 3 carbon atoms to form a cyclic substituted group containing 6 carbon atoms and mono-substituted with a substituent selected from the group consisting of hydroxyl, acyloxy, alkoxycarbonyl-oxy, alkylthio-carbonyloxy, and aryloxy-carbonyloxy, attached to one of said additional carbon atoms that is three atoms from a Y attached to the phosphorus |
| 9 | together $V^2$ and $W^2$ form a cyclic group selected from the group of —$CH_2$—CH(OH)—$CH_2$—, —$CH_2$CH—(OCO$R^3$)$CH_2$—, and —$CH_2$CH—(OCO$_2R^3$)—$CH_2$— |
| 10 | together $V^2$ and $W^2$ form a cyclic group selected from the group of —$CH_2$—CH(OH)—$CH_2$—, —$CH_2$CH—(OCO$R^3$)—$CH_2$— and —$CH_2$CH—(OCO$_2R^3$)—$CH_2$— |

TABLE M

Table of Sub-Markush Groups for the Y Variable

| Sub-Markush Group | Y |
|---|---|
| 1 | both Y groups are —O— |
| 2 | both Y groups are —$NR^6$— |
| 3 | Y is —O— located adjacent to the W', W, W", and $W^2$ groups |
| 4 | Y is —O— located adjacent to the V group or $V^2$ group |
| 5 | one Y is —$NR^6$—, and one Y is —O— |
| 6 | one Y is —$NR^6$—, and the other $YR^1$ is —$NR^{15}R^{16}$, —$OR^7$ or $NR^6$—$(CR^{12}R^{13})_n$—C(O)—$R^{14}$ |
| 7 | one Y is —$NR^6$—, and the other $YR^1$ is —$NR^{15}R^{16}$, and $R^{15}$ is not H |
| 8 | one Y is —$NR^6$—, and the other $YR^1$ is —$NR^{15}R^{16}$, and $R^{16}$ is —$(CR^{12}R^{13})_n$—C(O)—$R^{14}$ |
| 9 | both Y groups are the same —$NR^6$—, such that the phosphonate prodrug moiety has a plane of symmetry through the phosphorus-oxygen double bond |
| 10 | one Y is —$NR^6$—, and the other $YR^1$ is —$NR^{15}R^{16}$, where —$NR^{15}R^{16}$ is a cyclic amine |
| 11 | one Y is —$NR^6$—, and the other $YR^1$ is —$NR^{15}R^{16}$, where —$NR^{15}R^{16}$ is selected from the group consisting of morpholinyl and pyrrolidinyl |
| 12 | one Y is —$NR^6$—, and the other $YR^1$ is —$NR^{15}R^{16}$, where —$NR^{15}R^{16}$ is —$(CR^{12}R^{13})_n$—C(O)$R^{14}$ |

TABLE N

Table of Sub-Markush Groups for the Z Variable

| Sub-Markush Group | Z |
|---|---|
| 1 | —$OR^2$, —$SR^2$, —$R^2$, —$NR_2^2$, —OC(O)$R^3$, —OCO$_2R^3$, —SC(O)$R^3$, —SCO$_2R^3$, —NHC(O)$R^2$, —NHCO$_2R^3$, —$(CH_2)_p$—$OR^{19}$, and —$(CH_2)_p$—$SR^{19}$ |
| 2 | —$OR^2$, —$R^2$, —OC(O)$R^3$, —OCO$_2R^3$, —NHC(O)$R^2$, —NHCO$_2R^3$, —$(CH_2)_p$—$OR^{19}$, and —$(CH_2)_p$—$SR^{19}$ |
| 3 | —$OR^2$, —H, —OC(O)$R^3$, —OCO$_2R^3$, and —NHC(O)$R^2$ |
| 4 | —CH$R^2$OH, —CH$R^2$O—C(O)$R^3$, and —CH$R^2$O—CO$_2R^3$ |
| 5 | —CH$R^2$OH, —CH$R^2$OC(O)$R^3$, —CH$R^2$OC(S)$R^3$, —CH$R^2$OC(S)O$R^3$, —CH$R^2$OC(O)S$R^3$, —CH$R^2$OCO$_2R^3$, —$OR^2$, —$SR^2$, —CH$R^2$, —CH$R^2N_3$, —$CH_2$aryl, —CH(aryl)OH, CH(CH=$CR_2^2$)OH CH(C≡$CR^2$)OH, —$R^2$, —$NR_2^2$, —OCO$R^3$, —OCO$_2R^3$, —SCO$R^3$, —SCO$_2R^3$, —NHCO$R^2$, —NHCO$_2R^3$, —$CH_2$NHaryl, —$(CH_2)_p$-$OR^{19}$ and —$(CH_2)_p$-$SR^{19}$ |
| 6 | —$OR^2$, —$SR^2$, —CH$R^2N_3$, —$R^2$, —OC(O)$R^2$, —OCO$_2R^3$, —SC(O)$R^3$, —SCO$_2R^3$, —NHC(O)$R^2$, —NHCO$_2R^3$, —$CH_2$NHaryl, —$(CH_2)_p$—$OR^{19}$, and —$(CH_2)_p$—$SR^{19}$ |
| 7 | —$OR^2$, —$R^2$, —OC(O)$R^3$, —OCO$_2R^3$, —$CH_3$, —NHC(O)$R^2$, —NHCO$_2R^3$, —$(CH_2)_p$—$OR^{19}$, and —$(CH_2)_p$—$SR^{19}$ |
| 8 | —H, $OR^2$, and —NHC(O)$R^2$ |
| 9 | —H |
| 10 | together V and Z are connected via an additional 3–5 atoms, optionally including 1 heteroatom, to form a cyclic group that is fused to an aryl group at the beta and gamma position to the Y group |
| 11 | together Z and W are connected via an additional 3–5 atoms to form a cyclic group, optionally containing one heteroatom, and V is aryl, substituted aryl, heteroaryl or substituted heteroaryl |

TABLE O

Table of Sub-Markush Groups for the Z' Variable

| Sub-Markush Group | Z' |
|---|---|
| 1 | —$OR^2$, —$SR^2$, —$R^2$, —$NR_2^2$, —OC(O)$R^3$, —OCO$_2R^3$, —SC(O)$R^3$, —SCO$_2R^3$, —NHC(O)$R^2$, —NHCO$_2R^3$, —$(CH_2)_p$—$OR^{19}$, and —$(CH_2)_p$—$SR^{19}$ |
| 2 | —$OR^2$, —$R^2$, —OC(O)$R^3$, —OCO$_2R^3$, —NHC(O)$R^2$, —NHCO$_2R^3$, —$(CH_2)_p$—$OR^{19}$, and —$(CH_2)_p$—$SR^{19}$ |
| 3 | —$OR^2$, —H, —OC(O)$R^3$, —OCO$_2R^3$, and —NHC(O)$R^2$v |
| 4 | —CH$R^2$OH, —CH$R^2$O—C(O)$R^3$, and —CH$R^2$O—CO$_2R^3$ |
| 5 | —OH, —OC(O)$R^3$, —OCO$_2R^3$ and —OC(O)S$R^3$ |
| 6 | —OH, —OC(O)$R^3$, and —OCO$_2R^3$ |
| 7 | —$OR^2$, —$SR^2$, —CH$R^2N_3$, —$R^2$, —OC(O)$R^2$, —OCO$_2R^3$, —SC(O)$R^3$, —SCO$_2R^3$, —NHC(O)$R^2$, —NHCO$_2R^3$, —$CH_2$NHaryl, —$(CH_2)_p$—$OR^{19}$, and —$(CH_2)_p$—$SR^{19}$ |
| 8 | —$OR^2$, —$R^2$, —OC(O)$R^2$, —OCO$_2R^3$, —$CH_3$, —NHC(O)$R^2$, —NHCO$_2R^3$, —$(CH_2)_p$—$OR^{19}$, and —$(CH_2)_p$—$SR^{19}$ |
| 9 | —H, $OR^2$, and —NHC(O)$R^2$ |
| 10 | —H |

TABLE P

Table of Sub-Markush Groups for the $Z^2$ Variable

| Sub-Markush Group | $Z^2$ |
|---|---|
| 1 | —$OR^2$, —$SR^2$, —$R^2$, —$NR_2^2$, —OC(O)$R^3$, —OCO$_2R^3$, —SC(O)$R^3$, —SCO$_2R^3$, |

TABLE P-continued

Table of Sub-Markush Groups for the $Z^2$ Variable

| Sub-Markush Group | $Z^2$ |
|---|---|
| | —NHC(O)R$^2$, —NHCO$_2$R$^3$, —CH$_2$NHaryl, —(CH$_2$)$_p$—OR$^{19}$, and —(CH$_2$)$_p$—SR$^{19}$ |
| 2 | —OR$^2$, —R$^2$, —OC(O)R$^3$, —OCO$_2$R$^3$, —NHC(O)R$^2$, —NHCO$_2$R$^3$, —(CH$_2$)$_p$—OR$^{19}$, and —(CH$_2$)$_p$—SR$^{19}$ |
| 3 | —OR$^2$, —H, —OC(O)R$^3$, —OCO$_2$R$^3$, and —NHC(O)R$^2$ |
| 4 | —CHR$^2$OH, —CHR$^2$O—C(O)R$^3$, and —CHR$^2$O—CO$_2$R$^3$ |
| 5 | —CHR$^2$OH, —CHR$^2$OC(O)R$^3$, —CHR$^2$OC(S)R$^3$, CHR$^2$OCO$_2$R$^3$, —CHR$^2$OC(O)SR$^3$, —CHR$^2$OC(S)OR$^3$, —CH(aryl)OH, CH(CH=CR$_2^2$)OH, CH(C≡CR$^2$)OH, —SR$^2$, —CH$_2$NHaryl, —CH$_2$aryl |
| 6 | —CHR$^2$OH, —CHR$^2$OC(O)R$^3$, —CHR$^2$OC(S)R$^3$, CHR$^2$OCO$_2$R$^3$, —CHR$^2$OC(O)SR$^3$, —CHR$^2$OC(S)OR$^3$, —CH$_2$aryl |
| 7 | —OR$^2$, —SR$^2$, —CHR$^2$N$_3$, —R$^2$, —OC(O)R$^2$, —OCO$_2$R$^3$, —SC(O)R$^3$, —SCO$_2$R$^3$, —NHC(O)R$^2$, —NHCO$_2$R$^3$, —CH$_2$NHaryl, —(CH$_2$)$_p$—OR$^{19}$, and —(CH$_2$)$_p$—SR$^{19}$ |
| 8 | —OR$^2$, —R$^2$, —OC(O)R$^2$, —OCO$_2$R$^3$, —CH$_3$, —NHC(O)R$^2$, —NHCO$_2$R$^3$, —(CH$_2$)$_p$—OR$^{19}$, and —(CH$_2$)$_p$—SR$^{19}$ |
| 9 | —H, OR$^2$, and —NHC(O)R$^2$ |
| 10 | —H |
| 11 | together V$^2$ and Z$^2$ are connected via an additional 3–5 atoms to form a cyclic group containing 5–7 ring atoms, optionally containing 1 heteroatom, and substituted with hydroxy, acylocy, alkoxy carbonyloxy, oraryloxycarbon yloxy attached to a carbon atom that is three atoms from a Y attached to phosphorus |

TABLE Q

Table of Markush Groups by Variable

| | Markush Group A | Markush Group B | Markush Group C | Markush Group D | Markush Group E |
|---|---|---|---|---|---|
| n | 1 and 2 | 1 | 2 | 1, and the carbon attached to R$^{12}$ and R$^{13}$ has S stereochemistry | |
| p | 2 | 3 | | | |
| R$^2$ | —H, lower alkyl, lower aryl, lower alicyclic, and lower aralkyl | ethyl, methyl and H | —H, and aryl | —H | |
| R$^3$ | lower alkyl, lower aryl, lower alicyclic and lower aralkyl | lower alkyl, lower aryl | ethyl and methyl | | |
| R$^5$ | substituted phenyl, substituted pyrrolyl, substituted oxazolyl, substituted thiazolyl, substituted isothiazolyl, substituted pyrazolyl, substituted isoxazolyl, substituted pyridinyl, substituted thienyl, substituted furanyl, substituted | substituted pyrrolyl, substituted oxazolyl, substituted thiazolyl, substituted isothiazolyl, substituted pyrazolyl, substituted isoxazolyl, substituted pyridinyl, substituted thienyl, substituted furanyl, substituted pyrimidinyl, and substituted | substituted pyrrolyl, substituted oxazolyl, substituted thiazolyl, substituted isothiazolyl, substituted pyrazolyl, substituted isoxazolyl, substituted pyridinyl, substituted pyrimidinyl, and substituted pyridazinyl | substituted thienyl, substituted furanyl and substituted phenyl | substituted phenyl |

TABLE Q-continued

Table of Markush Groups by Variable

| | Markush Group A | Markush Group B | Markush Group C | Markush Group D | Markush Group E |
|---|---|---|---|---|---|
| | pyrimidinyl, and substituted pyridazinyl | pyridazinyl | | | |
| $R^6$ | —H, and lower alkyl, acyloxyalkyl | —H and C1–C6 alkyl | —H, methyl, and ethyl | —H and methyl | —H |
| $R^7$ | lower alkyl, lower aryl and lower alicyclic | lower alkyl and lower aryl | lower aryl | substituted phenyl | phenyl, phenyl substituted with 4-NHC(O)CH$_3$, —Cl, —Br, 2-C(O)OCH$_2$CH$_3$, or —CH$_3$ |
| $R^{11}$ | alkyl and aryl | lower alkyl | C1–C4 alkyl | methyl | |
| $R^{14}$ | OR$^{17}$, SR$^{17}$ and NR$^2$R$^{20}$ | OR$^{17}$ and SR$^{17}$ | OR$^{17}$ | | |
| $R^{17}$ | lower alkyl, lower aryl, lower aralkyl, alicyclic, or together R$^{17}$ and R$^{17}$ are connected via 2–6 atoms optionally including 1 heteroatom selected from the group of N, O, and S | methyl, ethyl, isopropyl, propyl, t-butyl, and benzyl | methyl, ethyl, isopropyl, propyl and benzyl | ethyl and isopropyl | |
| $R^{18}$ | —H and lower alkyl | —H, methyl and ethyl | | | |
| $R^{19}$ | —H and acetyl | —H | | | |
| $R^{20}$ | —H, C1–C4 alkyl, C4–C6 aryl, C2–C7 alicyclic and C5–C7 aralkyl | —H and C1–C4 alkyl | | | |
| D" | —H, alkyl, OH, and —OC(O)R$^3$ | —H | | | |
| $G^2$ | C and O | C | O | | |
| $G^3$ | C and S | C | S | | |
| $G^4$ | C and N | C | N | | |
| $J^2$ | —H, —NR$_2^4$, —C(O)NR$_2^4$, —CO$_2$R$^3$, halo, —S(O)$_2$NR$_2^4$, lower alkyl, lower alicyclic, lower alkenyl, lower alkynyl, lower perhaloalkyl, lower haloalkyl, lower aryl, lower alkylaryl, lower alkylene-OH, —OR$^{11}$, —CR$_2^2$NR$_2^4$, —CN, —C(S)NR$_2^4$, —OR$^2$, —SR$^2$, —N$_3$, —NO$_2$, —NHC(S)NR$_2^4$, —NR$^{18}$C(O)R$^2$, and —CR$_2^2$CN | —H, —NO$_2$, lower alkyl, lower alkylaryl, lower alkoxy, lower perhaloalkyl, halo, —CH$_2$NHR$^4$, —C(O)NR$_2^4$, —S(O)$_2$NHR$^4$, —OH, —NH$_2$, and —NHC(O)R$^2$ | —OCH$_3$, —CN, —H, halo, —NH$_2$ and —NO$_2$ | —OCH$_3$ | —H, —OR$^3$, —NO$_2$, halo, —(CH$_2$)$_2$aryl, —(CH$_2$)$_2$NHaryl, —S(O)$_2$NHR$^7$, —CN, —NR$_2^4$ |
| $J^3$ | —H, NR$_2^4$, —C(O)NR$_2^4$, —CO$_2$R$^3$, halo, —S(O)$_2$NR$_2^4$, lower alkyl, lower alicyclic, lower alkenyl, lower alkynyl, lower perhaloalkyl, lower | —H, —NO$_2$, lower alkyl, lower alkylaryl, lower alkoxy, lower perhaloalkyl, halo, —CH$_2$NHR$^4$, —C(O)NR$_2^4$, —S(O)$_2$NHR$^4$, —OH, —NH$_2$, and —NHC(O)R$^2$ | —OCH$_3$, —CN, —H, halo, —NH$_2$ and —NO$_2$ | not halo or alkenyl | —H, —OR$^3$, —NO$_2$, halo, —(CH$_2$)$_2$aryl, —(CH$_2$)$_2$NHaryl, —S(O)$_2$NHR$^7$, —CN, —NR$_2^4$ |

TABLE Q-continued

Table of Markush Groups by Variable

| | Markush Group A | Markush Group B | Markush Group C | Markush Group D | Markush Group E |
|---|---|---|---|---|---|
| | haloalkyl, lower aryl, lower alkylaryl, lower alkylene-OH, —OR$^{11}$, —CR$_2$$^2$NR$_2$$^4$, —CN, —C(S)NR$_2$$^4$, —OR$^2$, —SR$^2$, —N$_3$, —NO$_2$, —NHC(S)NR$_2$$^4$, —NR$^{18}$C(O)R$^2$, and —CR$_2$$^2$CN | | | | |
| J$^4$ | —H, NR$_2$$^4$, —C(O)NR$_2$$^4$, —CO$_2$R$^3$, halo, —S(O)$_2$NR$_2$$^4$, lower alkyl, lower alkenyl, lower alkenyl, lower alkynyl, lower perhalo-alkyl, lower haloalkyl, lower aryl, lower alkylaryl, lower alkylene-OH, —OR$^{11}$, —CR$_2$$^2$NR$_2$$^4$, —CN, —C(S)NR$_2$$^4$, —OR$^2$, —SR$^2$, —N$_3$, —NO$_2$, —NHC(S)NR$_2$$^4$, —NR$^{18}$C(O)R$^2$, and —CR$_2$$^2$CN | —H, —NO$_2$, lower alkyl, lower alkylaryl, lower alkoxy, lower perhaloalkyl, halo, —CH$_2$NHR$^4$, —C(O)NR$_2$$^4$, —S(O)$_2$NHR$^4$, —OH, —NH$_2$, and —NHC(O)R$^2$ | —OCH$_3$, —CN, —H, halo, —NH$_2$ and —NO$_2$ | not halo or alkenyl | —H, —OR$^3$, —NO$_2$, halo, —(CH$_2$)$_2$aryl, —(CH$_2$)$_2$NHaryl, —S(O)$_2$NHR$^7$, —CN, —NR$_2$$^4$ |
| J$^5$ | —H, NR$_2$$^4$, —C(O)NR$_2$$^4$, —CO$_2$R$^3$, halo, —S(O)$_2$NR$_2$$^4$, lower alkyl, lower alenyl, lower alkenyl, lower alkynyl, lower perhalo-alkyl, lower haloalkyl, lower aryl, lower alkylaryl, lower alkylene-OH, —OR$^{11}$, —CR$_2$$^2$NR$_2$$^4$, —CN, —C(S)NR$_2$$^4$, —OR$^2$, —SR$^2$, —N$_3$, —NO$_2$, —NHC(S)NR$_2$$^4$, —NR$^{18}$C(O)R$^2$, and —CR$_2$$^2$CN | —H, —NO$_2$, lower alkyl, lower alkylaryl, lower alkoxy, lower perhaloalkyl, halo, —CH$_2$NHR$^4$, —C(O)NR$_2$$^4$, —S(O)$_2$NHR$^4$, —OH, —NH$_2$, and —NHC(O)R$^2$ | —OCH$_3$, —CN, —H, halo, —NO$_2$ and —CH$_2$NHR$^4$ | not halo or alkenyl | —H, —OR$^3$, —NO$_2$, halo, —(CH$_2$)$_2$aryl, —(CH$_2$)$_2$NHaryl, —S(O)$_2$NHR$^7$, —CN, —NR$_2$$^4$ |
| J$^6$ | —H, NR$_2$$^4$, —C(O)NR$_2$$^4$, —CO$_2$R$^3$, halo, —S(O)$_2$NR$_2$$^4$, lower alkyl, lower alkenyl, lower alkenyl, lower alkynyl, lower perhalo-alkyl, lower haloalkyl, lower aryl, lower alkylaryl, lower alkylene-OH, —OR$^{11}$, | —H, —NO$_2$, lower alkyl, lower aryl, lower alkylaryl, lower alkoxy, lower perhaloalkyl, halo, —CH$_2$NHR$^4$, —C(O)NR$_2$$^4$, —S(O)$_2$NHR$^4$, —OH, —NH$_2$, and —NHC(O)R$^2$ | —OCH$_3$, —CN, —H, halo, and lower alkyl | | |

TABLE Q-continued

Table of Markush Groups by Variable

| | Markush Group A | Markush Group B | Markush Group C | Markush Group D | Markush Group E |
|---|---|---|---|---|---|
| | $-CR_2{}^2NR_2{}^4$, | | | | |
| | $-CN$, | | | | |
| | $-C(S)NR_2{}^4$, | | | | |
| | $-OR^2$, $-SR^2$, $-N_3$, | | | | |
| | $-NO_2$, | | | | |
| | $-NHC(S)NR_2{}^4$, | | | | |
| | $-NR^{18}C(O)R^2$, | | | | |
| | and $-CR_2{}^2CN$ | | | | |
| $W^3$ | $-H$, alkyl | $-H$ | | | |
| $W''$ | $-H$, alkyl, aralkyl, alicyclic, aryl, substituted aryl, heteroaryl, substituted heteroaryl, 1-alkenyl, and 1-alkynyl | $-H$, $-R^3$, aryl, substituted aryl, heteroaryl, and substituted heteroaryl | $-H$, alkyl, aralkyl, alicyclic, aryl, substituted aryl, heteroaryl, substituted heteroaryl | same as $W^2$ | $-H$ |
| $X^3$ | C | N | | | |
| $X^4$ | C | N | | | |
| $X^5$ | C | N | | | |

In the following examples of compounds, the following prodrugs are envisioned:

Acyloxyalkyl esters;
Alkoxycarbonyloxyalkyl esters;
Aryl esters;
Benzyl and substituted benzyl esters;
Disulfide containing esters;
Substituted (1,3-dioxolen-2-one)methyl esters;
Substituted 3-phthalidyl esters;
Cyclic-[5-hydroxycyclohexan-1,3-diyl) diesters and hydroxy protected forms;
Cyclic-[2-hydroxymethylpropan-1,3-diyl] diesters and hydroxy protected forms;
Cyclic-(1-arylpropan-1,3-diyl);
Monoaryl ester N-substituted mono phosphoramidates;
Bis Omega substituted lactone esters; and all mixed esters resulted from possible combinations of above esters;

Also envisioned are the following:

Bis-pivaloyloxymethyl esters;
Bis-isobutyryloxymethyl esters;
Cyclic-[1-(3-chlorophenyl)propan-1,3-diyl]diesters;
Cyclic-[1-(3,5-dichlorophenyl)propan-1,3-diyl]diester;
Cyclic-[1-(3-bromo-4-fluorophenyl)propan-1,3-diyl] diester;
Cyclic-[2-hydroxymethy lprop an-1,3-diyl] diester;
Cyclic-[2-acetoxymethylpropan-1,3-diyl] diester;
Cyclic-[2-methyloxycarbonyloxymethylpropan-1,3-diyl] diester;
Cyclic-[1-phenylpropan-1,3-diyl] diesters;
Cyclic-[1-(2-pyridyl)propan-1,3-diyl)] diesters;
Cyclic-[1-(3-pyridyl)propan-1,3-diyl] diesters;
Cyclic-[1-(4-pyridyl)propan-1,3-diyl] diesters;
Cyclic-[5-hydroxycyclohexan-1,3-diyl] diesters and hydroxy protected forms;
Bis-benzoylthiomethyl esters;
Bis-benzoylthioethyl esters;
Bis-benzoyloxymethyl esters;
Bis-p-fluorobenzoyloxymethyl esters;
Bis-6-chloronicotinoyloxymethyl esters;
Bis-5-bromonicotinoyloxymethyl esters;
Bis-thiophenecarbonyloxymethyl esters;
Bis-2-furoyloxymethyl esters;
Bis-3-furoyloxymethyl esters;
Diphenyl esters;
Bis-(4-methoxyphenyl) esters;
Bis-(2-methoxyphenyl) esters;
Bis-(2-ethoxyphenyl) esters;
Mono-(2-ethoxyphenyl) esters;
Bis-(4-acetamidophenyl) esters;
Bis-(4-acetoxyphenyl) esters;
Bis-(4-hydroxyphenyl) esters;
Bis-(2-acetoxyphenyl) esters;
Bis-(3-acetoxyphenyl) esters;
Bis-(4-morpholinophenyl) esters;
Bis-[4-(1-triazolophenyl) esters;
Bis-(3-N,N-dimethylaminophenyl) esters;
Bis-(1,2,3,4-tetrahydronapthalen-2-yl) esters;
Bis-(3-chloro-4-methoxy)benzyl esters;
Bis-(3-bromo-4-methoxy)benzyl esters;
Bis-(3-cyano-4-methoxy)benzyl esters;
Bis-(3-chloro-4-acetoxy)benzyl esters;
Bis-(3-bromo-4-acetoxy)benzyl esters;
Bis-(3-cyano-4-acetoxy)benzyl esters;
Bis-(4-chloro)benzyl esters;
Bis-(4-acetoxy)benzyl esters;
Bis-(3,5-dimethoxy-4-acetoxy)benzyl esters;
Bis-(3-methyl-4-acetoxy)benzyl esters;
Bis-(benzyl)esters;
Bis-(3-methoxy-4-acetoxy)benzyl esters;
Bis-(6'-hydroxy-3',4'-dithia)hexyl esters;
Bis-(6'-acetoxy-3',4'-dithia)hexyl esters;
(3,4-dithiahexan-1,6-diyl) esters;
Bis-(5-methyl-1,3-dioxolen-2-one-4-yl)methyl esters;
Bis-(5-ethyl-1,3-dioxolen-2-one-4-yl)methyl esters;
Bis-(5-tert-butyl-1,3-dioxolen-2-one-4-yl)methyl esters;
Bis-3-(5,6,7-trimethoxy)phthalidyl esters;
Bis-(cyclohexyloxycarbonyloxyethyl) esters;
Bis-(isopropyloxycarbonyloxymethyl) esters;
Bis-(ethyloxycarbonyloxymethyl) esters;
Bis-(methyloxycarbonyloxymethyl) esters;
Bis-(isopropylthiocarbonyloxymethyl) esters;

Bis-(phenyloxycarbonyloxymethyl) esters;
Bis-(benzyloxycarbonyloxymethyl) esters;
Bis-(phenylthiocarbonyloxymethyl) esters;
Bis-(p-methoxyphenoxycarbonyloxymethyl) esters;
Bis-(m-methoxyphenoxycarbonyloxymethyl) esters;
Bis-(o-methoxyphenoxycarbonyloxymethyl) esters;
Bis-(o-methylphenoxycarbonyloxymethyl) esters;
Bis-(p-chlorophenoxycarbonyloxymethyl) esters;
Bis-(1,4-biphenoxycarbonyloxymethyl) esters;
Bis-[(2-phthalimidoethyl)oxycarbonyloxymethyl]esters;
Bis-(N-phenyl-N-methylcarbamoyloxymethyl) esters;
Bis-(2,2,2-trichloroethyl) esters;
Bis-(2-bromoethyl) esters;
Bis-(2-iodoethyl) esters;
Bis-(2-azidoethyl) esters;
Bis-(2-acetoxyethyl) esters;
Bis-(2-aminoethyl) esters;
Bis-(2-N,N-dimethylaminoethyl) esters;
Bis-(2-aminoethyl) esters;
Bis-(methoxycarbonylmethyl) esters;
Bis-(2-aminoethyl) esters;
Bis-[N,N-di(2-hydroxyethyl)]carbamoylmethylesters;
Bis-(2-aminoethyl) esters;
Bis-(2-methyl-5-thiazolomethyl) esters;
Bis-(bis-2-hydroxyethylcarbamoylmethyl) esters.
O-(3,4-methylenedioxyphenyl)-[N-(1-ethoxycarbonyl)ethyl]phosphoramidates(—P(O)(O-Phenyl-3,4-methylenedioxy)(—N(H)CH(Me)CO$_2$Et)
O-(3,4-methylenedioxyphenyl)-[N-(1-ethoxycarbonyl-1-methyl)ethyl]phosphoramidates (—P(O)(O-Phenyl-3,4-methylenedioxy)(—NH—C(CH$_3$)$_2$—CO$_2$Et)
O-phenyl-[N-(1-ethoxycarbonyl)ethyl]phosphoramidates (—P(O)(OPh)(N(H)—CH(Me)CO$_2$Et)
O-phenyl-[N-(1-methoxycarbonyl)ethyl]phosphoramidates (—P(O)(OPh)(N(H)—CH(Me)CO$_2$Me)
O-(3-chlorophenyl)-[N-(1-ethoxycarbonyl)ethyl] phosphoramidates (—P(O)(OPh-3-Cl)(NH—CH(Me)CO$_2$Et)
O-(2-chlorophenyl)-[N-(1-ethoxycarbonyl)ethyl] phosphoramidates (—P(O)(OPh-2-Cl)(NH—CH(Me)CO$_2$Et)
O-(4-chlorophenyl)-[N-(1-ethoxycarbonyl)ethyl] phosphoramidates (—P(O)(OPh-4-Cl)(NH—CH(Me)CO$_2$Et)
O-(4-acetamidophenyl)-[N-(1-ethoxycarbonyl)ethyl] phosphoramidates (—P(O)(OPh-4-NHAc)(NH—CH(Me)CO$_2$Et)
O-(2-ethoxycarbonylphenyl)-[N-(1-ethoxycarbonyl)ethyl] phosphoramidates (—P(O)(OPh-2-CO$_2$Et)(NH—CH(Me)CO$_2$Et)
O-phenyl-[N-(1-ethoxycarbonyl-1-methyl)ethyl] phosphoramidates (—P(O)(OPh)(NH—C(Me)$_2$CO$_2$Et)
O-phenyl-[N-(1-methoxycarbonyl-1-methyl)ethyl] phosphoramidates (—P(O)(OPh)(NH—C(Me)$_2$CO$_2$Me)
O-(3-chlorophenyl)-[N-(1-ethoxycarbonyl-1-methyl)ethyl] phosphoramidates (—P(O)(OPh-3-Cl)(NH—C(Me)$_2$CO$_2$Et)
O-(2-chlorophenyl)-[N-(1-ethoxycarbonyl-1-methyl)ethyl] phosphoramidates (—P(O)(OPh-2-Cl)(NH—C(Me)$_2$CO$_2$Et)
O-(4-chlorophenyl)-[N-(1-ethoxycarbonyl-1-methyl)ethyl] phosphoramidates (—P(O)(OPh-4-Cl)(NH—C(Me)$_2$CO$_2$Et)
O-(4-acetamidophenyl)-[N-(1-ethoxycarbonyl-1-methyl)ethyl]phosphoramidates (—P(O)(OPh-4-NHAc)(NH—C(Me)$_2$CO$_2$Et)
O-(2-ethoxycarbonylphenyl)-[N-(1-ethoxycarbonyl-1-methyl)ethyl]phosphoramidates (—P(O)(OPh-2-CO$_2$Et)(NH—C(Me)$_2$CO$_2$Et)
O-phenyl-[N-(ethoxycarbonyl)methyl]phosphoramidates (—P(O)(OPh)M—CH$_2$CO$_2$Et)
O-phenyl-[N-(methoxycarbonyl)methyl]phosphoramidates (—P(O)(OPh)(NH—CH$_2$CO$_2$Me)
O-(3-chlorophenyl)-[N-(ethoxycarbonyl)methyl] phosphoramidates (—P(O)(OPh-3-Cl)(NH—CH$_2$CO$_2$Et)
O-(2-chlorophenyl)-[N-(ethoxycarbonyl)methyl] phosphoramidates (—P(O)(OPh-2-Cl)(NH—CH$_2$CO$_2$Et)
O-(4-chlorophenyl)-[N-(ethoxycarbonyl)methyl] phosphoramidates (—P(O)(OPh-4-Cl)(NH—CH$_2$CO$_2$Et)
O-(4-acetamidophenyl)-[N-(ethoxycarbonyl)methyl] phosphoramidates (—P(O)(OPh-4-NHAc)(NH—CH$_2$CO$_2$Et)
O-(2-ethoxycarbonylphenyl)-[N-(ethoxycarbonyl)methyl] phosphoramidates (—P(O)(OPh-2-CO$_2$Et)(NH—CH$_2$CO$_2$Et)

Further envisioned are the following:

Bis-pivaloyloxymethyl esters;
Bis-isobutyryloxymethyl esters;
Cyclic-[1-(3-chlorophenyl)propan-1,3-diyl]diesters;
Cyclic-[1-3,5-dichlorophenyl)propan-1,3-diyl]diester;
Cyclic-[1-(3-bromo-4-fluorophenyl)propan-1,3-diyl] diester;
Cyclic-(2-hydroxymethylpropan-1,3-diyl) ester;
Cyclic-(2-acetoxymethylpropan-1,3-diyl) ester;
Cyclic-(2-methyloxycarbonyloxymethylpropan-1,3-diyl) ester;
Cyclic-(2-cyclohexylcarbonyloxymethylpropan-1,3-diyl) ester;
Cyclic-[phenylpropan-1,3-diyl] diesters;
Cyclic-[1-(2-pyridyl)propan-1,3-diyl)] diesters;
Cyclic-[1-(3-pyridyl)propan-1,3-diyl] diesters;
Cyclic-[1-(4-pyridyl)propan-1,3-diyl] diesters;
Cyclic-[5-hydroxycyclohexan-1,3-diyl] diesters and hydroxy protected forms;
Bis-benzoylthiomethyl esters;
Bis-benzoylthioethylesters;
Bis-benzoyloxymethyl esters;
Bis-p-fluorobenzoyloxymethyl esters;
Bis-6-chloronicotinoyloxymethyl esters;
Bis-5-bromonicotinoyloxymethyl esters;
Bis-thiophenecarbonyloxymethyl esters;
Bis-2-furoyloxymethyl esters;
Bis-3-furoyloxymethyl esters;
Diphenyl esters;
Bis-(2-methylphenyl) esters;
Bis-(2-methoxyphenyl) esters;
Bis-(2-ethoxyphenyl) esters;
Bis-(4-methoxyphenyl) esters;
Bis-(3-bromo-4-methoxybenzyl) esters;
Bis-(4-acetoxybenzyl) esters;
Bis-(3,5-dimethoxy-4-acetoxybenzyl) esters;
Bis-(3-methyl-4-acetoxybenzyl) esters;
Bis-(3-methoxy-4-acetoxybenzyl) esters;
Bis-(3-chloro-4-acetoxybenzyl) esters;
Bis-(cyclohexyloxycarbonyloxymethyl) esters;
Bis-(isopropyloxycarbonyloxymethyl) esters;
Bis-(ethyloxycarbonyloxymethyl) esters;
Bis-(methyloxycarbonyloxymethyl) esters;
Bis-(isopropylthiocarbonyloxymethyl) esters;
Bis-(phenyloxycarbonyloxymethyl) esters;
Bis-(benzyloxycarbonyloxymethyl) esters;
Bis-(phenylthiocarbonyloxymethyl) esters;
Bis-(p-methoxyphenoxycarbonyloxymethyl) esters;
Bis-(m-methoxyphenoxycarbonyloxymethyl) esters;

Bis-(o-methoxyphenoxycarbonyloxymethyl) esters;
Bis-(o-methylphenoxycarbonyloxymethyl) esters;
Bis-(p-chlorophenoxycarbonyloxymethyl) esters;
Bis-(1,4-biphenoxycarbonyloxymethyl) esters;
Bis-[(2-phthalimidoethyl)oxycarbonyloxymethyl]esters;
Bis-(6-hydroxy-3,4-dithia)hexyl esters;
Cyclic-(3,4-dithiahexan-1,6-diyl) esters;
Bis-(2-bromoethyl) esters;
Bis-(2-aminoethyl) esters;
Bis-(2-N,N-diaminoethyl) esters;
O-(3,4-methylenedioxyphenyl)-[N-(1-ethoxycarbonyl)ethyl]phosphoramidates(—P(O)(O-Phenyl-3,4-methylenedioxy)(—N(H)CH(Me)CO$_2$Et)
O-phenyl-[N-(1-ethoxycarbonyl)ethyl]phosphoramidates (—P(O)(OPh)(NH—*CH(Me)CO$_2$Et)
O-(3,4-methylenedioxyphenyl)-[N-(1-ethoxycarbonyl-1-methyl)ethyl]phosphoramidates(—P(O)(O-Phenyl-3,4-methylenedioxy)(-NH—C(CH$_3$)$_2$—CO$_2$Et)
O-phenyl-[N-(1-methoxycarbonyl)ethyl]phosphoramidates (—P(O)(OPh)(NH—*CH(Me)CO$_2$Me)
O-(3-chlorophenyl)-[N-(1-ethoxycarbonyl)ethyl]phosphoramidates (—P(O)(OPh-3-C$_1$)(NH—*CH(Me)CO$_2$Et)
O-(2-chlorophenyl)-[N-(1-ethoxycarbonyl)ethyl]phosphoramidates (—P(O)(OPh-2-Cl)(NH—*CH(Me)CO$_2$Et)
O-(4-chlorophenyl)-[N-(1-ethoxycarbonyl)ethyl]phosphoramidates (—P(O)(OPh-4-Cl)(NH—*CH(Me)CO2Et)
O-($_4$-acetamidophenyl)-[N-(1-ethoxycarbonyl)ethyl]phosphoramidates (—P(O)(OPh-4-NHAc)(NH—*CH(Me)CO$_2$Et)
O-(2-ethoxycarbonylphenyl)-[N-(1-ethoxycarbonyl)ethyl]phosphoramidates (—P(O)(OPh-2-CO$_2$Et)(NH—*CH(Me)CO$_2$Et)
O-phenyl-[N-(1-ethoxycarbonyl-1-methyl)ethyl]phosphoramidates (—P(O)(OPh)(NH—C(Me)$_2$CO$_2$Et)
O-phenyl-[N-(1-methoxycarbonyl-1-methyl)ethyl]phosphoramidates (—P(O)(OPh)(NH—C(Me)$_2$CO$_2$Me)
O-(3-chlorophenyl)-[N-(1-ethoxycarbonyl-1-methyl)ethyl]phosphoramidates (—P(O)(OPh-3-Cl)(NH—C(Me)$_2$CO$_2$Et)
O-(2-chlorophenyl)-[N-(1-ethoxycarbonyl-1-methyl)ethyl]phosphoramidates (—P(O)(OPh-2-Cl)(NH—C(Me)$_2$CO$_2$Et)
O-(4-chlorophenyl)-[N-(1-ethoxycarbonyl-1-methyl)ethyl]phosphoramidates (—P(O)(OPh-4-Cl)(NH—C(Me)$_2$CO$_2$Et)
O-(4-acetamidophenyl)-[N-(1-ethoxycarbonyl-1-methyl)ethyl]phosphoramidates (—P(O)(OPh-4-NHAc)(NH—C(Me)$_2$CO$_2$Et)
O-(2-ethoxycarbonylphenyl)-[N-(1-ethoxycarbonyl-1-methyl)ethyl]phosphoramidates (—P(O)(OPh-2-CO$_2$Et)(NH—C(Me)$_2$CO$_2$Et)

In the above prodrugs an asterisk (*) on a carbon refers to the L-configuration.

O-phenyl-[N-(ethoxycarbonyl)methyl]phosphoramidates (—P(O)(OPh)(NH—CH$_2$CO$_2$Et)
O-phenyl-[N-(methoxycarbonyl)methyl]phosphoramidates (—P(O)(OPh)(NH—CH$_2$CO$_2$Me)
O-(3-chlorophenyl)-[N-(ethoxycarbonyl)methyl]phosphoramidates (—P(O)(OPh-3-Cl)(NH—CH$_2$CO$_2$Et)
O-(2-chlorophenyl)-[N-(ethoxycarbonyl)methyl]phosphoramidates (—P(O)(OPh-2-Cl)(NH—CH$_2$CO$_2$Et)
O-(4-chlorophenyl)-[N-(ethoxycarbonyl)methyl]phosphoramidates (—P(O)(OPh-4-Cl)(NH—CH$_2$CO$_2$Et)
O-(4-acetamidophenyl)-[N-(ethoxycarbonyl)methyl]phosphoramidates (—P(O)(OPh-4-NHAc)(NH—CH$_2$CO$_2$Et)
O-(2-ethoxycarbonylphenyl)-[N-(ethoxycarbonyl)methyl]phosphoramidates (—P(O)(OPh-2-CO$_2$Et)(NH—CH$_2$CO$_2$Et)

Examples of compounds of formula I include, but are not limited to pharmaceutically acceptable salts and prodrugs of the compounds named in Tables 1 and 2 as follows:

TABLE 1

| cmpd no. | L | X³ | X⁴ | X⁵ | J² | J³ | J⁴ | J⁵ | J⁶ | M-1 found | HPLC Rt |
|---|---|---|---|---|---|---|---|---|---|---|---|
| 1.01 | L1 | C | C | C | H | NO₂ | H | NO₂ | H | 313 | 5.30ᵗ |
| 1.02 | L1 | C | C | C | NH₂ | NO₂ | H | NO₂ | H | 328 | 5.58ᵗ |
| 1.03 | L1 | C | C | C | MeO | H | H | Cl | H | 287 | 5.71ᵗ |
| 1.04 | L1 | C | C | C | Cl | H | H | Cl | H | 291/293 | 6.27ᵗ |
| 1.05 | L1 | C | C | C | SO₂NHMe | H | H | CF₃ | H | 384 | 5.82ᵗ |
| 1.06 | L1 | C | C | C | SO₂NHMe | H | H | Cl | H | 350 | 5.43ᵗ |
| 1.07 | L1 | C | C | C | SO₂NHMe | H | H | H | H | 316 | 5.25ᵗ |
| 1.08 | L1 | C | C | C | SO₂NH(n-Pr) | H | H | H | H | 378 | 6.12ᵗ |
| 1.09 | L1 | C | C | C | OH | H | H | H | H | 239 | 3.97ᵗ |
| 1.10 | L1 | C | C | C | H | Me | NH₂ | Me | H | 251 | 6.10ᵗ |
| 1.11 | L1 | C | C | C | H | Br | Cl | H | H | 301/303 | 5.90ᵗ |
| 1.12 | L1 | C | C | C | H | H | H | MeO | H | 238 | 4.64ᵗ |
| 1.13 | L1 | C | C | C | MeO | H | H | H | H | 317 | 6.00ᵗ |
| 1.14 | L1 | C | C | C | C(O)NHCH₂-(4-ClPh) | H | H | H | H | 390 | 6.12ᵗ |
| 1.15 | L1 | C | C | C | C(O)NHCH₂—CH₂—CH₂(4-ClPh) | H | H | H | H | 404 | 6.42ᵗ |
| 1.16 | L1 | C | C | C | SO₂NHBn | H | H | H | H | 392 | 6.17ᵗ |
| 1.17 | L1 | C | C | C | SO₂NH₂ | H | H | H | H | 302 | 4.44ᵗ |
| 1.18 | L1 | C | C | C | Me | Me | Me | Me | Me | 293 | 5.08ᵗ |
| 1.19 | L1 | C | C | C | CO₂Et | CO₂Et | NHAc | H | H | 367 | 6.00ᵗ |
| 1.20 | L1 | C | C | C | H | Me | Cl | H | Me | 294 | 4.12ᵗ |
| 1.21 | L1 | C | C | C | Cl | H | OH | H | H | 305/307 | 6.66ᵗ |
| 1.22 | L1 | C | C | C | CO₂Me | H | Me | H | H | 297 | 4.71ᵗ |
| 1.23 | L1 | C | C | C | C(O)NH₂ | H | OH | H | H | 280 | 6.89ᵗ |
| 1.24 | L1 | C | C | C | CO₂Et | H | NO₂ | H | H | 311 | 5.56ᵗ |
| 1.25 | L1 | C | C | C | H | H | H | H | H | 268 | 4.81ᵗ |
| 1.27 | L1 | C | C | C | C(O)NH(2,4-difluoro-Ph) | H | H | H | H | 378 | 5.56ᵗ |
| 1.28 | L1 | C | C | C | H | Cl | H | Cl | H | 291/293 | 6.43ᵗ |
| 1.29 | L1 | C | C | C | H | CO₂H | H | Br | H | 239 | 4.41ᵗ |
| 1.30 | L1 | C | C | C | MeO | MeO | H | CHO | H | 345/347 | 5.37ᵗ |
| 1.31 | L1 | C | C | C | NO₂ | H | H | H | H | 311 | 5.12ᵗ |
| 1.32 | L1 | C | C | C | Ph | H | H | H | H | 268 | 4.78ᵗ |
| 1.33 | L1 | C | C | C | CO₂Et | H | Br | H | H | 299 | 6.75ᵗ |
| 1.34 | L1 | C | C | C | H | C(O)Et | H | H | H | 295 | 5.32ᵗ |
| 1.35 | L1 | C | C | C | H | H | H | Cl | H | 301/303 | 6.01ᵗ |
| 1.36 | L1 | C | C | C | MeO | H | H | CN | H | 279 | 4.54ᵗ |
| 1.37 | L1 | C | C | C | Et | H | H | H | H | 278 | 5.18ᵗ |
| 1.38 | L1 | C | C | C | NO₂ | H | H | H | Me | 251 | 5.13ᵗ |
| 1.39 | L1 | C | C | C | H | H | NHAc | H | H | 282 | 5.76ᵗ |
|  |  |  |  |  |  |  |  |  |  | 280 | 3.94ᵗ |

TABLE 1-continued

| cmpd no. | L | X³ | X⁴ | X⁵ | J² | J³ | J⁴ | J⁵ | J⁶ | M-1 found | HPLC Rt |
|---|---|---|---|---|---|---|---|---|---|---|---|
| 1.40 | L1 | C | C | C | Me | Me | Me | Me | H | 279 | 7.07ʳ |
| 1.41 | L1 | C | C | C | H | Ph | H | H | H | 299 | 7.02ʳ |
| 1.42 | L1 | C | C | C | SO₂NH₂ | H | H | Cl | H | 336 | 5.37ʳ |
| 1.43 | L1 | C | C | C | H | H | NHC(O)—CH₂-(pyrrolidin-1-yl) | H | H | 349 | 5.06ʳ |
| 1.44 | L1 | C | C | C | H | Me | Me | H | H | 251 | 5.10ʳ |
| 1.45 | L1 | C | C | C | NO₂ | CH₂NH₂ | NO₂ | H | H | 313 | 5.59ʳ |
| 1.46 | L1 | C | C | C | H | F | NH₂ | H | H | 252 | 2.35ʳ |
| 1.47 | L1 | C | C | C | H | CH₂OH | H | H | H | 256 | 5.08ˢ |
| 1.48 | L1 | C | C | C | Br | H | H | H | H | 253 | 4.52ʳ |
| 1.49 | L1 | C | C | C | CH₂CH₂OH | H | H | H | H | 301/303 | 5.72ʳ |
| 1.50 | L1 | C | C | C | H | H | C(O)NH₂ | H | H | 267 | 5.51ʳ |
| 1.51 | L1 | C | C | C | H | CN | CN | H | H | 266 | 3.61ʳ |
| 1.52 | L1 | C | C | C | H | NO₂ | H | H | H | 248 | 3.64ʳ |
| 1.53 | L1 | C | C | C | CN | H | NH₂ | H | H | 248 | 3.98ˢ |
| 1.54 | L1 | C | C | C | i-Pr | null | H | H | H | 248 | 4.96ʳ |
| 1.55 | L1 | C | C | C | H | Cl | NH₂ | H | H | 283 | 5.01ʳ |
| 1.56 | L1 | C | C | C | Cl | H | H | H | H | 265 | 6.86ˢ |
| 1.57 | L1 | C | C | C | NH₂ | H | H | Cl | H | 273 | 3.98ˢ |
| 1.59 | L1 | C | C | C | H | H | H | F | H | 272 | 5.44ʳ |
| 1.60 | L1 | C | C | C | MeO | H | H | CN | H | 275 | 5.08ˢ |
| 1.61 | L1 | C | C | C | Me | H | H | NO₂ | H | 278 | 5.44ʳ |
| 1.62 | L1 | C | C | C | H | H | H | F | H | 282 | 5.88ˢ |
| 1.63 | L1 | C | C | C | NH₂ | H | H | CO₂Me | H | 286 | 4.68ˢ |
| 1.64 | L1 | C | C | C | MeO | H | H | NO₂ | H | 296 | 5.18ˢ |
| 1.65 | L1 | C | C | C | Cl | H | H | CF₃ | H | 298 | 5.52ˢ |
| 1.66 | L1 | C | C | C | CF₃ | H | H | CF₃ | H | 325 | 5.42ˢ |
| 1.67 | L1 | C | C | C | H | H | H | H | H | 359 | 5.78ˢ |
| 2.01 | L1 | C | C | C | Cl | H | F | CO₂Me | H | 241 | 5.09ˢ |
| 2.02 | L1 | C | C | C | H | H | Cl | H | H | 291/293 | 6.48ˢ |
| 2.03 | L1 | C | C | C | H | NH₂ | Br | H | H | 2.96 | 3.51ʳ |
| 3.01 | L1 | C | C | C | H | NH₂ | H | H | H | 316/318 | 4.72ʳ |
| 4.01 | L1 | C | C | C | OMe | CH₂NH—CH₂(2-furanyl) | H | H | H | 332 | 4.10ʳ |
| 4.04 | L1 | C | C | C | H | H | H | CH₂NHCH₂(2-furanyl) | H | 362 | 4.24ʳ |
| 4.05 | L1 | C | C | C | OMe | CH₂NH—(CH₂)₂Ph | H | H | H | 356 | 4.48ˢ |
| 4.07 | L1 | C | C | C | H | H | H | CH₂NH—(CH₂)₂Ph | H | 386 | 4.70ʳ |
| 4.08 | L1 | C | C | C | OMe | CH₂NH—CH₂CH—(OH)CH₃ | H | H | H | 310 | 4.56ʳ |
| 4.09 | L1 | C | C | C | OMe | H | H | CH₂NHCH₂—CH(OH)—CH₃ | H | 340 | 3.86ʳ |
| 4.12 | L1 | C | C | C | H | CH₂NH—(n-Pr) | H | H | H | 324 | 3.72ʳ |
| 4.13 | L1 | C | C | C | MeO | H | H | CH₂NH—(n-Pr) | H | 324 | 3.98ˢ |

TABLE 1-continued

| cmpd no. | L | X³ | X⁴ | X⁵ | J² | J³ | J⁴ | J⁵ | J⁶ | M-1 found | HPLC Rt |
|---|---|---|---|---|---|---|---|---|---|---|---|
| 4.14 | L1 | C | C | C | MeO | H | H | CH₂NH-cyclopropyl | H | 322 | 3.92' |
| 4.15 | L1 | C | C | C | H | CH₂NH-cyclo-propyl | H | H | H | 292 | 3.67 |
| 4.18 | L1 | C | C | C | H | CH₂NH—CH₂CH—(OH)CH—OH | H | CH₂NH—CH₂CH—(OH)CH—OH | H | 326 | 4.17' |
| 4.19 | L1 | C | C | C | MeO | H | H | CH₂NHCH₂—CH(OH)—CH₂OH | H | 356 | 3.69' |
| 4.22 | L1 | C | C | C | H | CH₂NH—CH₂Ph | H | H | H | 342 | 4.40' |
| 4.27 | L1 | C | C | C | H | CH₂NH—(CH₂)₃Ph | H | H | H | 370 | 4.70' |
| 4.28 | L1 | C | C | C | MeO | H | H | CH₂NH—(CH₂)₃Ph | H | 400 | 4.90' |
| 4.30 | L1 | C | C | C | H | CH₂NH—n-hexyl | H | H | H | 336 | 4.69' |
| 4.32 | L1 | C | C | C | H | CH₂NH₃)₄Ph | H | H | H | 384 | 4.95' |
| 4.33 | L1 | C | C | C | H | CH₂NH—(CH₂)₃OMe | H | H | H | 324 | 3.77' |
| 4.36 | L1 | C | C | C | H | CH₂NH-isobutyl | H | H | H | 308 | 3.94' |
| 4.37 | L1 | C | C | C | OMe | H | H | CH₂NH-isobutyl | H | 338 | 4.20' |
| 4.39 | L1 | C | C | C | OMe | H | H | H | H | 324 | 3.72' |
| 4.43 | L1 | C | C | C | MeO | H | H | CH₂NHCH—(CH₂OH)Et | H | 354 | 3.96' |
| 4.46 | L1 | C | C | C | MeO | H | H | CH₂NH—(CH₂)₂—O(CH₂)₂OH | H | 370 | 3.85' |
| 4.47 | L1 | C | C | C | MeO | H | H | CH₂NHPh | H | 328 | 5.28' |
| 4.48 | L1 | C | C | C | MeO | H | H | CH₂NHPh | H | 374 | 6.10' |
| 4.49 | L1 | C | C | C | MeO | H | H | CH₂NH(4-hydroxy-phenyl) | H | 373 | 5.58' |
| 4.50 | L1 | C | C | C | MeO | H | H | CH₂NH(4-aminophenyl) | H | 415 | 4.16' |
| 4.51 | L1 | C | C | C | MeO | H | H | CH₂NH(4-acetamido-phenyl) | H | 415 | 4.28' |
| 4.52 | L1 | C | C | C | H | H | H | CH₂NH—(CH₂)₂-(4-amino-phenyl) | H | 324 | 4.29 |
| 4.53 | L1 | C | C | C | H | H | H | CH₂NH—(CH₂)₂-OEt | H | 369 | 3.82' |
| 4.54 | L1 | C | C | C | H | H | H | CH₂NH—(benzo-triazol-5-yl) | H | 372 | 5.80' |
| 4.55 | L1 | C | C | C | H | H | MeO | H | CH₂(3,4-methyl-ened ioxyaniline-N-yl) | 402 | 4.47 |
| 4.56 | L1 | C | C | C | MeO | H | H | CH₂NH-(3,4,5-trimethoxy-phenyl) | CH₂(3,4-methyl-ened ioxyaniline-N-yl) | 448 | 5.44' |
| 5.03 | L1 | C | C | C | H | H | H | H | H | 386 | 4.90' |
| 5.04 | L1 | C | N | C | H | H | H | null | H | 387 | 5.52' |
| 5.07 | L1 | C | C | C | H | C(O)NH-(2-(2-hydroxyethyl)-phenyl) | C(O)NH-(3-(hy-droxy-methyl)-phenyl) | H | H | 372 | 7.00' |
| 5.10 | L1 | C | C | C | C(O)NH-(quin-olin-3-yl) | H | H | H | H | 393 | 6.66' |
| 5.13 | L1 | C | C | C | C(O)NH-(4-hydroxy-phenyl) | H | H | H | H | 358 | 4.42' |
| 5.14 | L1 | C | C | C | C(O)(3,4-methylene-dioxy-anilinyl) | H | C(O)3,4-methyl-ened ioxy-anilinyl) | H | H | 386 | 4.62' |
| 5.15 | L1 | C | C | C | H | H | H | H | H | 386 | 5.50' |
| 5.16 | L1 | C | C | C | C(O)NH-((4-C(O)—NH₂)—C₆H₄) | H | H | H | H | 385 | 5.89' |
| 5.19 | L1 | C | C | C | C(O)NH—(CH₂)₂(tert-butyl) | H | H | H | H | 350 | 4.34' |

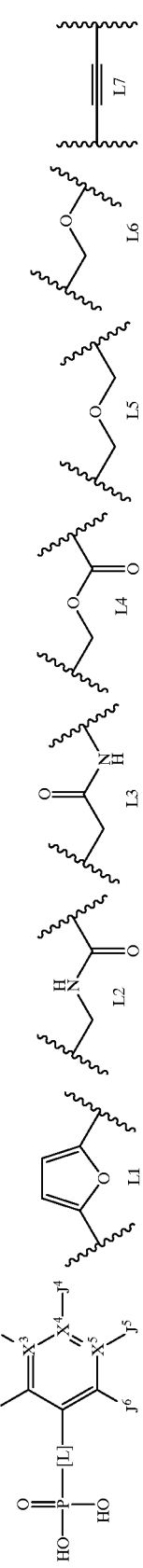

TABLE 1-continued

| cmpd no. | L | X³ | X⁴ | X⁵ | J² | J³ | J⁴ | J⁵ | J⁶ | M-1 found | HPLC Rt |
|---|---|---|---|---|---|---|---|---|---|---|---|
| 5.21 | L1 | C | C | C | C(O)NH-n-pentyl | H | H | H | H | 336 | 5.72¹ |
| 5.22 | L1 | C | C | C | C(O)NH-n-hexyl | H | H | H | H | 350 | 5.96¹ |
| 5.23 | L1 | C | C | C | C(O)NH—(CH₂)₂Ph | H | H | H | H | 370 | 5.83¹ |
| 5.27 | L1 | C | C | C | C(O)NH—(CH₂)₃Ph | H | H | H | H | 384 | 6.28¹ |
| 5.29 | L1 | C | C | C | C(O)NH—(CH₂)₄Ph | H | H | H | H | 398 | 6.70¹ |
| 5.31 | L1 | C | C | C | C(O)NH—(CH₂)₂OH | H | H | H | H | 310 | 3.57 |
| 5.33 | L1 | C | C | C | C(O)NH—(CH₂)₂O—(CH₂)₂OH | H | H | H | H | 354 | 3.84¹ |
| 5.35 | L1 | C | C | C | C(O)NH—(CH₂)₂NH₂ | H | H | H | H | 309 | 2.50¹ |
| 5.36 | L1 | C | C | C | H | C(O)NH—(CH₂)₂NH₂ | H | H | H | 309 | 3.45¹ |
| 5.38 | L1 | C | C | C | C(O)NH—(CH₂)₂-(morpholin-N-yl) | H | H | H | H | 379 | 3.26¹ |
| 5.39 | L1 | C | C | C | H | C(O)NH—(CH₂)₂-(morpholin-N-yl) | H | H | H | 379 | 3.66¹ |
| 5.40 | L1 | C | C | C | C(O)NH-piperonyl | H | H | H | H | 400 | 5.46¹ |
| 5.41 | L1 | C | C | C | H | C(O)NH-piperonyl | H | H | H | 400 | 5.82¹ |
| 5.43 | L1 | C | C | C | C(O)NHCH₂-(tetrahydro-furan-2-yl) | H | H | H | H | 350 | 5.91¹ |
| 5.44 | L1 | C | C | C | H | C(O)NH—CH₂-(tetrahydro-furan-2-yl) | H | H | H | 350 | 5.71¹ |
| 5.45 | L1 | C | C | C | H | H | C(O)NH—CH₂-(tetrahydro-furan-2-yl) | H | H | 350 | 4.58¹ |
| 5.48 | L1 | N | C | C | H | null | H | H | H | 351 | 4.16¹ |
| 5.49 | L1 | C | C | C | H | C(O)NH-(cyclo-hexyl) | H | C(O)NH—CH₂-(tetrahydro-furan-2-yl) | H | 348 | 6.40¹ |
| 5.51 | L1 | C | C | C | C(O)NH—CH₂C(O)NH₂ | H | H | H | H | 323 | 3.43¹ |
| 5.52 | L1 | C | C | C | C(O)N(Me)—CH₂-(6-methyl-2-pyridyl) | H | H | H | H | 385 | 4.14¹ |
| 5.53 | L1 | C | C | C | C(O)(morpholine amide) | H | H | H | H | 336 | 4.49¹ |
| 6.01 | L1 | C | C | C | H | NHC(O)(3-Br-phenyl) | H | CO₂Et | H | 492/494 | 6.58⁸ |
| 6.02 | L1 | C | C | C | H | NHC(O)(3-Br-phenyl) | H | CO₂-i-Pr | H | 506/508 | 6.63¹ |
| 6.03 | L1 | C | C | C | H | NHC(O)(3-Br-phenyl) | H | CO₂-n-Bu | H | 520/522 | 6.93¹ |
| 6.04 | L1 | C | C | C | H | NHC(O)(3-Br-phenyl) | H | CO₂—(CH₂)₂—OMe | H | 522/524 | 6.58¹ |
| 6.05 | L1 | C | C | C | H | NHC(O)(3-Br-phenyl) | H | CO₂—CH₂-cyclobutyl | H | 532/534 | 7.00¹ |
| 8.02 | L2 | C | C | C | H | Br | H | H | H | 292/294 | 4.58¹ |
| 8.03 | L2 | C | C | C | H | Br | MeO | H | H | 322/324 | 4.64¹ |
| 8.04 | L2 | C | C | C | H | Br | H | Br | H | 370/372/374 | 5.33¹ |
| 8.05 | L2 | C | C | Cl | H | H | H | Br | H | 326/328 | 4.88⁸ |
| 8.06 | L2 | C | C | OH | H | H | H | Cl | H | 298/300 | 5.99¹ |
| 8.07 | L2 | C | C | H | H | Br | Br | H | H | 292/294 | 4.88¹ |
| 8.08 | L2 | C | C | Me | H | Me | H | H | H | 228 | 4.36¹ |
| 8.09 | L2 | C | C | H | H | Br | Me | Br | H | 306/308 | 4.97¹ |
| 8.10 | L2 | C | C | H | H | I | H | H | H | 340 | 5.07⁴ |
| 8.13 | L2 | C | C | H | H | H | I | H | H | 340 | 5.04⁴ |

TABLE 1-continued

| cmpd no. | L | X³ | X⁴ | X⁵ | J² | J³ | J⁴ | J⁵ | J⁶ | M-1 found | HPLC Rt |
|---|---|---|---|---|---|---|---|---|---|---|---|
| 8.14 | L2 | C | C | C | H | NO₂ | H | NO₂ | H | 304 | 3.92¹ |
| 9.01 | L2 | C | C | C | NH₂ | Cl | H | H | H | 263 | 4.48¹ |
| 10.01 | L3 | C | C | C | OH | H | Br | H | H | 292/294 | 4.91¹ |
| 10.02 | L3 | C | C | C | OH | H | H | NO₂ | H | 275 | 4.54¹ |
| 10.03 | L3 | C | C | C | OH | H | H | H | H | 230 | 4.96¹ |
| 10.04 | L3 | C | C | C | H | Cl | H | Cl | H | 283 | 5.70¹ |
| 10.05 | L3 | C | C | C | Me | Me | Me | Me | H | 242 | 5.13¹ |
| 10.06 | L3 | C | C | C | H | Cl | H | H | H | 262 | 5.30¹ |
| 10.07 | L3 | C | C | C | H | I | H | H | H | 340 | 4.82¹ |
| 10.08 | L3 | C | C | C | NH₂ | H | Cl | Cl | H | 297/299 | 5.36¹ |
| 10.09 | L3 | C | C | C | H | H | F | H | H | 248 | 4.44¹ |
| 10.10 | L3 | C | C | C | H | H | Cl | H | H | 232 | 4.90¹ |
| 10.11 | L3 | C | C | C | H | H | I | H | H | 340 | 4.30¹ |
| 10.12 | L3 | C | C | C | MeO | Me | H | H | H | 279 | 5.44¹ |
| 11.01 | L4 | C | C | C | H | H | F | H | H | 229 | 5.21¹ |
| 11.03 | L4 | C | C | C | H | Me | F | Cl | H | 233 | 4.30¹ |
| 11.04 | L4 | C | C | C | MeO | H | H | H | H | 279 | 4.00¹ |
| 11.05 | L4 | C | C | C | Ph | H | H | Cl | H | 291 | 4.36¹ |
| 11.06 | L4 | C | C | C | H | H | H | Br | H | 294/296 | 6.04¹ |
| 11.07 | L4 | C | N | C | H | null | Cl | H | H | 284/286 | 4.33¹ |
| 11.08 | L4 | C | N | C | Cl | null | H | H | H | 323/325 | 3.40¹ |
| 12.01 | L4 | C | C | C | OMe | Br | Br | H | H | 309/311 | 4.93¹ |
| 13.01 | L5 | C | C | C | H | MeO | H | NO₂ | H | 291 | 5.24¹ |
| 13.02 | L5 | C | C | C | H | NO₂ | t-butyl | H | H | 258 | 4.34¹ |
| 15.01 | L6 | C | C | C | NH₂ | H | H | H | H | 258 | 4.45¹ |
| 16.01 | L7 | C | C | C | H | H | H | H | H | 181 | 3.75¹ |

TABLE 2

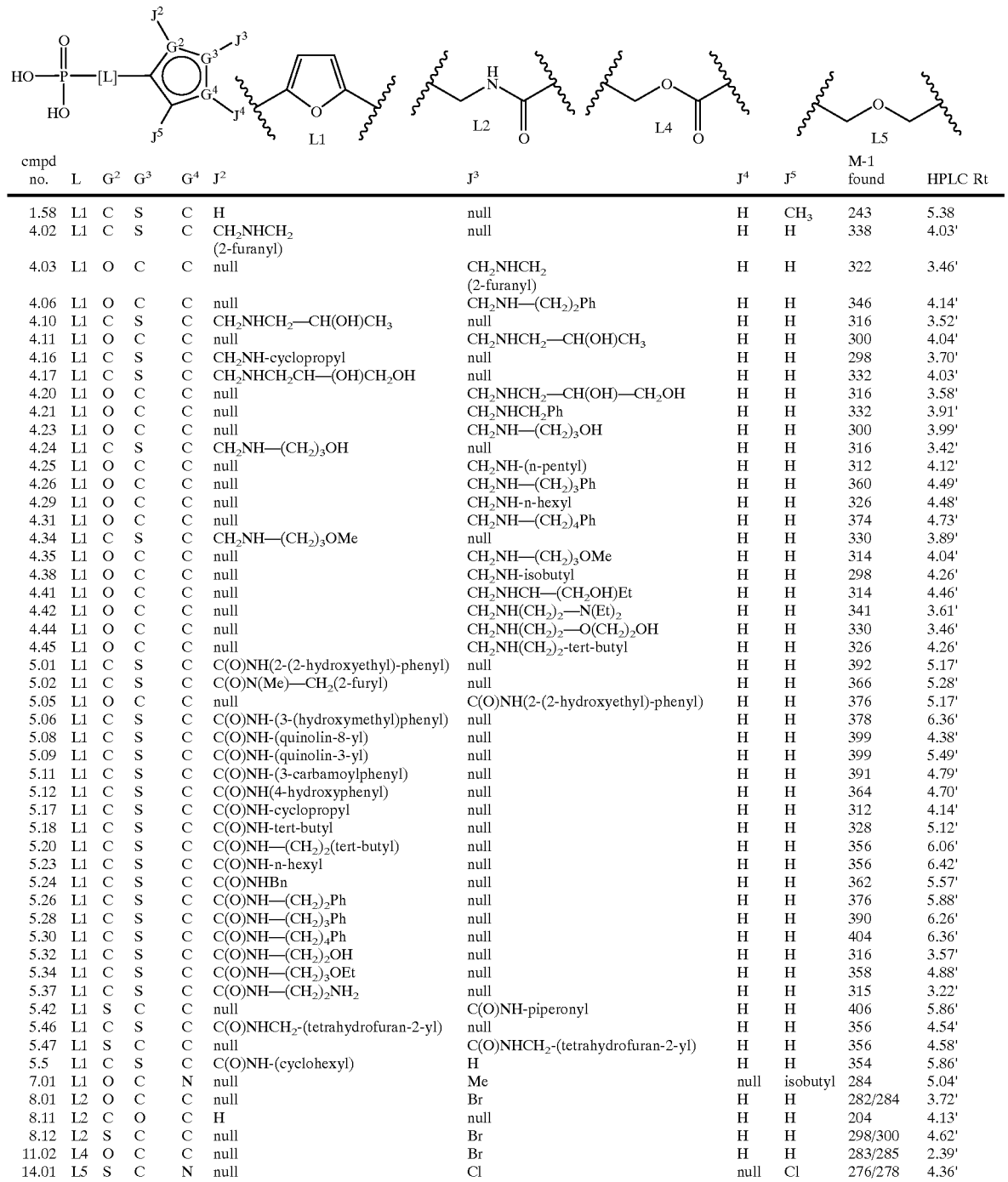

| cmpd no. | L | G² | G³ | G⁴ | J² | J³ | J⁴ | J⁵ | M-1 found | HPLC Rt |
|---|---|---|---|---|---|---|---|---|---|---|
| 1.58 | L1 | C | S | C | H | null | H | CH₃ | 243 | 5.38 |
| 4.02 | L1 | C | S | C | CH₂NHCH₂(2-furanyl) | null | H | H | 338 | 4.03' |
| 4.03 | L1 | O | C | C | null | CH₂NHCH₂(2-furanyl) | H | H | 322 | 3.46' |
| 4.06 | L1 | O | C | C | null | CH₂NH—(CH₂)₂Ph | H | H | 346 | 4.14' |
| 4.10 | L1 | C | S | C | CH₂NHCH₂—CH(OH)CH₃ | null | H | H | 316 | 3.52' |
| 4.11 | L1 | O | C | C | null | CH₂NHCH₂—CH(OH)CH₃ | H | H | 300 | 4.04' |
| 4.16 | L1 | C | S | C | CH₂NH-cyclopropyl | null | H | H | 298 | 3.70' |
| 4.17 | L1 | C | S | C | CH₂NHCH₂CH—(OH)CH₂OH | null | H | H | 332 | 4.03' |
| 4.20 | L1 | O | C | C | null | CH₂NHCH₂—CH(OH)—CH₂OH | H | H | 316 | 3.58' |
| 4.21 | L1 | O | C | C | null | CH₂NHCH₂Ph | H | H | 332 | 3.91' |
| 4.23 | L1 | O | C | C | null | CH₂NH—(CH₂)₃OH | H | H | 300 | 3.99' |
| 4.24 | L1 | C | S | C | CH₂NH—(CH₂)₃OH | null | H | H | 316 | 3.42' |
| 4.25 | L1 | O | C | C | null | CH₂NH-(n-pentyl) | H | H | 312 | 4.12' |
| 4.26 | L1 | O | C | C | null | CH₂NH—(CH₂)₃Ph | H | H | 360 | 4.49' |
| 4.29 | L1 | O | C | C | null | CH₂NH-n-hexyl | H | H | 326 | 4.48' |
| 4.31 | L1 | O | C | C | null | CH₂NH—(CH₂)₄Ph | H | H | 374 | 4.73' |
| 4.34 | L1 | C | S | C | CH₂NH—(CH₂)₃OMe | null | H | H | 330 | 3.89' |
| 4.35 | L1 | O | C | C | null | CH₂NH—(CH₂)₃OMe | H | H | 314 | 4.04' |
| 4.38 | L1 | O | C | C | null | CH₂NH-isobutyl | H | H | 298 | 4.26' |
| 4.41 | L1 | O | C | C | null | CH₂NHCH—(CH₂OH)Et | H | H | 314 | 4.46' |
| 4.42 | L1 | O | C | C | null | CH₂NH(CH₂)₂—N(Et)₂ | H | H | 341 | 3.61' |
| 4.44 | L1 | O | C | C | null | CH₂NH(CH₂)₂—O(CH₂)₂OH | H | H | 330 | 3.46' |
| 4.45 | L1 | O | C | C | null | CH₂NH(CH₂)₂-tert-butyl | H | H | 326 | 4.26' |
| 5.01 | L1 | C | S | C | C(O)NH(2-(2-hydroxyethyl)-phenyl) | null | H | H | 392 | 5.17' |
| 5.02 | L1 | C | S | C | C(O)N(Me)—CH₂(2-furyl) | null | H | H | 366 | 5.28' |
| 5.05 | L1 | O | C | C | null | C(O)NH(2-(2-hydroxyethyl)-phenyl) | H | H | 376 | 5.17' |
| 5.06 | L1 | C | S | C | C(O)NH-(3-(hydroxymethyl)phenyl) | null | H | H | 378 | 6.36' |
| 5.08 | L1 | C | S | C | C(O)NH-(quinolin-8-yl) | null | H | H | 399 | 4.38' |
| 5.09 | L1 | C | S | C | C(O)NH-(quinolin-3-yl) | null | H | H | 399 | 5.49' |
| 5.11 | L1 | C | S | C | C(O)NH-(3-carbamoylphenyl) | null | H | H | 391 | 4.79' |
| 5.12 | L1 | C | S | C | C(O)NH(4-hydroxyphenyl) | null | H | H | 364 | 4.70' |
| 5.17 | L1 | C | S | C | C(O)NH-cyclopropyl | null | H | H | 312 | 4.14' |
| 5.18 | L1 | C | S | C | C(O)NH-tert-butyl | null | H | H | 328 | 5.12' |
| 5.20 | L1 | C | S | C | C(O)NH—(CH₂)₂(tert-butyl) | null | H | H | 356 | 6.06' |
| 5.23 | L1 | C | S | C | C(O)NH-n-hexyl | null | H | H | 356 | 6.42' |
| 5.24 | L1 | C | S | C | C(O)NHBn | null | H | H | 362 | 5.57' |
| 5.26 | L1 | C | S | C | C(O)NH—(CH₂)₂Ph | null | H | H | 376 | 5.88' |
| 5.28 | L1 | C | S | C | C(O)NH—(CH₂)₃Ph | null | H | H | 390 | 6.26' |
| 5.30 | L1 | C | S | C | C(O)NH—(CH₂)₄Ph | null | H | H | 404 | 6.36' |
| 5.32 | L1 | C | S | C | C(O)NH—(CH₂)₂OH | null | H | H | 316 | 3.57' |
| 5.34 | L1 | C | S | C | C(O)NH—(CH₂)₃OEt | null | H | H | 358 | 4.88' |
| 5.37 | L1 | C | S | C | C(O)NH—(CH₂)₂NH₂ | null | H | H | 315 | 3.22' |
| 5.42 | L1 | S | C | C | null | C(O)NH-piperonyl | H | H | 406 | 5.86' |
| 5.46 | L1 | C | S | C | C(O)NHCH₂-(tetrahydrofuran-2-yl) | null | H | H | 356 | 4.54' |
| 5.47 | L1 | S | C | C | null | C(O)NHCH₂-(tetrahydrofuran-2-yl) | H | H | 356 | 4.58' |
| 5.5 | L1 | C | S | C | C(O)NH-(cyclohexyl) | H | H | H | 354 | 5.86' |
| 7.01 | L1 | O | C | N | null | Me | null | isobutyl | 284 | 5.04' |
| 8.01 | L2 | O | C | C | null | Br | H | H | 282/284 | 3.72' |
| 8.11 | L2 | C | O | C | H | null | H | H | 204 | 4.13' |
| 8.12 | L2 | S | C | C | null | Br | H | H | 298/300 | 4.62' |
| 11.02 | L4 | O | C | C | null | Br | H | H | 283/285 | 2.39' |
| 14.01 | L5 | S | C | N | null | Cl | null | Cl | 276/278 | 4.36' |

Synthesis of Compounds of Formula I

Synthesis of compounds encompassed by the present invention typically includes some or all of the following general steps as represented in the scheme below: (a) coupling of a phosphonate fragment (1a or 1b) with an aryl or heteroaryl ring fragment (2a or 2b, respectively); (b) modification of the coupled molecule if necessary; (c) deprotection of a phosphonate diester (3) to give a phosphonic acid (4) and (d) preparation of a phosphonate prodrug.

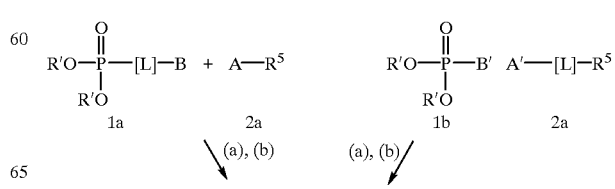

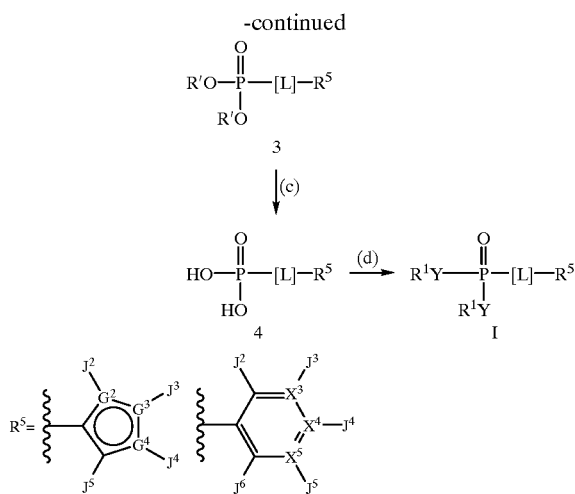

(a) Coupling of a Phosphonate Fragment (1) with an Aryl Moiety (2).

When feasible, compounds disclosed in the present invention are advantageously prepared via a convergent synthetic route entailing the coupling of a phosphonate component with an aryl or heteroaryl ring fragment.

Transition metal-catalyzed coupling reactions such as Stille and Suzuki reactions are particularly suited for the synthesis of compounds of formula I (Farina et al, *Organic Reactions*, Vol. 50; Wiley, New York, 1997; Suzuki in *Metal Catalyzed Cross-Coupling Reactions*; Wiley VCH, 1998, pp 49–97). Coupling reactions between a compound 1 (wherein B is preferably a $Bu_3Sn$) and a compound 2 (wherein A is e.g. an iodo, bromo or trifluoromethylsulfonate) under palladium-catalyzed reaction conditions to yield compounds of formula 3 wherein L is e.g. a 2,5-furanyl. The same type of coupling between a compound 1 (wherein B is preferably an iodo group) and a compound 2 (wherein A=$B(OH)_2$ or a $Bu_3Sn$) can also be used to yield compounds of formula 3 wherein L is e.g. a 2,5-furanyl.

The reactants 2 that are substituted aryl and heteroaryl compounds are either commercially available or readily synthesized using known methodology. The coupling agents 1 are also prepared using well-known chemistry. For example when L is a 2,5-furanyl, the coupling agent 1 is prepared starting from furan using organolithium techniques. Lithiation of furan using known methods (e.g. n-BuLi/TMEDA, Gschwend *Org. React.* 1979, 26: 1) followed by addition of phosphorylating agents (e.g. $ClPO_3R_2$) give 2-dialkylphosphono-furans (e.g. 2-diethylphosphonofuran). Synthesis of 2,5-disubstituted furan building blocks can be completed by lithiation of a 2-dialkylphosphonofuran (e.g. 2-diethylphosphonofuran) with a suitable base (e.g. LDA) followed by trapping of the generated anion with an electrophile (e.g. with tributyltinchloride, triisopropyl borate or iodine) to produce a 5-functionalized-2-dialkylphosphonofuran (e.g. 5-tributylstannyl-2-diethylphosphonofuran, 2-diethylphosphonofuran-5-boronic acid or 5-iodo-2-diethylphosphonofuran, respectively).

It is envisioned that the above described methods for the synthesis of furan derivatives can be either directly or with some modifications applied to syntheses of various other useful intermediates such as aryl phosphonate esters (e.g. thienyl phosphonate esters, phenyl phosphonate esters or pyridyl phosphonate esters).

Known amide bond formation reactions can be used to couple a phosphonate diester building block 1 with an aryl or heteroaryl ring intermediate 2 leading to compounds of formula I wherein L is a alkylaminocarbonyl or an alkylcarbonylamino group. For example, coupling of an aryl carboxylic acid preferably with diethyl aminomethylphosphonate can result in a compound of formula I wherein the ring fragment incorporated from intermediate 2 is an aryl and the L fragment is —$CH_2NHC(O)$—. Similarly, substitution of diethyl alkylaminoalkylphosphonates in this method may produce compounds with an L fragment represented by —R'C(R")N(R)C(O)—. Alternatively, for example, coupling of an aryl amine preferably with diethylphosphonoacetic acid can result in a compound of formula I wherein the ring fragment incorporated from intermediate 2 is an aryl and the L fragment is —$CH_2C(O)NH$—. Compounds with an L fragment of —R'C(R")C(O)NR— may be prepared by extension of this method.

Known ester bond formation reactions can be used to produce compounds of formula I wherein L is alkylcarboxy or alkoxycarbonyl (e.g. —$CH_2C(O)O$— or —$CH_2OC(O)$—). For example, when compound 2 fragment is a hydroxy substituted aryl (e.g. a phenol derivative) it can be acylated with diethylphosphonoacetyl chloride in the presence of a hindered amine such as triethylamine to produce compounds wherein L is —$CH_2C(O)O$—. Additionally, aryl-acyl halides (e.g. aryl-acyl chlorides) can be coupled to dialkyl (hydroxyalkyl)phosphonates (e.g. diethyl (hydroxy)methylphosphonate) to produce compounds wherein L is -alkoxycarbonyl- (e.g. —$CH_2OC(O)$—).

Known ether bond formation reactions can be used to produce compounds of formula I where L is an alkylene-O or an alkylene-O-alkylene group. For example, the sodium salt of a phenol may be alkylated with diethyl (iodomethyl) phosphonate or preferably diethylphosphonomethyl triflate to produce compounds of formula I where L is -alkylene-O-. Likewise, alkylation of the sodium salt of a arylmethyl alcohol with diethyl (iodomethyl)phosphonate or preferably diethylphosphonomethyl triflate may produce compounds of formula I where L is -alkylene-O-alkylene-. Alternatively, treatment of diethyl hydroxymethylphosphonate with sodium hydride and reaction of this generated sodium salt with a haloalkylaryl compound can produce compounds of formula I where L is -alkylene-O-alkylene-.

For compounds of formula I wherein L is an alkyl group, the phosphonate group can be introduced using other common phosphonate formation methods such as Michaelis-Arbuzov reaction (Bhattacharya et al., *Chem. Rev.,* 1981, 81: 415), Michaelis-Becker reaction (Blackburn et al., *J. Organomet. Chem.,* 1988, 348: 55), and addition reactions of phosphorus to electrophiles (such as aldehydes, ketones, acyl halides, imines and other carbonyl derivatives).

When feasible and sometimes advantageous, compounds of formula 3 can also be prepared from an aryl compound (2b) via the introduction of a phosphonate moiety such as a dialkylphosphono group (e.g. a diethylphosphono group). For example, compounds of formula I wherein L is a 1,2-ethynyl can be prepared via the lithiation of a terminal arylalkyne followed by reacting the anion with a phosphorylating agent (e.g. $ClPO_3R_2$) to give an arylalkynylphosphonate. The required arylalkynes are readily made using conventional chemistry. For example, arylalkynes can be derived from reactions of aryl halides (e.g. iodides, bromides) or triflates and trimethylsilylacetylene using Sonogashira reactions (Sonogashira in *Comprehensive Organic Synthesis*, Pergamon Press: New York, 1991, vol. 3, pp 521–549) followed by deprotection of the trimethylsilyl group to give terminal arylalkynes.

(b) Modification of the Coupled Molecule.

The coupled molecule 3 can be modified in a variety of ways. Aryl halides ($J^2$–$J^6$ each optionally e.g. Br, I or O-triflate) are useful intermediates and are often readily converted to other substituents such as aryls, olefins, alkyls, alkynyls, arylamines and aryloxy groups via transition metal assisted coupling reactions such as Stille, Suzuki, Heck, Sonogashira and other reactions (Farina et al, *Organic Reactions, Vol.* 50; Wiley, New York, 1997; Mitchell, *Synthesis,* 1992, 808; Suzuki in *Metal Catalyzed Cross-Coupling Reactions*; Wiley V C H, 1998, pp 49–97; *Heck Palladium Reagents in Organic Synthesis*; Academic Press: San Diego, 1985; Sonogashira in *Comprehensive Organic Synthesis*, Pergamon Press: New York, 1991, vol. 3, pp 521–549, Buchwald *J. Am. Chem. Soc.* 1999, 121, 4369–4378; Hartwig, *J. Am. Chem. Soc.* 1999, 121, 3224–3225; Buchwald *Acc. Chem. Res.* 1998, 31, 805).

Compounds of formula I wherein $J^2$–$J^6$ are each optionally is a carboxamido group can be made from their corresponding alkyl carboxylate esters via aminolysis using various amines, or by reaction of carboxylic acids with amines under standard amide bond formation reaction conditions (e.g.: DIC/HOBt mediated amide bond formation).

Compounds of formula I wherein $J^2$–$J^6$ are each optionally a carboxylate ester group can be made from the corresponding carboxylic acids by standard esterification reactions (e.g. DIEA/DMF/alkyl iodide or EDCI, DMAP and an alcohol), or from the corresponding aryl halides/triflates via transition metal-catalyzed carbonylation reactions.

Compounds of formula I wherein $J^2$–$J^6$ are each optionally is an alkylaminoalkyl or arylaminoalkyl group can be prepared from their corresponding aldehydes by standard reductive amination reactions (e.g. aryl or alkyl amine, TMOF, AcOH, DMSO, $NaBH_4$).

(c) Deprotection of a Phosphonate or Phosphoramidate Ester

Compounds of formula 4 may be prepared from phosphonate esters using known phosphate and phosphonate ester cleavage conditions. Silyl halides are generally used to cleave various phosphonate esters. When required, acid scavengers (e.g. 1,1,1,3,3,3-hexamethyldisilazane, 2,6-lutidine etc.) can be used for the synthesis of acid labile compounds. Such silyl halides include preferably bromotrimethylsilane (McKenna, et al, *Tetrahedron Lett.,* 1977, 155), chlorotrimethylsilane (Rabinowitz, *J. Org. Chem.,* 1963, 28: 2975) and iodotrimethylsilane (Blackburn, et al, *J. Chem. Soc., Chem. Commun.,* 1978, 870). Alternately, phosphonate esters can be cleaved under strong acidic conditions (e.g. HBr, HCl: Moffatt, et al, U.S. Pat. No. 3,524,846, 1970). Aryl and benzyl phosphonate esters can be cleaved under hydrogenolysis conditions (Lejczak, et al, *Synthesis,* 1982, 412; Elliott, et al, *J. Med. Chem.,* 1985, 28: 1208; Baddiley, et al, *Nature,* 1953, 171, 76).

(d) Preparation of a Phosphonate or Phosphoramidate Prodrug

The prodrug substitution can be introduced at different stages of the synthesis. Most often the prodrug is made from the phosphonic acid of formula 4 because of the instability of some of the prodrugs. Advantageously, the prodrug can be introduced at an earlier stage, provided that it can withstand the reaction conditions of the subsequent steps.

Bis-phosphoramidates, compounds of formula I wherein both Y's are nitrogen and $R^1$'s are identical groups derived from amino acids, can be prepared from compounds of formula 4 via the coupling of a suitably activated phosphonate (e.g. dichlorophosphonate) with an amino acid ester (e.g. alanine ethyl ester) with or without the presence of a base (e.g. N-methylimidazole, 4-N,N-dimethylaminopyridine). Alternatively, bis-phosphoramidates can be prepared through reactions between compounds of formula 4 with an amino acid ester (e.g. glycine ethyl ester) in the presence of triphenylphosphine and 2,2'-dipyridyl disulfide in pyridine as described in WO 95/07920 or Mukaiyama, T. et al, *J. Am. Chem. Soc.,* 1972, 94, 8528.

Mixed bis-phosphoramidates, compounds of formula I wherein both Y's are nitrogen and $R^1$'s are different groups with one $R^1$ being derived from amino acids and the other $R^1$ being either derived from amino acids or other groups (e.g. alkyl, aryl, arylalkyl amines), can be prepared by the methods described above but with sequential addition of the different amines (e.g. a glycine ethyl ester and an alanine ethyl ester) to a suitably activated phosphonates (e.g. dichlorophosphonate). It is anticipated that the mixed bis-phosphoramidates may have to be separated from other products (e.g. compounds of formula I wherein both Y's are nitrogen and $R^1$'s are identical groups) using suitable purification techniques such as column chromatography, MPLC or crystallization methods. Alternatively, mixed bis-phosphoramidates can be prepared in the following manner: coupling of an appropriate phosphonate monoester (e.g. phenyl esters or benzyl esters) with an amine (e.g. alanine ethyl ester or morpholine) via the chloridate method described above, followed by removal of the phosphonate ester (e.g. phenyl esters or benzyl esters) under conditions that the phosphoramidate bond is stable (e.g. suitable hydrogenation conditions), and the resulting mono-phosphoramidate can be coupled with a second amine (e.g. glycine ethyl ester) to give a mixed bis-phosphoramidate via the chloridate method described above. Mono esters of a phosphonic acid can be prepared using conventional methods (e.g. hydrolysis of phosphonate diesters or procedures described in EP 481 214).

Mono phosphoramidate mono esters, compounds of formula I wherein one Y is O and the other Y is N, can also be prepared using the sequential addition methods described above. For example, a dichloridate generated from compounds of formula 4 can be treated with 0.7 to 1 equivalent of an alcohol (e.g. phenol, benzyl alcohol, 2,2,2-trifluoroethanol) preferably in the presence of a suitable base (e.g. Hunig's base, triethylamine). After the above reaction is completed, 2 to 10 equivalents of an amine (e.g. alanine ethyl ester) is added to the reaction to give compounds of formula I wherein one Y is O and the other Y is N. Alternatively, selective hydrolysis (e.g. using lithium hydroxide) of a phosphonate diester (e.g. a diphenyl phosphonate) can also lead to a phosphonate mono ester (e.g. a phosphonate mono phenyl ester), and the phosphonate mono ester can be coupled with an amine (e.g. alanine ethyl ester) via the chloridate method described above for the preparation of mixed bis-phosphoramidates.

Compounds of formula 4, can be alkylated with electrophiles (such as alkyl halides, alkyl sulfonates, etc.) under nucleophilic substitution reaction conditions to give phosphonate esters. For example compounds of formula I, wherein $R^1$ are acyloxyalkyl groups can be synthesized through direct alkylation of compounds of formula 4 with an appropriate acyloxyalkyl halide (e.g. Cl, Br, I; Elhaddadi, et al *Phosphorus Sulfur,* 1990, 54(1–4): 143; Hoffmann, *Synthesis,* 1988, 62) in presence of a suitable base (e.g. N, N'-dicyclohexyl-4-morpholinecarboxamidine, Hunig's base etc.) (Starrett, et al, *J. Med. Chem.,* 1994, 1857). The carboxylate component of these acyloxyalkyl halides can be, but is not limited to, acetate, propionate, 2-methylpropionate, pivalate, benzoate, and other carboxylates. When appropriate, further modifications are envisioned after the formation of acyloxyalkyl phosphonate esters such as reduction of a nitro group. For example, compounds of formula 5 wherein $J^2$ to $J^6$ are each optionally a nitro group can be converted to compounds of formula 5 wherein $J^2$ to $J^6$ are each optionally an amino group under suitable reduction conditions (Dickson, et al, *J. Med. Chem.*, 1996, 39: 661; Iyer, et al, *Tetrahedron Lett.*, 1989, 30: 7141; Srivastva, et al, *Bioorg. Chem.*, 1984, 12: 118). Compounds of formula I wherein $R^1$ is a cyclic carbonate, a lactone or a phthalidyl group can also be synthesized via direct alkylation of compounds of formula 4 with appropriate electrophiles (e.g. halides) in the presence of a suitable base (e.g. NaH or diisopropylethylamine, Biller et al., U.S. Pat. No. 5,157,027; Serafinowska et al., *J. Med. Chem.* 1995, 38: 1372; Starrett et al., *J. Med. Chem.* 1994, 37: 1857; Martin et al., *J. Pharm. Sci.* 1987, 76: 180; Alexander et al., *Collect. Czech. Chem. Commun*, 1994, 59: 1853; EPO 0632048A1). Other methods can also be used to alkylate compounds of formula 4 (e.g. using N,N-Dimethylformamide dialkyl acetals as alkylating reagents: Alexander, P., et al *Collect. Czech. Chem. Commun.*, 1994, 59, 1853).

Alternatively, these phosphonate prodrugs can also be synthesized by reactions of the corresponding dichlorophosphonates with an alcohol (Alexander et al, *Collect. Czech. Chem. Commun.*, 1994, 59: 1853). For example, reactions of a dichlorophosphonate with substituted phenols, arylalkyl alcohols in the presence of a suitable base (e.g. pyridine, triethylamine, etc) yield compounds of formula I where $R^1$ is an aryl group (Khamnei et al., *J. Med. Chem.*, 1996, 39: 4109; Serafinowska et al., *J. Med. Chem.*, 1995, 38: 1372; De Lombaert et al., *J. Med. Chem.*, 1994, 37: 498) or an arylalkyl group (Mitchell et al., *J. Chem. Soc. Perkin Trans.* 1, 1992, 38: 2345) and Y is oxygen. The disulfide-containing prodrugs (Puech et al., *Antiviral Res.*, 1993, 22: 155) can also be prepared from a dichlorophosphonate and 2-hydroxyethyl disulfide under standard conditions. When applicable, these methods can be extended to the synthesis of other types of prodrugs, such as compounds of formula I wherein $R^1$ is a 3-phthalidyl, a 2-oxo-4,5-didehydro-1,3-dioxolanemethyl, or a 2-oxotetrahydrofuran-5-yl group.

A dichlorophosphonate or a monochlorophosphonate derivative of compounds of formula 4 can be generated from the corresponding phosphonic acids using a chlorinating agent (e.g. thionyl chloride: Starrett et al., *J. Med. Chem.*, 1994, 1857, oxalyl chloride: Stowell et al., *Tetrahedron Lett.*, 1990, 31: 3261, and phosphorus pentachloride: Quast et al., *Synthesis*, 1974, 490). Alternatively, a dichlorophosphonate can also be generated from its corresponding disilyl phosphonate esters (Bhongle et al., *Synth. Commun.*, 1987, 17: 1071) or dialkyl phosphonate esters (Still et al., *Tetrahedron Lett.*, 1983, 24: 4405; Patois et al., *Bull. Soc. Chim. Fr.*, 1993, 130: 485).

Furthermore, when feasible some of these prodrugs can be prepared using Mitsunobu reactions (Mitsunobu, *Synthesis*, 1981, 1; Campbell, *J. Org. Chem.*, 1992, 52: 6331), and other coupling reactions (e.g. using carbodiimides: Alexander et al., *Collect. Czech. Chem. Commun.*, 1994, 59: 1853; Casara et al., *Bioorg. Med. Chem. Lett.*, 1992, 2: 145; Ohashi et al., *Tetrahedron Lett.*, 1988, 29: 1189, and benzotriazolyloxytris-(dimethylamino) phosphonium salts: Campagne et al., *Tetrahedron Lett.*, 1993, 34: 6743). In some cases $R^1$ can also be introduced advantageously at an early stage of the synthesis provided that it is compatible with the subsequent reaction steps. For example, compounds of formula I where $R^1$ is an aryl group can be prepared by metalation of a 2-furanyl substituted heterocycle (e.g. using LDA) followed by trapping the anion with a diaryl chlorophosphate.

It is envisioned that compounds of formula I can be mixed phosphonate esters (e.g. phenyl and benzyl esters, or phenyl and acyloxyalkyl esters) including the chemically combined mixed esters such as the phenyl and benzyl combined prodrugs reported by Meier, et al. *Bioorg. Med. Chem. Lett.*, 1997, 7: 99.

The substituted cyclic propyl phosphonate or phosphoramidate esters can be synthesized by reactions of the corresponding dichlorophosphonate with a substituted 1,3-propanediol, 1,3-hydroxypropylamine, or 1,3-propanediamine. Some of the methods useful for preparations of a substituted 1,3-propanediol, for example, are discussed below.

Synthesis of a 1,3-propanediol, 1,3-hydroxypropylamine and 1,3-propanediarnine

Various synthetic methods can be used to prepare numerous types of 1,3-propanediols: (i) 1-substituted, (ii) 2-substituted, (iii) 1,2- or 1,3-annulated 1,3-propanediols, (iv) 1,3-hydroxypropylamine and 1,3-propanediamine. Substituents on the prodrug moiety of compounds of formula I (e.g. substituents on the 1,3-propanediol moiety) can be introduced or modified either during the synthesis of these diols, hydroxyarnines, and diamines, or after the coupling of these compounds to the compounds of formula 4.

(i) 1-Substituted 1,3-propanediols.

1,3-Propanediols useful for the synthesis of compounds in the present invention can be prepared using various synthetic methods. For example, additions of an aryl Grignard to a 1-hydroxy-propan-3-al give 1-aryl substituted 1,3-propanediols (path a). This method is suitable for the conversion of various aryl halides to 1-aryl substituted-1,3-propanediols (Coppi et. al., *J. Org. Chem.*, 1988, 53, 911). Conversions of aryl halides to 1-substituted 1,3-propanediols can also be achieved using Heck reactions (e.g. couplings with a 1,3-diox-4-ene) followed by reductions and subsequent hydrolysis reactions (Sakamoto et. al., *Tetrahedron Lett.*, 1992, 33, 6845). Various aromatic aldehydes can also be converted to 1-substituted-1,3-propanediols using alkenyl Grignard addition reactions followed by hydroboration reactions (path b). Additions of a t-butyl acetate metal enolate to aromatic aldehydes followed by reduction of the ester (path e) are also useful for the synthesis of 1,3-propanediols (Turner., *J. Org. Chem.*, 1990, 55 4744). In another method, epoxidations of cinnamyl alcohol derivatives using known methods (e.g. Sharpless epoxidations and other asymmetric epoxidation reactions) followed by a reduction reaction (e.g. using Red-Al) give various 1,3-propanediols (path c). Alternatively, enantiomerically pure 1,3-propanediols can be obtained using chiral borane reduction reactions of hydroxyethyl aryl ketone derivatives (Ramachandran et. al., *Tetrahedron Lett.*, 1997, 38 761). Propan-3-ols with a 1-heteroaryl substituent (e.g. a pyridyl, a quinolinyl or an isoquinolinyl) can be oxygenated to give 1-substituted 1,3-propanediols using N-oxide formation reactions followed by a rearrangement reaction in acetic anhydride conditions (path d) (Yamamoto et. al., *Tetrahedron*, 1981, 37, 1871).

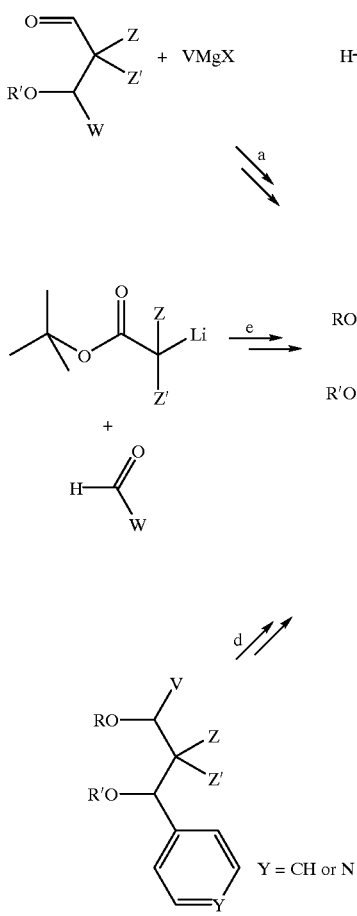

(ii) 2-Substituted 1,3-propanediols:

A variety of 2-substituted 1,3-propanediols useful for the synthesis of compounds of formula I can be prepared from 2-(hydroxymethyl)-1,3-propanediols using known chemistry (Larock, Comprehensive Organic Transformations, VCH, New York, 1989). For example, reductions of a trialkoxycarbonylmethane under known conditions give a triol via complete reduction (path a) or a bis(hydroxymethyl) acetic acid via selective hydrolysis of one of the ester group followed by reduction of the remaining two other ester groups. Nitrotriols are also known to give triols via reductive elimination (path b) (Latour et. al., Synthesis, 1987, 8, 742). Furthermore, a 2-(hydroxymethyl)-1,3-propanediol can be converted to a mono acylated derivative (e.g. acetyl, methoxycarbonyl) using an acyl chloride or an alkyl chloroformate (e.g. acetyl chloride or methyl chloroformate) (path d) using known chemistry (Greene et al., Protective groups in organic synthesis; Wiley, New York, 1990). Other functional group manipulations can also be used to prepare 1,3-propanediols such as oxidation of one the hydroxylmethyl group in a 2-(hydroxymethyl)-1,3-propanediol to an aldehyde followed by addition reactions with an aryl Grignard (path c). The intermediate aldehydes can also be converted to alkyl amines via reductive amination reactions (path e).

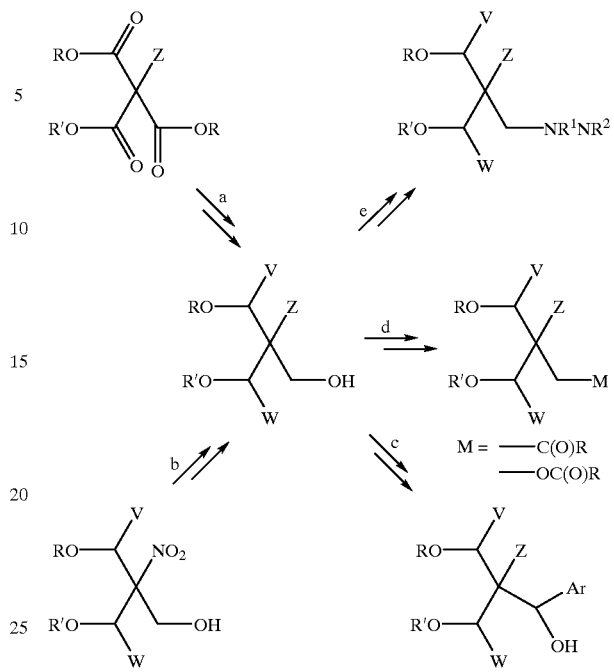

(iii) Annulated 1,3-propane Diols:

Compounds of formula I wherein V and Z or V and W are connected by four carbons to form a ring can be prepared from a 1,3-cyclohexanediol. For example, cis, cis-1,3,5-cyclohexanetriol can be modified as described for 2-substituted 1,3-propanediols. It is envisioned that these modifications can be performed either before or after formation of a cyclic phosphonate 1,3-propanediol ester. Various 1,3-cyclohexanediols can also be prepared using Diels-Alder reactions (e.g. using a pyrone as the diene: Posner et. al., Tetrahedron Lett., 1991, 32, 5295). 1,3-Cyclohexanediol derivatives are also prepared via other cycloaddition reaction methodologies. For example, cycloadditon of a nitrile oxide to an olefin followed by conversion of the resulting cycloadduct to a 2-ketoethanol derivative which can be converted to a 1,3-cylohexanediol using know chemistry (Curran, et. al., J. Am. Chem. Soc., 1985, 107, 6023). Alternatively, precursors to 1,3-cyclohexanediol can be made from quinic acid (Rao, et. al., Tetrahedron Lett., 1991, 32, 547.)

(vi) Synthesis of Chiral Substituted 1,3-hydroxyamines and 1,3-diamines:

Enantiomerically pure 3-aryl-3-hydroxypropan-1-amines are synthesized by CBS enantioselective catalytic reaction of 3-chloropropiophenone followed by displacement of halo group to make secondary or primary amines as required (Corey, et al., Tetrahedron Lett., 1989, 30, 5207). Chiral 3-aryl-3-amino propan-1-ol type of prodrug moiety may be obtained by 1,3-dipolar addition of chirally pure olefin and substituted nitrone of arylaldehyde followed by reduction of resulting isoxazolidine (Koizumi, et al., J. Org. Chem., 1982, 47, 4005). Chiral induction in 1,3-polar additions to form substituted isoxazolidines is also attained by chiral phosphine palladium complexes resulting in enantioselective formation of δ-amino alcohol (Hori, et al., J. Org. Chem., 1999; 64, 5017). Alternatively, optically pure 1-aryl substituted amino alcohols are obtained by selective ring opening of corresponding chiral epoxy alcohols with desired amines (Canas et al., Tetrahedron Lett., 1991, 32, 6931).

Several methods are known for diastereoselective synthesis of 1,3-disubstituted aminoalcohols. For example, treatment of (E)-N-cinnamyltrichloroacetamide with hypochlorus acid results in trans-dihydrooxazine which is readily hydrolysed to erythro-β-chloro-α-hydroxy-δ-phenylpropanamine in high diastereoselectivity (Commercon et al., *Tetrahedron Lett.,* 1990, 31, 3871). Diastereoselective formation of 1,3-aminoalcohols is also achieved by reductive amination of optically pure 3-hydroxy ketones (Haddad et al., *Tetrahedron Lett.,* 1997, 38, 5981). In an alternate approach, 3-aminoketones are transformed to 1,3-disubstituted aminoalcohols in high stereoselectivity by a selective hydride reduction (Barluenga et al., *J. Org. Chem.,* 1992, 57, 1219).

All the above mentioned methods can also be applied to prepare corresponding V-Z, V-W, or $V^2$-$Z^2$ annulated chiral aminoalcohols. Furthermore, such optically pure amino alcohols are also a source to obtain optically pure diamines by the procedures described earlier in the section.

Formulations

Compounds of the invention are administered orally in a total daily dose of about 0.01 mg/kg/dose to about 100 mg/kg/dose, preferably from about 0.1 mg/kg/dose to about 10 mg/kg/dose. The use of time-release preparations to control the rate of release of the active ingredient may be preferred. The dose may be administered in as many divided doses as is convenient. When other methods are used (e.g. intravenous administration), compounds are administered to the affected tissue at a rate from 0.05 to 10 mg/kg/hour, preferably from 0.1 to 1 mg/kg/hour. Such rates are easily maintained when these compounds are intravenously administered as discussed below.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Oral administration is generally preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax maybe employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions. The pharmaceutical composition can be prepared to provide easily measurable amounts for administration. For example, an aqueous solution intended for intravenous infusion should contain from about 3 to 330 $\mu$g of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of formula I when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Suitable unit dosage formulations are those containing a daily dose or unit, daily sub-dose, or an appropriate fraction thereof, of a fructose-1,6-bisphosphatase inhibitor compound.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Utility

FBPase inhibitors may be used to treat diabetes mellitus, lower blood glucose levels, and inhibit gluconeogenesis.

FBPase inhibitors may also be used to treat excess glycogen storage diseases. Excessive hepatic glycogen stores are found in patients with some glycogen storage diseases. Since the indirect pathway contributes significantly to glycogen synthesis (Shulman, G. I. *Phys. Rev.* 72:1019–1035 (1992)), inhibition of the indirect pathway (gluconeogenesis flux) decreases glycogen overproduction.

FBPase inhibitors may also be used to treat or prevent diseases associated with increased insulin levels. Increased insulin levels are associated with an increased risk of cardiovascular complications and atherosclerosis (Folsom, et al., *Stroke*, 25:66–73 (1994); Howard, G. et al., *Circulation* 93:1809–1817 (1996)). FBPase inhibitors are expected to decrease postprandial glucose levels by enhancing hepatic glucose uptake. This effect is postulated to occur in individuals that are non-diabetic (or pre-diabetic, i.e. without elevated hepatic glucose output "hereinafter HGO" or fasting blood glucose levels). Increased hepatic glucose uptake will decrease insulin secretion and thereby decrease the risk of diseases or complications that arise from elevated insulin levels.

One aspect of the invention is directed to the use of prodrugs of the novel aryl phosphonates or phosphoramidates which results in efficient conversion of the cyclic phosphonate or phosphoramidate. The cyclic 1,3-propanyl ester containing compounds are oxidized by p450 enzymes found in large amounts in the liver and other tissues containing these specific enzymes.

In another aspect of the invention, these prodrugs can also be used to prolong the pharmacodynamic half-life because the cyclic phosphonates or phosphoramidatess of the invention can prevent the action of enzymes which degrade the parent drug.

In another aspect of the invention, these prodrugs can be used to achieve sustained delivery of the parent drug because various novel prodrugs are slowly oxidized in the liver at different rates.

The novel cyclic 1,3-propanyl esters of the present invention may also be used to increase the distribution of a particular drug to the liver which contains abundant amounts of the p450 isozymes responsible for oxidizing the cyclic 1,3-propanyl ester of the present invention so that the free phosphonate or phosphoramidate is produced.

In another aspect of the invention, the cyclic phosphonate or phosphoramidate prodrugs can increase the oral bioavailability of the drugs.

Theses aspects are described in greater detail below.

Evidence of the liver specificity can also be shown in vivo after both oral and I.V. administration of the prodrugs as described in Examples G and H.

Prodrug Cleavage Mechanism of Cyclic 1,3-propanyl esters

The cyclic 1,3-propanyl ester prodrugs are rapidly cleaved in the presence of liver microsomes from rates and humans, by freshly isolated rat hepatocyles, and by cytochrome P450 inhibitors. It is believed that the isoenzyme cytochrome CYP3A4 is responsible for the oxidation based on ketoconozole inhibition of drug formation. Inhibitors of cytochrome P450 family 1 and/or family 2 do not appear to inhibit prodrug cleavage. Furthermore, although these specific prodrugs appear to be cleaved by CYP3A4, other prodrugs in the class may be substrates for other P450s.

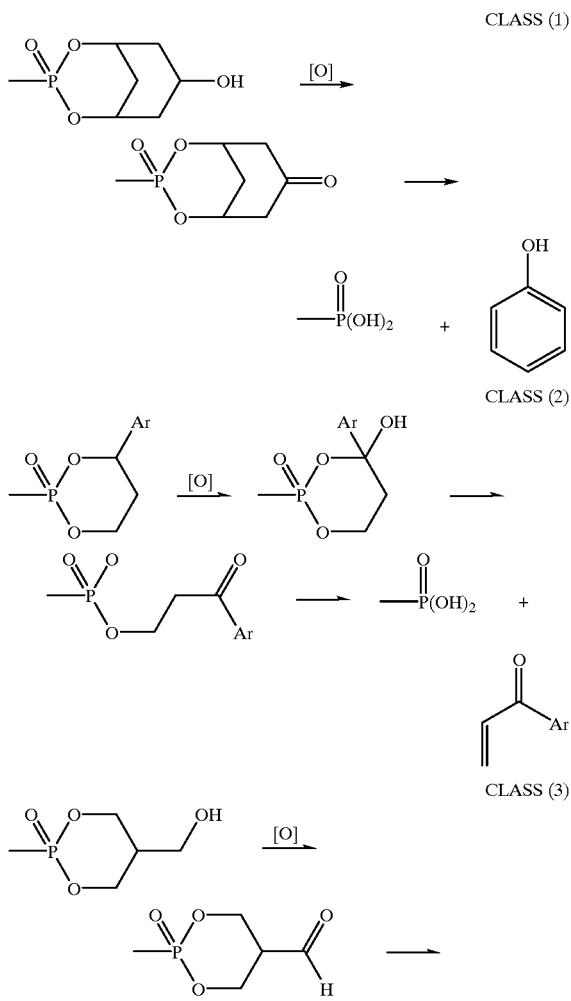

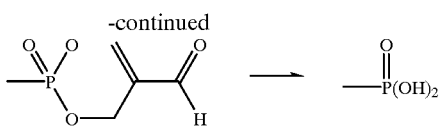

Although the cyclic 1,3-propanyl esters in the invention are not limited by the above mechanisms, in general, each ester contains a group or atom susceptible to microsomal oxidation (e.g. alcohol, benzylic methine proton), which in turn generates an intermediate that breaks down to the parent compound in aqueous solution via β-elimination of the phosphonate or phosphoramide.

Class (1) prodrugs readily undergo P450 oxidation because they have a Z'=hydroxyl or hydroxyl equivalent with an adjacent (geminal) acidic proton. D' is hydrogen to allow the ultimate elimination to produce a phenol.

Class (2) generally has V is selected from group consisting of aryl, substituted aryl, heteroaryl, substituted heteroaryl, 1-alkenyl, and 1-alkynyl. This class of prodrugs readily undergoes P450 oxidation at the benzylic methine proton (the proton on the carbon to which V is attached). The allylic proton of the case of 1-alkenyl and 1-alkynl behaves similarly. There must be a hydrogen geminal to V to undergo this oxidation mechanism. Because Z, W, and W' are not at the oxidation site in this class of prodrugs, a broad range of substituents are possible. In one aspect, Z can be an electron donating group which may reduce the mutagenicity or toxicity of the arylvinyl ketone that is the by-product of the oxidation of this class of prodrugs. Thus, in this aspect Z is —$OR^2$, —$SR^2$, or —$NR^2_2$.

In this class of prodrug, V and W may be cis to one another or trans to one another. The class (2) mechanism generally describes the oxidation mechanism for cyclic 1,3-propanyl esters wherein together V and Z are connected via an additional 3–5 atoms to form a cyclic group, optionally containing 1 heteroatom, said cyclic group is fused to an aryl group at the beta and gamma position to the Y adjacent to V.

Class (3) includes compounds wherein $Z^2$ is selected from the group consisting of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$SR^2$, —$CHR^2N_3$, —$CH_2aryl$, —$CH(aryl)OH$, —$CH(CH=CR^2_2)OH$, —$CH(C\ CR^2)OH$, and —$CH_2NHaryl$.

Class (3) prodrugs readily undergo P450 oxidation because $Z^2$ contains a hydroxyl or hydroxyl equivalent (e.g., —$CHR^2OC(O)R^3$, —$CHR^2N_3$) with an adjacent (geminal) acidic proton. $Z^2$ groups may also readily undergo P450 oxidation because they have a benzylic methine proton or equivalent (e.g., —$CH_2aryl$, —$CH(CH=CR^2_2)OH$). Where Z is —$SR^2$, it is believed that this is oxidized to the sulfoxide or sulfone which will enhance the beta-elimination step. Where $Z^2$ is —$CH_2NHaryl$, the carbon next to nitrogen is oxidized to produce a hemiaminal, which hydrolizes to the aldehyde (—C(O)H), as shown above for class (3). Because $V^2$, $W^2$, and W''' are not at the oxidation site in this class of prodrugs, a broad range of $V^2$, $W^2$, and W''' substituents is possible.

The Class (3) mechanism depicted above generally describes the oxidaton mechanism for cyclic 1,3-propanyl esters wherein together $V^2$ and $Z^2$ are connected via an additional 3–5 atoms to form a cylic group containing 5–7 atoms, optionally 1 heteroatom, substituted with hydroxy, acyloxy, alkoxycarbonyloxy, or aryloxycarbonyloxy attached to a carbon that is three atoms from both Y groups attached to the phosphorus. This class of prodrugs undergoes P450 oxidation and oxidizes by a mechanism analogous to those of class (3) described above. The broad range of W' and W groups are suitable.

The mechanism of cleavage could proceed by the following mechanisms. Further evidence for these mechanisms is indicated by analysis of the by-products of cleavage. Prodrugs of class (1) depicted where Y is —O— generate phenol whereas prodrugs of class (2) depicted where Y is —O— generate phenyl vinyl ketone.

The cyclic phosphoramidates where Y is a nitrogen rather than oxygen containing moiety can serve as a prodrug since intermediate phosphoramidates can generate the intermediate phosphonate or phosphoramidate by a similar mechanism. The phosphoramidate (—P(O)(NH$_2$)O$^-$) is then converted to the phosphonate (—PO$_3^{2-}$).

EXAMPLES

HPLC Conditions for Example Compound Characterization

HPLC was performed using a YMC ODS-Aq, Aq-303-5, 50×4.6 mm ID, S-5 μm, 120 A column with the UV detector set at 280 or 250 nm.

HPLC Elution Program: 2.5 mL/min flow rate

| Time (min) | % Acetonitrile (A) | % Buffer[a] (B) |
|---|---|---|
| 0.0 | 0 | 100 |
| 6.0 | 100 | 0 |
| 6.1 | 0 | 100 |
| 8.0 | 0 | 100 |

[a]Buffer = 95:5:0.1 water:methanol:acetic acid

Example 1

Preparation of 5-(3,5-Dinitrophenyl)-2-furanphosphonic Acid (Compound No. 1.01)

Step A. A solution of furan (1 mmole) in 1 mL diethyl ether was treated with N,N,N'N'-tetramethylethylenediamine (TMEDA) (1 mmole) and nBuLi (1.1 mmole) at –78° C. for 0.5 h. The resulting solution was cannulated into a solution of diethyl chlorophosphate (1.33 mmole) in 1 mL of diethyl ether at –60° C. and the reaction mixture allowed to rise to rt and stirred for another 16 h. Extraction and distillation at 75° C./0.2 mm produced diethyl 2-furanphosphonate as a clear oil.

Step B. A solution of diethyl 2-furanphosphonate (1 mmol) in 2 mL THF was cooled to –78° C. and added to a solution of lithium diisopropylamide (LDA) (1 mmol) in 5 mL THF at –78° C. over 20 min. The resulting mixture was stirred –78° C. for 20 min and added into a solution of tributyltin chloride (1 mmole) in 1 mL THF at –78° C. over 20 min. The mixture was then stirred at –78° C. for 15 min, and at 25° C. for 1 h. Extraction and chromatography gave diethyl 5-tributylstannyl-2-furanphosphonate as a colorless oil.

Step C. A mixture of diethyl 5-tributylstannyl-2-furanphosphonate (1 mmol), 1-iodo-2,4-dinitrobenzene (1 mmol) and tetrakis(triphenylphosphine)palladium(0) (0.05 mmol) in 6 mL of dioxane was heated at 80° C. for 16 h. Evaporation of solvent and chromatography provided diethyl 5-(3,5-dinitrophenyl)-2-furanphosphonate as solid foam.

Step D. A mixture of diethyl 5-(3,5-dinitrophenyl)-2-furanphosphonate (1 mmol) and TMSBr (6 mmol) in 10 mL of CH$_2$Cl$_2$ was stirred at rt for 16 h and then evaporated. The residue was dissolved in 85/15 CH$_3$CN/water and then the solvent evaporated. The residue was suspended in CH$_2$Cl$_2$ and the title compound (no. 1.01) was collected as a pale yellow solid: HPLC R$_t$=5.30 min; negative ion electrospray MS M–1 found: 313. The following reagents were coupled with diethyl 5-tributylstannyl-2-furanphosphonate and converted into the respective example compounds (noted in parentheses) by using Steps C and D as described in Example 1: 2-bromo-4,6-dinitroaniline (for 1.02); chloro-2-iodoanisole (for 1.03); 2,5-dichloro-1-iodobenzene (for 1.04); N1-methyl-2-iodo-4-(trifluoromethyl)benzene-1-sulfonamide (for 1.05); N1-methyl-4-chloro-2-iodobenzene-1-sulfonamide (for 1.06); N1-methyl-2-iodobenzene-1-sulfonamide (for 1.07); N1-propyl-4-chloro-2-iodobenzene-1-sulfonamide (for (1.08); 2-iodophenol (for 1.09); 5-iodo-m-xylene (for 1.10); 1-bromo-3-iodobenzene (for 1.11); 4-iodoaniline (for 1.12); 2,5-dimethoxy-4-iodochlorobenzene (for 1.13); N1-(4-chlorobenzyl)-2-iodobenzamide (for 1.14); N1-(4-chlorophenethyl)-2-iodobenzamide (for 1.15); N1-benzyl-2-iodobenzene-1-sulfonamide (for 1.16); 2-iodobenzenesulfonamide (for 1.17); 1-iodo-2,3,4,5,6-pentamethylbenzene (for 1.18); 3-iodophthalic acid (iodoethane and diisopropylamine included in Step C, for 1.19); 4-iodo-2-methylacetanilide (for 1.20); 3,5-dichloro-2-iodotoluene (for 1.21); methyl 5-hydroxy-2-iodobenzoate (for 1.22); 2-iodo-5-methylbenzamide (for 1.23); 5-hydroxy-2-iodobenzoic acid (iodoethane and diisopropylamine included in Step C, for 1.24); 1-iodo-4-nitrobenzene (for 1.25); N1-(2,4-difluorophenyl)-2-iodobenzamide (for 1.26); 3,5-dichloro-1-iodobenzene (1.27); 3-iodophenol (for 1.28); 3-bromo-5-iodobenzoic acid (for 1.29); 3-bromo-4,5-dimethoxybenzaldehyde (for 1.30); 1-iodo-2-nitrobenzene (for 1.31); 2-iodobiphenyl (for 1.32); 2-iodobenzoic acid (iodoethane and diisopropylamine included in Step C, for 1.33); 1-bromo-4-iodobenzene (for 1.34); 3'-bromopropiophenone (for 1.35); 3-bromo-4-methoxybenzonitrile (for 1.36); 1-ethyl-2-iodobenzene (for 1.37); 2-bromo-3-nitrotoluene (for 1.38); 4-iodoacetanilide (for 1.39); 2,3,4,5-tetramethyliodobenzene (for 1.40); 3-bromobiphenyl (for 1.41); 4-chloro-2-iodobenzenesulfonamide (for 1.42); N1-(4-iodophenyl)-2-tetrahydro-1H-pyrrol-1-ylacetamide (for 1.43); 3,4-dimethyliodobenzene (for 1.44); 2,4-dinitroiodobenzene (for 1.45); 3-iodobenzylamine (for 1.46); 2-fluoro-iodoaniline (for 1.47); 3-iodobenzyl alcohol (for 1.48); 2-bromo-1-iodobenzene (for 1.49); 2-bromophenethyl alcohol (for 1.50); 4-iodobenzamide (for 1.51); 4-bromobenzonitrile (for 1.52); 3-bromobenzonitrile (for 1.53); 2-bromobenzonitrile (for 1.54); 4-bromo-2-nitroaniline (for 1.55); 2-iodoisopropylbenzene (for 1.56); 6-amino-2-chloro-3-bromopyridine (derived from reaction of 6-amino-2-chlorobenzene (1 mmol) with bromine (1 mmol) in acetic acid (4 mL) for 2h at rt. followed by evaporation and chromatography to provide 6-amino-2-chloro-3-bromopyridine) (for 1.57); 3-bromo-4-methylthiophene (for 1.58); 2-bromo-4-chloroaniline (for 1.59); 1-bromo-3-chloro-5-fluoroaniline (for 1.60); 2-bromo-4-cyanoanisole (for 1.61); 2-bromo-4-nitrotoluene (for 1.62); 3-nitro-5-fluoro-1-iodobenzene (for 1.63); 2-iodo-4-carbomethoxyaniline (for 1.64); 2-bromo-4-nitroanisole (for 1.65); 2-chloro-1-iodo-5-trifluoromethylbenzene (for 1.66) and 1-bromo-2,5-bis-(trifluoromethyl)benzene (for 1.67).

Example 2

Preparation of 5-(4-Fluorophenyl)-2-furanphosphonic Acid (Compound No. 2.01)

Step A. A solution of diethyl 2-furanphosphonate (prepared as described in Step A, Example 1) (1 mmol) in 2 mL THF was cooled to −78° C. and added to a solution of lithium isopropylcyclohexylamide (LICA) (1 mmol) in 2 mL THF at −78° C. over 20 min. The resulting mixture was stirred −78° C. for 20 min and added into a solution of iodine (1 mmole) in 1 mL THF at −78° C. over 20 min. The mixture was then stirred at −78° C. for 20 min. Extraction and chromatography provided diethyl 5-iodo-2-furanphosphonate as a yellow oil.

Step B. A mixture of diethyl 5-iodo-2-furanphosphonate (1 mmol), 4-fluorophenylboronic acid (2 mmol), diisopropylethylamine (DIEA) (4 mmol) and bis(acetonitrile)dichloropalladium(II) (0.05 mmol) in 6 mL DMF was heated at 75° C. for 16 h. Extraction and chromatography provided diethyl 5-(4-fluorophenyl)-2-furanphosphonate as an oil.

Step C. Application of Step D, Example 1, to this material provided the title compound (no. 2.01) as a white solid. HPLC $R_t$=5.09 min; negative ion electrospray MS M−1 found: 241.

Substitution of 2,4-dichlorophenylboronic acid into this method provided compound no. 2.02. Substitution of 3-amino-5-carbomethoxyphenylboronic acid into this method provided compound no. 2.03.

Example 3

Preparation of 5-(4-Bromo-3-aminophenyl)-2-furanphosphonic Acid (Compound No. 3.01)

Step A. Reaction of 3-aminophenylboronic acid hydrochloride with diethyl 5-iodo-2-furanphosphonate as described in Step B of Example 2 provided diethyl 5-(3-aminophenyl)-2-furanphosphonate as an oil.

Step B. A mixture of diethyl 5-(3-aminophenyl)-2-furanphosphonate (1 mmol), NBS (0.9 mmol) and AIBN (0.1 mmol) in 30 mL of $CCl_4$ was stirred at rt for 2 h. Extraction and chromatography provided diethyl 5-(4-bromo-3-aminophenyl)-2-furanphosphonate as an oil.

Step C. Application of Step D, Example 1, to this material provided the title compound no. 3.01) as a white solid. HPLC $R_t$=4.72 min; negative ion electrospray MS M−1 found: 316/318.

Example 4

Preparation of 5-(3-(furfurylaminomethyl)phenyl)-2-furanphosphonic Acid (Compound No. 4.01)

Step A. Reaction of 3-formylphenylboronic acid with diethyl 5-iodo-2-furanphosphonate as described in Step B of Example 2 provided diethyl 5-(3-formylphenyl)-2-furanphosphonate as an oil.

Step B. A mixture of diethyl 5-(3-formylphenyl)-2-furanphosphonate (1 mmol), furfurylamine (4 mmol), trimethylorthoformate (5 mmol), acetic acid (2 mmol) in 10 mL DMSO was stirred at rt for 5h and then $NaBH_4$ (6 mmol) was added and stirring continued for a further 16 h. The solvents were evaporated and the crude product mixture containing diethyl 5-(3-(furfurylaminomethyl)phenyl)-2-furanphosphonate was used directly in the next step.

Step C. The product mixture from Step B and TMSBr (6 mmol) in 10 mL of $CH_2Cl_2$ was stirred at rt for 16 h and then evaporated. The residue was dissolved in 85/15 $CH_3CN$/water and then the solvent evaporated. The mixture was dissolved in methanol with diisopropylethylamine (2 mmol) and mixed with DOWEX® 1X8-400 formate resin for 1 h and then the mixture filtered. The resin was slurried for 15 min each with 9:1 DMSO/water, methanol, acetonitrile and 85:15 acetonitrile/water. Then the resin was mixed with 90:10 TFA/water for 1 h and then filtered. this filtrate was evaporated to provide the title compound no. 4.01) as a solid. HPLC $R_t$=4.10 min; negative ion electrospray MS M−1 found: 332.

In a similar manner the aldehydes: 3-formylphenylboronic acid, 2-methoxy-5-formylphenylboronic acid, 2-formylthiophene-3-boronic acid, 2-formylfuran-5-boronic acid, 2-formylphenylboronic acid and 2-formyl-4-methoxyphenylboronic acid were used to prepare the following compounds with respective amines indicated in parentheses: 4.02, 4.03 and 4.04 (furfiirylamine); 4.05, 4.06 and 4.07 (phenethylamine); 4.08, 4.09, 4.10 and 4.11 (1-amino-2-propanol); 4.12 and 4.13 (n-propylamine); 4.14, 4.15 and 4.16 (cyclopropylamine); 4.17, 4.18, 4.19 and 4.20 (3-amino-1,2-propanediol); 4.21 and 4.22 (benzylamine); 4.23 and 4.24 (1-amino-3-propanol); 4.25 (n-pentylamine); 4.26, 4.27 and 4.28 (phenylpropylamine); 4.29 and 4.30 (n-hexylamine); 4.31 and 4.32 (phenylbutylamine); 4.33, 4.34 and 4.35 (3-methoxypropylamine); 4.36, 4.37 and 4.38 (isobutylamine); 4.39, 4.40 and 4.41 ((+/−)-2-amino-1-butanol); 4.42 (N,N-diethylethylenediamine); 4.43 and 4.44 (2-(2-aminoethoxy)ethanol) and 4.45 (3,3-dimethylbutylamine); 4.46 and 4.47 (aniline); 4.48 (4-aminophenol); 4.49 (BOC-1,4-phenylenediamine, after reductive amination the BOC group was removed with 90/10 TFA/water), 4.50 (acetyl-1,4-phenylenediamine), 4.51 (BOC-1,4-phenylenediamine, after reductive amination the isolated product was treated with acetic anhydride and then the BOC group was removed with 90/10 TFA/water), 4.52 (ethoxyethylamine), 4.53 (5-aminobenzotriazole), 4.54 and 4.55 (3,4-methylenedioxyaniline) and 4.56 (3,4,5-trimethoxyaniline).

Example 5

Preparation of 5-(N-(2-(2-Hydroxyethyl)phenyl)thiophene-2-carboxamide-3-yl)furanphosphonic Acid (Compound No. 5.01)

Step A. A solution of 3-bromothiophene-2-carboxylic acid (1 mmol) and $SOCl_2$ (3 mmol) in 1 mL of dichloroethane was heated at 80° C. for 20 h and then the solvents evaporated. The residue was dissolved in 2 mL $CH_2Cl_2$ and mixed with triethylamine (3 mmol) and 2-(trimethylsilyl)ethanol (1.3 mmol) at rt for 12 h. Extractive isolation provided 2-(trimethylsilyl)ethyl 3-bromo-2-thiophenecarboxylate as an oil.

Step B. A mixture of diethyl 5-tributylstannyl-2-furanphosphonate (1 mmol) and 2-(trimethylsilyl)ethyl 3-bromo-2-thiophenecarboxylate (1.2 mmol) were coupled as described in Step C of Example 1 to provide diethyl 5-(2-(carbo(2-trimethylsilylethoxy))-3-thienyl)-2-furanphosphonate as an oil.

Step C. A solution of diethyl 5-(2-(carbo(2-trimethylsilylethoxy))-3-thienyl)-2-furanphosphonate (1 mmol) and tetrabutylammonium fluoride (1.5 mmol) in 6 mL of THF was stirred at rt for 16 h. Extractive isolation provided diethyl 5-(2-carboxy-3-thienyl)-2-furanphosphonate as an oil.

Step D. A mixture of diethyl 5-(2-carboxy-3-thienyl)-2-furanphosphonate (1 mmol), 2-(2-hydroxyethyl)aniline (1.5 mmol), 1-(3-dimethylaminopropyl)-3-ethylcarbodiimide hydrochloride (EDC) (1.5 mmol) and 1-hydroxybenzotriazole hydrate (HOBt) (1.5 mmol) in 8 mL of DMF was stirred for 16 h at rt. Extraction and chromatography provided diethyl 5-(N-(2-(2-hydroxyethyl)phenyl)thiophene-2-carboxamide-3-yl)furanphosphonate as an oil.

Step E. Diethyl 5-(N-(2-(2-hydroxyethyl)phenyl)thiophene-2-carboxamide-3-yl)furanphosphonate was deesterified with TMSBr as described in Step D, Example 1, to provide the title compound (no. 5.01) as a solid. HPLC $R_t$=5.17 min; negative ion electrospray MS M−1 found: 392.

In a similar manner the carboxylic acids: 2-iodobenzoic acid, 3-iodobenzoic acid, 4-iodobenzoic acid, 3-bromothiophene-2-carboxylic acid, 5-bromo-2-furoic acid, 3-bromothiophene-2-carboxylic acid, 5-bromothiophene-2-carboxylic acid and 5-bromonicotinic acid were used to prepare the following compounds with respective amines indicated in parentheses: 5.02 (N-methylfurfurylamine); 5.03, 5.04, 5.05 (2-(2-hydroxyethyl)aniline); 5.06 and 5.07 (3-hydroxymethylaniline); 5.08 (8-aminoquinoline); 5.09 and 5.10 (3-aminoquinoline); 5.11 (3-aminobenzamide); 5.12, 5.13 (4-aminophenol); 5.14 and 5.15 (3,4-methylenedioxyaniline); 5.16 (4-aminobenzamide); 5.17 (cyclopropylamine); 5.18 (t-butylamine); 5.19, 5.20 (3,3-dimethylbutylamine); 5.21 (n-pentylamine); 5.22 and 5.23 (n-hexylamine); 5.24 (benzylamine); 5.25, 5.26 (phenethylamine); 5.27 and 5.28 (phenpropylamine); 5.29 and 5.30 (phenbutylamine); 5.31 and 5.32 (ethanolamine); 5.33 (2-(2-aminoethoxy)ethanol); 5.34 (3-ethoxypropylamine); 5.35, 5.36 and 5.37 (ethylenediamine mono-boc amide); 5.38, 5.39 4-(2-aminoethyl)morpholine); 5.40, 5.41 and 5.42 (piperonylamine); 5.43, 5.44, 5.45, 5.46, 5.47 and 5.48 (tetrahydrofurfurylamine); 5.49 and 5.50 (cyclohexylamine); 5.51 (2-aminoacetamide); 5.52 (6-methyl-2-picolylmethylamine) and 5.53 (morpholine).

Example 6

Preparation of 1-(3-Bromophenylcarbamoyl)-3-carboethoxy-6-(2-phosphonofuran-5-yl)benzene (Compound No. 6.01)

Step A. A mixture of 3-carboxy-5-nitrophenylboronic acid (1 mmol), diethyl 5-iodo-2-furanphosphonate (1.5 mmol) and tetrakistriphenylphosphinepalladium(0) (0.05 mmol) were dissolved in 1.5 mL of 1,4-dioxane and 0.25 mL of DMF. After bubbling $N_2$ into this solution for 5 min then 1.5 mL of 1 M aqueous $K_3PO_4$ were added. After $N_2$ bubbling for 5 min the mixture was heated at 85° C. for 14 h and then cooled and diluted with EtOAc and water. The layers were separated, the EtOAc layer extracted with water. The aqueous layers were combined, pH lowered to pH 2 and then extracted with EtOAc. The EtOAc extract was dried ($MgSO_4$) and evaporated. Chromatography on silica gel provided 1-nitro-3-carboxy-5-(diethyl 2-phosphonofuran-5-yl)benzene.

Step B. A mixture of 1-nitro-3-carboxy-5-(diethyl 2-phosphonofuran-5-yl)benzene (1 mmol), trimethylsilylethanol (1 mmol), EDCI (1.1 mmol) and DMAP (0.1 mmol) were stirred in 2 mL of $CH_2Cl_2$ at rt for 16 h. Extractive isolation provided 1-nitro-3-carbotrimethylsilylethoxy-5-(diethyl 2-phosphonofuran-5-yl)benzene.

Step C. A mixture of 1-nitro-3-carbotrimethylsilylethoxy-5-(diethyl 2-phosphonofuran-5-yl)benzene (1 mmol) and 10% Pd/C (80 mg) in 10 mL of EtOAc and 5 mL of MeOH was stirred at rt under an atmosphere of hydrogen for 6 h. The mixture was filtered over Celite and purified by silica gel chromatography to provide 1-amino-3-carbotrimethylsilylethoxy-5-(diethyl 2-phosphonofuran-5-yl)benzene.

Step D. A mixture of 1-amino-3-carbotrimethylsilylethoxy-5-(diethyl 2-phosphonofuran-5-yl)benzene (1 mmol), 3-bromobenzoyl chloride (4 mmol) and triethylamine (4.5 mmol) in 30 mL of $CH_2Cl_2$ was stirred at rt for 4 h. Then 5 mL of water was added and after stirring for 30 min the mixture was evaporated. The residue was dissolved in MeOH and slurried with 5 g of DOWEX 1X8-400 carbonate resin. The mixture was filtered and the solvent evaporated to provide 1-(3-bromophenylcarbamoyl)-3-carbotrimethylsilylethoxy-5-(diethyl 2-phosphonofuran-5-yl)benzene.

Step E. A mixture of 1-(3-bromophenylcarbamoyl)-3-carbotrimethylsilylethoxy-5-(diethyl 2-phosphonofuran-5-yl)benzene (1 mmol) and 4.5 mL of a 1 M solution of $Bu_4NF$ in THF were stirred in 10 mL of THF for 6 h at rt. To this mixture was added 5 grams of DOWEX 50WX8-400 free acid and 5 grams of DOWEX 50WX8-400 sodium salt. After slurrying this mixture for 14 h the mixture was filtered and the filtrate evaporated to provide 1-(3-bromophenylcarbamoyl)-3-carboxy-5-(diethyl 2-phosphonofuran-5-yl)benzene.

Step F. A mixture of 1-(3-bromophenylcarbamoyl)-3-carboxy-5-(diethyl 2-phosphonofuran-5-yl)benzene (1 mmol), EDCI (2 mmol), DMAP (0.1 mmol) and ethanol (1.5 mmol) in 70 mL of $CH_2Cl_2$ were stirred at rt for 14 h. After evaporation the mixture was redissolved in MeOH and slurried with 5 g of DOWEX 50WX8-400 free acid and 5 g of DOWEX 1X8-400 bicarbonate resin for 4 h and then filtered. The filtrate was evaporated to provide 1-(3-bromophenylcarbamoyl)-3-carboethoxy-5-(diethyl 2-phosphonofuran-5-yl)benzene.

Step G. Application of Step D, Example 1, to this material provided the title compound (no. 6.01) as a white solid. HPLC $R_t$=6.58 min; negative ion electrospray MS M−1 found: 492/494.

In a similar manner, the following compounds were prepared: 6.02, 6.03, 6.04 and 6.05.

Example 7

Preparation of 2-Methyl-4-isobutyl-5-12-(5-phosphono)furanylloxazole (Compound No. 7.01)

Step A. A solution of 5-diethylphosphono-2-[(4-methyl-1-oxo)pentyl]furan (1 mmole) and cupric bromide (3.5 mmole) in ethanol was refluxed for 2 h. The reaction mixture was cooled to room temperature, then filtered. Evaporation and chromatography gave 5-diethylphosphono-2-[(2-bromo-4-methyl-1-oxo)pentyl]furan.

Step B. A solution of 5-diethylphosphono-2-[(2-bromo-4-methyl-1-oxo)pentyl]furan (1 mmole) in acetic acid was treated with sodium acetate (2 mmole) and ammonium acetate (2 mmole) at 100° C. for 4 h. Evaporation and chromatography gave 2-methyl-4-isobutyl-5-[2-(5-diethylphosphono)furanyl]oxazole as an oil.

Step C. The compound 2-methyl-4-isobutyl-5-[2-(5-diethylphosphono)furanyl]oxazole was deesterified with TMSBr as described in Step D, Example 1, to provide the title compound (no. 7.01) as a solid. HPLC $R_t$=5.04 min; negative ion electrospray MS M−1 found: 284.

Example 8

Preparation of N-(Phosphonomethyl)-5-bromofuran-2-carboxamide (Compound No. 8.01)

5-Bromofuroic acid was reacted with diethyl aminomethylphosphonate in a manner similar to that described in Step D, Example 5. The product was treated with TMSBr as described in Step D, Example 1 to provide the title compound (no. 8.01) as a solid. HPLC $R_t$=3.72 min; negative ion electrospray MS M−1 found: 282/284.

This method was used with the following reagents to prepare the respective compounds (in parentheses): 3-bromobenzoic acid (for 8.02); 3-bromo-4-methoxybenzoic acid (for 8.03); 3,5-dibromobenzoic acid (for 8.04); 5-bromo-2-chlorobenzoic acid (for 8.05); 3,5-dichloro-2-hydroxybenzoic acid (for 8.06); 4-bromobenzoic acid (for 8.07); 4-toluic acid (for 8.08); 4-bromo-2-methylbenzoic acid (for 8.09); 4-iodobenzoic acid (for 8.10); 3-furoic acid (for 8.11); 5-bromothiophene-2-carboxylic acid (for 8.12), 3-iodobenzoic acid (for 8.13) and 3,5-dinitrobenzoic acid (for 8.14).

Example 9

Preparation of N-(Diethylphosphonomethyl)-2-amino-3-chlorobenzamide (Compound No. 9.01)

Step A. To a solution of 3-chloro-2-nitrobenzoic acid (1 mmol) and aminomethylenediethyl phosphonate (1.1 mmol) in dichloromethane (5 mL) was added diisopropylethylamine (5 mmol) followed by pyBOP (1.5 mmol). The reaction was stirred at room temperature for 3 h and concentrated. The mixture was purified by chromatography to yield N-(diethylphosphonomethyl)-2-nitro-3-chlorobenzamide as a solid.

Step B. To a solution of N-(diethylphosphonomethyl)-2-nitro-3-chlorobenzamide (1 mmol) in methanol (10 mL) was added sodiumdithionite (3 mmol) and the mixture stirred for 1 h and concentrated. The mixture was extracted and chromatographed to result in N-(diethylphosphonomethyl)-2-amino-3-chlorobenzamide.

Step C. The compound N-(diethylphosphonomethyl)-2-amino-3-chlorobenzamide was deesterified with TMSBr as described in Step D, Example 1, to provide the title compound (no. 9.01) as a solid. HPLC $R_t$=4.48 min; negative ion electrospray MS M−1 found: 263.

Example 10

Preparation of N-(4-Bromophenyl)phosphonomethylcarboxamide (Compound No. 10.01)

4-Bromoaniline was reacted with diethylphosphonoacetic acid in a manner similar to that described in Step D, Example 5. The product was treated with TMSBr as described in Step D, Example 1 to provide the title compound (no. 10.01) as a solid. HPLC $R_t$=4.91 min; negative ion electrospray MS M−1 found: 292/294.

This method was used with the following reagents to prepare the respective compounds (in parentheses): 2-hydroxy-5-nitroaniline (for 10.02); 2-hydroxyaniline (for 10.03); 3,5-dichloroaniline (for 10.04); 3,5-dimethylaniline (for 10.05); 3-chloro-4-methylaniline (for 10.06); 3-chloroaniline (for 10.07); 3-iodoaniline (for 10.08); 4,5-dichloro-1,2-phenylenediamine (for 10.09); 4-chloroaniline (for 10.10); 4-fluoroaniline (for 10.11) and 4-iodoaniline (for 10.12).

Example 11

Preparation of Phosphonomethyl 4-Chloro-2-methoxybenzoate (Compound No. 11.01)

Step A. A mixture of 4-chloro-2-methoxybenzoic acid (1 mmol), oxalyl chloride (1 mmol) and DMF (0.05 mmol) in 2 mL of $CH_2Cl_2$ was stirred at rt for 6 h and then evaporated. To the residue was added 2 mL of $CH_2Cl_2$, triethylamine (2 mmol) and diethyl (hydroxymethyl)phosphonate (0.33 mmol) and this mixture was stirred at rt for 16 h and then diluted with water and $CH_2Cl_2$. The organic layer was dried ($MgSO_4$) and evaporated. Purification of the residue by silica gel chromatography provided diethylphosphonomethyl 4-chloro-2-methoxybenzoate as an oil.

Step B. This compound was deesterified with TMSBr as described in Step D, Example 1, to provide the title compound (no. 11.01) as a solid. HPLC $R_t$=5.21 min; negative ion electrospray MS M−1 found: 279.

The following compounds were prepared in the same manner from their respective carboxylic acids indicated in parentheses: 11.02 (5-bromo-2-furoic acid); 11.03 (3-toluic acid); 11.04 (4-fluorobenzoic acid); 11.05 (5-chloro-2-methoxybenzoic acid); 11.06 (2-biphenylcarboxylic acid); 11.07 (3-bromo-5-carboxypyridine) and 11.08 (2,6-dichloronicotinic acid).

Example 12

Preparation of Phosphonomethyl 3-Bromo-2-methoxybenzoate (Compound No. 12.01)

Step A. A mixture of diethyl (hydroxymethyl) phosphonate (1.2 mmol), 2-anisoyl chloride (1 mmol) and pyridine (2 mmol) in 5 mL $CH_2Cl_2$ were stirred at rt for 4 h. Extraction and chromatography provided diethylphosphonomethyl 2-methoxybenzoate as an oil.

Step B. A mixture of diethylphosphonomethyl 2-methoxybenzoate (1 mmol) and bromine (100 mmol) in 10 mL $CHCl_3$ was stirred at rt for 16 h. Extraction and chromatography provided diethylphosphonomethyl 3-bromo-2-methoxybenzoate as an oil.

Step C. This compound was deesterified with TMSBr as described in Step D, Example 1, to provide the title compound (no. 12.01) as a solid. HPLC $R_t$=4.93 min; negative ion electrospray MS M−1 found: 323/325.

Example 13

Preparation of 4-Bromo-3-methoxyphenylmethoxymethylphosphonic Acid (Compound No. 13.01)

Step A. A mixture of 3-methoxybenzyl alcohol (1 mmol) and sodium hydride (1.5 mmol) in 5 mL DMF was stirred at rt for 1 h and then added via cannula to a solution of diethylphosphonomethyl triflate (1 mmol) in 5 mL of DMF and the resulting mixture stirred at rt for 16 h. Extraction and chromatography provided diethyl 3-methoxyphenylmethoxymethylphosphonate as an oil.

Step B. Reaction of diethyl 3-methoxyphenylmethoxymethylphosphonate and bromine as described in Step 2 of Example 10 provided diethyl 4-bromo-3-methoxyphenylmethoxymethylphosphonate as an oil.

Step C. This compound was deesterified with TMSBr as described in Step D, Example 1, to provide the title compound (no. 187) as a solid. HPLC $R_t$=5.24 min; negative ion electrospray MS M−1 found: 309/311.

Compound 13.02 was prepared similarly from 3,5-dinitrobenzyl alcohol.

Example 14

Preparation of 2,4-Dichloro-5-(phosphonomethoxymethyl)thiazole (Compound No. 14.01)

Step A. To a solution of 2,4-dichloro-5-(hydroxymethyl)thiazole (*J. Chem. Soc. Perkin I* 1992, 973) (1 mmol) in dichloromethane at 0° C. was added 1M phosphorus tribromide in dichloromethane (1.1 mmol) and the mixture allowed to stir at rt for 1 h. The product 2,4-dichloro-5-(bromomethyl)thiazole was extracted and purified by column chromatography.

Step B. To a solution of diethyl hydroxymethylphosphonate (1.2 mmol) in THF (10 mL) at 0° C. was added 60% sodium hydride (1.1 mmol) and allowed to stir for 15 minutes before adding 2,4-dichloro-5-(bromomethyl)thiazole (1 mmol). The mixture was warmed to room temperature and allowed to stir for 3 h. The reaction was extracted and chromatographed to yield 2,4-dichloro-5-(diethylphosphonomethoxymethyl)thiazole.

Step C. 2,4-Dichloro-5-(diethylphosphonomethoxymethyl)thiazole was deesterified with TMSBr as described in Step D, Example 1, to provide the title compound (no. 14.01) as a solid. HPLC $R_t$=4.36 min; negative ion electrospray MS M−1 found: 276/278.

Example 15

Preparation of 2-Amino-4-tert-butyl-1-phosphonomethoxybenzene (Compound No. 15.01)

Step A. A solution of 2-amino-4-tert-butylphenol (1 mmole) in DMF was treated with sodium hydride (1.2 mmole) and trifluoromethanesulfonic acid 2-diethylphosphonomethyl ester (1.2 mmole) at room temperature for 6 h. Evaporation and chromatography gave 2-amino-4-tert-butyl-1-diethylphosphonomethoxybenzene as an oil.

Step B. The compound 2-amino-4-tert-butyl-1-diethylphosphonomethoxybenzene was deesterified with TMSBr as described in Step D, Example 1, to provide the title compound (no. 15.01) as a solid. HPLC $R_t$=4.45 min; negative ion electrospray MS M−1 found: 258.

Example 16

Preparation of 1-Phosphono-2-phenylacetylene (Compound No. 16.01)

Step A. A solution of iodobenzene (1 mmole) in DMF (5 mL) was treated with trimethylsilylacetylene (2 mmole), Pd(PPh$_3$)$_2$Cl$_2$ (0.035 mmole), CuI (0.08 mmole) and triethylamine (4 mmole), and the resulting reaction mixture was stirred under nitrogen at room temperature for 5 h. Evaporation followed by chromatography gave 1-trimethylsilyl-2-phenylacetylene as a solid.

Step B. A solution of 1-trimethylsilyl-2-phenylacetylene (1 mmole) in anhydrous THF (5 mL) was treated with a solution of tetrabutylammonium fluoride (1.5 mmole) at 0° C. for 1 h. Extraction and chromatography gave phenylacetylene.

Step C. A solution of phenylacetylene (1 mmole) in anhydrous THF (5 mL) was treated with TMEDA (1.2 mmole) followed by n-BuLi (1.2 mmole) at −78° C. After 30 min the reaction was treated with diethyl chlorophosphate, and the resulting solution was stirred at −78° C. for 1 h. The reaction was quenched with saturated ammonium chloride. Extraction and chromatography gave 1-diethylphosphono-2-phenylacetylene as an oil.

Step D. 1-Diethylphosphono-2-phenylacetylene was deesterified with TMSBr as described in Step D, Example 1, to provide the title compound (no. 16.01) as a solid. HPLC $R_t$=3.75 min; negative ion electrospray MS M−1 found: 181.

Example 17

General Procedure for Preparation of Bis-phosphoroamide Prodrugs

Step A. Dichloridate formation. To a suspension of 1 mmol of phosphonic acid in 5 mL of dichloroethane is added 0.1 mmol of pyridine (or 0.1 mmol of DMF) followed by 6 mmol of thionyl chloride and it is heated to reflux for 2.5 h. Solvent and excess thionyl chloride are removed under reduced pressure and dried to give the dichloridate.

Step B. Coupling reaction.

Method 1: To a solution of the crude dichloridate in 5 mL of dry CH$_2$Cl$_2$ is added 8 mmol of aminoacid ester at 0° C. The resultant mixture is allowed to come to rt where it is stirred for 16 h. The reaction mixture is subjected to extractive work up and chromatography to provide the target bisphosphoramide.

Method 2: To the crude dichloridate in 5 mL of dry CH$_2$Cl$_2$ is added 4 mmol of aminoacid ester and 4 mmol of N-methylimidazole at 0° C. The resultant mixture is allowed to come to rt where it is stirred for 16 h. The reaction mixture is subjected to extractive work up and chromatography to provide the target bisphosphoramide.

Example 18

General Procedure for Mixed Bis-phosphoroamidate Prodrugs

To a solution of crude dichloridate (1 mmol, prepared as described in Step A in Example 15) in 5 mL of dry CH$_2$Cl$_2$ is added an amine (1 mmol) followed by 4-dimethylaminopyridine (3 mmol) at 0° C. The resulting mixture is allowed to warm to room temperature and stir for 1 h. The reaction is cooled back to 0° C. before adding an aminoacid ester (2 mmol) and then is left at room temperature for 16 h. The reaction mixture is subjected to extractive work up and the mixed bis-phosphoroamidate prodrug is purified by column chromatography.

BIOLOGICAL EXAMPLES

Example A

Inhibition of Human Liver FBPase

E. coli strain BL21 transformed with a human liver FBPase-encoding plasmid was obtained from Dr. M. R. El-Maghrabi at the State University of New York at Stony Brook. The enzyme was typically purified from 10 liters of recombinant E. coli culture as described (M. Gidh-Jain et al., 1994, The Journal of Biological Chemistry 269, pp 27732–27738). Enzymatic activity was measured spectrophotometrically in reactions that coupled the formation of product (fructose-6-phosphate) to the reduction of dimethylthiazoldiphenyltetrazolium bromide (MTT) via NADP$^+$ and phenazine methosulfate (PMS), using phosphoglucose isomerase and glucose 6-phosphate dehydrogenase as the coupling enzymes. Reaction mixtures (200 μl) were made up in 96-well microtitre plates, and consisted of 50 mM Tris—HCl, pH 7.4, 100 mM KCl, 5 mM EGTA, 2 mM MgCl$_2$, 0.2 mM NADP, 1 mg/ml BSA, 1 mM MTT, 0.6 mM PMS, 1 unit/ml phosphoglucose isomerase, 2 units/ml glucose 6-phosphate dehydrogenase, and 0.150 mM substrate (fructose-1,6-bisphosphate). Inhibitor concentrations were varied from 0.01 μM to 10 μM. Reactions were started by the addition of 0.002 units of pure hlFBPase, and were monitored for 7 minutes at 590 nm in a Molecular Devices Plate Reader (37° C.).

Table 3 below provides the IC$_{50}$ values for several compounds prepared. The IC$_{50}$ for AMP is 1 μM.

TABLE 3

| Compound No. | Human Liver FBPase IC$_{50}$ ($\mu$M) |
| --- | --- |
| 1.01 | 0.31 |
| 1.02 | 1.8 |
| 1.03 | 0.50 |
| 2.01 | 2.2 |
| 2.02 | 3 |
| 2.03 | 2.6 |
| 3.01 | 5.5 |
| 4.46 | 3 |
| 4.48 | 0.14 |
| 4.49 | 0.32 |
| 4.50 | 6.5 |
| 4.51 | 12 |
| 8.01 | 4 |
| 8.14 | 4 |
| 9.01 | 60 |
| 11.01 | 2.8 |
| 11.02 | 6.4 |
| 12.01 | 4.2 |
| 13.01 | 11 |
| 13.02 | 9 |
| 16.01 | 89 |

Inhibition of Rat Liver FBPase

*E. coli* strain BL21 transformed with a rat liver FBPase-encoding plasmid is obtained from Dr. M. R. El-Maghrabi at the State University of New York at Stony Brook. Recombinant FBPase is purified as described (El-Maghrabi, M. R., and Pilkis, S. J. (1991) *Biochem. Biophys. Res. Commun.* 176, 137–144) The enzyme assay is identical to that described above for human liver FBPase. The IC$_{50}$ for AMP is 20 $\mu$M.

Example B

AMP Site Binding

To assess whether compounds bind to the allosteric AMP binding site of hlFBPase, the enzyme is incubated with radio-labeled AMP in the presence of a range of test compound concentrations. The reaction mixtures consist of 25 mM$^3$H-AMP (54 mCi/mmole) and 0–1000 mM test compound in 25 mM Tris-HCl, pH 7.4, 100 mM KCl and 1 mM MgCl$_2$. 1.45 mg of homogeneous FBPase (±1 nmole) is added last. After a 1 minute incubation, AMP bound to FBPase is separated from unbound AMP by means of a centrifugal ultrafiltration unit ("Ultrafree-MC", Millipore) used according to the instructions of the manufacturer. The radioactivity in aliquots (100 $\mu$l) of the upper compartment of the unit (the retentate, which contains enzyme and label) and the lower compartment (the filtrate, which contains unbound label) is quantified using a Beckman liquid scintillation counter. The amount of AMP bound to the enzyme is estimated by comparing the counts in the filtrate (the unbound label) to the total counts in the retentate.

Example C

AMP Site/Enzyme Selectivity

To determine the selectivity of compounds towards FBPase, effects of FBPase inhibitors on 5 key AMP binding enzymes is measured using the assays described below:
*Adenosine Kinase*: Human adenosine kinase is purified from an *E. coli* expression system as described by Spychala et al. (Spychala, J., Datta, N. S., Takabayashi, K., Datta, M., Fox, I. H., Gribbin, T., and Mitchell, B. S. (1996) *Proc. Natl. Acad. Sci. USA* 93, 1232–1237). Activity was measured essentially as described by Yamada et al. (Yamada, Y., Goto, H., Ogasawara, N. (1988) *Biochim. Biophys. Acta* 660, 36–43.) with a few minor modifications. Assay mixtures contain 50 mM TRIS-maleate buffer, pH 7.0, 0.1% BSA, 1 mM ATP 1 mM MgCl$_2$, 1.0 $\mu$M [U-$^{14}$C] adenosine (400–600 mCi/mmol) and varying duplicate concentrations of inhibitor. $^{14}$C-AMP was separated from unreacted $^{14}$C-adenosine by absorption to anion exchange paper (Whatman) and quantified by scintillation counting.

Adenosine Monophosphate Deaminase: Porcine heart AMPDA is purified essentially as described by Smiley et al. (Smiley, K. L., Jr, Berry, A. J., and Suelter, C. H. (1967) *J. Biol. Chem.* 242, 2502–2506) through the phosphocellulose step. Inhibition of AMPDA activity is determined at 37° C. in a 0.1 ml assay mixture containing inhibitor, ~0.005U AMPDA, 0.1% bovine serum albumin, 10 mM ATP, 250 mM KCl, and 50 mM MOPS at pH 6.5. The concentration of the substrate AMP is varied from 0.125–10.0 mM. Catalysis is initiated by the addition of enzyme to the otherwise complete reaction mixture, and terminated after 5 minutes by injection into an HPLC system. Activities are determined from the amount of IMP formed during 5 minutes. IMP is separated from AMP by HPLC using a Beckman Ultrasil-SAX anion exchange column (4.6 mm×25 cm) with an isocratic buffer system (12.5 mM potassium phosphate, 30 mM KCl, pH 3.5) and detected spectrophotometrically by absorbance at 254 nm.

Phosphofructokinase: Enzyme (rabbit liver) is purchased from Sigma. Activity is measured at 30° C. in reactions in which the formation of fructose-1,6-bisphosphate is coupled to the oxidation of NADH via the action of aldolase, triosephosphate isomerase, and α-glycerophosphate dehydrogenase. Reaction mixtures (200 $\mu$l) are made up in 96-well microtitre plates and were read at 340 nm in a Molecular Devices Microplate Reader. The mixtures consist of 200 mM Tris-HCl pH 7.0, 2 mM DTT, 2 mM MgCl$_2$, 0.2 mM NADH, 0.2 MM ATP, 0.5 mM Fructose 6-phosphate, 1 unit aldolase/ml, 3 units/ml triosephosphate isomerase, and 4 units/ml α-glycerophosphate dehydrogenase. Test compound concentrations range from 1 to 500 $\mu$M. Reactions are started by the addition of 0.0025 units of phosphofructokinase and are monitored for 15 minutes.

Glycogen Phosphorylase: Enzyme (rabbit muscle) is purchased from Sigma. Activity is measured at 37° C. in reactions in which the formation of glucose 1-phosphate is coupled to the reduction of NADP via phosphoglucomutase and glucose 6-phosphate dehydrogenase. Assays are performed on 96-well microtitre plates and are read at 340 nm on a Molecular Devices Microplate Reader. Reaction mixtures consist of 20 mM imidazole, pH 7.4, 20 mM MgCl$_2$, 150 mM potassium acetate, 5 mM potassium phosphate, 1 mM DTT, 1 mg/ml BSA, 0.1 mM NADP, 1 unit/ml phosphoglucomutase, 1 unit/ml glucose 6-phosphate dehydrogenase, 0.5% glycogen. Test compound concentrations range from 1 to 500 $\mu$M. Reactions are started by the addition of 17 $\mu$g enzyme and are monitored for 20 minutes.

Adenylate Kinase: Enzyme (rabbit muscle) is purchase from Sigma. Activity is measured at 37° C. in reaction mixtures (100 $\mu$l) containing 100 mM Hepes, pH 7.4, 45 mM MgCl$_2$, 1 mM EGTA, 100 mM KCl, 2 mg/ml BSA, 1 mM AMP and 2 mM ATP. Reactions are started by addition of 4.4 ng enzyme and terminated after 5 minutes by addition of 17 $\mu$l perchloric acid. Precipitated protein is removed by centrifugation and the supernatant neutralized by addition of 33 $\mu$l 3 M KOH/3 M KHCO$_3$. The neutralized solution is clarified by centrifugation and filtration and analyzed for ADP content (enzyme activity) by HPLC using a YMC ODS AQ column (25×4.6 cm). A gradient is run from 0.1 M $KH_2PO_4$, pH 6, 8 mM tetrabutyl ammonium hydrogen sulfate to 75% acetonitrile. Absorbance is monitored at 254 nM.

Example D

Inhibition of Gluconeogenesis in Rat Hepatocytes

Hepatocytes are prepared from overnight fasted Sprague-Dawley rats (250–300 g) according to the procedure of Berry and Friend (Berry, M. N., Friend, D. S., 1969, J. Cell. Biol. 43, 506–520) as modified by Groen (Groen, A. K., Sips, H. J., Vervoom, R. C., Tager, J. M., 1982, Eur. J. Biochem. 122, 87–93). Hepatocytes (75 mg wet weight/ml) are incubated in 1 ml Krebs-bicarbonate buffer containing 10 mM Lactate, 1 mM pyruvate, 1 mg/ml BSA, and test compound concentrations from 1 to 500 μM. Incubations are carried out in a 95% oxygen, 5% carbon dioxide atmosphere in closed, 50-ml Falcon tubes submerged in a rapidly shaking water bath (37° C.). After 1 hour, an aliquot (0.25 ml) is removed, transferred to an Eppendorf tube and centrifuged. 50 μl of supernatant is then assayed for glucose content using a Sigma Glucose Oxidase kit as per the manufacturer's instructions.

Example E

Glucose Production Inhibition and Fructose-1,6-bisphosphate Accumulation in Rat Hepatocytes Isolated rat hepatocytes are prepared as described in Example D and incubated under the identical conditions described. Reactions are terminated by removing an aliquot (250 μl) of cell suspension and spinning it through a layer of oil (0.8 ml silicone/mineral oil, 4/1) into a 10% perchloric acid layer (100 μl). After removal of the oil layer, the acidic cell extract layer is neutralized by addition of ⅓rd volume of 3 M KOH/3 M $KHCO_3$. After thorough mixing and centrifugation, the supernatant is analyzed for glucose content as described in Example D, and also for fructose-1,6-bisphosphate. Fructose-1,6-bisphosphate is assayed spectrophotometrically by coupling its enzymatic conversion to glycerol 3-phosphate to the oxidation of NADH, which is monitored at 340 nm. Reaction mixtures (1 ml) consist of 200 mM Tris-HCl, pH 7.4, 0.3 mM NADH, 2 units/ml glycerol 3-phosphate dehydrogenase, 2 units/ml triosephosphate isomerase, and 50–100 μl cell extract. After a 30 minute preincubation at 37° C., 1 unit/ml of aldolase is added and the change in absorbance measured until a stable value is obtained. 2 moles of NADH are oxidized in this reaction per mole of fructose-1,6-bisphosphate present in the cell extract.

A dose-dependent inhibition of glucose production accompanied by a dose-dependent accumulation of fructose-1,6 bisphosphate (the substrate of FBPase) is an indication that the target enzyme in the gluconeogenic pathway, FBPase, is inhibited.

Example F

Blood Glucose Lowering Following Intravenous Administration to Fasted Rats

Sprague Dawley rats (250–300 g) are fasted for 18 hours and then dosed intravenously either with saline or up to about 60 mg/kg of an FBPase inhibitor. Inhibitors are dissolved in water and the solution adjusted to neutrality with NaOH. Blood samples are obtained from the tail vein of conscious animals just prior to injection and after 1 hour. Blood glucose is measured using a HemoCue Inc. glucose analyzer according to the instructions of the manufacturer.

Example G

Analysis of Drug Levels and Liver Accumulation in Rats

Sprague-Dawley rats (250–300 g) are fasted for 18 hours and then dosed intravenously either with saline up to about 60 mgs/kg of a compound of the invention. The compound is dissolved in water and the solution adjusted to neutrality with NaOH. One hour post injection rats are anesthetized with halothane and a liver biopsy (approx. 1 g) is taken as well as a blood sample (2 ml) from the posterior vena cava. A heparin flushed syringe and needle are used for blood collection. The liver sample is immediately homogenized in ice-cold 10% perchloric acid (3 ml), centrifuged, and the supernatant neutralized with ⅓rd volume of 3 M KOH/3 M $KHCO_3$. Following centrifugation and filtration, 50 μl of the neutralized extract is analyzed for compound content by HPLC. A YMC ODS AQ column (250×4.6 cm) is used and eluted with a gradient from 10 mM sodium phosphate pH 5.5 to 75% acetonitrile. Absorbance is monitored at 310–325 nm. Plasma is prepared from the blood sample by centrifugation and extracted by addition of methanol to 60% (v/v). The methanolic extract is clarified by centrifugation and filtration and then analyzed by HPLC as described above.

Example H

Glucose Lowering Following Oral Administration to the Fasted Rat

Compounds are administered by oral gavage to 18-hour fasted, Sprague Dawley rats (250–300g). Phosphonic acids are prepared in deionized water, and the solution adjusted to neutrality with sodium hydroxide. Prodrugs are dissolved in polyethylene glycol (mw 400). Blood glucose is measured immediately prior to dosing and at 1 hour intervals thereafter by means of a HemoCue glucose analyzer (HemoCue Inc., Mission Viejo, Calif.).

Example I

Estimation of the Oral Bioavailability of Phosphonic Acids and Their Prodrugs

Phosphonic acids are dissolved in water, and the solution adjusted to neutrality with sodium hydroxide. Prodrugs are dissolved in 10% ethanol/90% polyethlene glycol (mw 400). Compound is administered by oral gavage to 18-hour fasted Sprague-Dawley rats (220–250 g) at doses ranging from 10–60 mg/kg. The rats are subsequently placed in metabolic cages and urine is collected for 24 hours. The quantity of phosphonic acid excreted into urine is determined by HPLC analysis as described in Example G. In a separate study, urinary recovery is determined following intravenous (tail vein) administration of compound (in the case of the prodrugs, the appropriate parent phosphonic acid is administered I.V.). The percentage oral bioavailability is estimated by comparison of the recovery of compound in urine 24 hours following oral administration, to that recovered in urine 24 hours after intravenous administration.

Example J

Blood Glucose Lowering in Zucker Diabetic Fatty Rats, Oral

Zucker Diabetic Fatty rats are purchased from Genetics Models Inc. (Indianapolis, Ind.) at 8 weeks of age and fed the recommended Purina 5008 diet. At the age of 12 weeks, 16 animals with fed blood glucose levels between 500 and 700 mg/dl are selected and divided into two groups (n=8) with statistically equivalent average blood glucose levels. A compound of the invention is administered at a dose of up to about 300 mg/kg by oral gavage to one group of animals at 1 p.m. The drug solution for this treatment is prepared in deionized water and adjusted to neutrality by dropwise addition of 5 N NaOH. A second group of rats (n=8) is dosed orally with saline, in parallel. Blood glucose is measured in each rat just prior to drug or saline administration and 6 hours post administration. A HemoCue blood glucose analyzer (HemoCue Inc., Mission Viejo, Calif.) is used for these measurements according to the manufacturer's instructions.

Example K

Blood Glucose Lowering in Zucker Diabetic Fatty Rats, Intravenous 12-week old Zucker Diabetic Fatty rats (Genetics Models Inc., Indianapolis, Ind.) maintained on Purina 5008 diet are instrumented with tail artery and tail vein catheters at 8 am on the day of the study. Food is removed for the remainder of the day. Starting at 12 p.m., animals are infused for 6 hours via the tail vein catheter either with saline or compound of the invention at up to about 60 mg/kg/h. Blood samples are obtained from the tail artery catheter at the start of the infusions, and at hourly intervals thereafter. Glucose is measured in the samples by means of a HemoCue analyzer (HemoCue Inc., Mission Viejo, Calif.) according to the manufacturer's instructions.

Example L

Inhibition of Gluconeogenesis by FBPase Inhibitor in Zucker Diabetic Fatty Rats

Following a 6-hour infusion of a compound of the invention at up to about 60 mg/kg/h or saline to Zucker Diabetic Fatty rats (n=3/group) as described in Example K, a bolus of $^{14}$C-bicarbonate (40 $\mu$Ci/100 g body weight) is administered via the tail vein catheter. 20 minutes later, a blood sample (0.6 mL) is taken via the tail artery. Blood (0.5 ml) is diluted into 6 mL deionized water and protein precipitated by addition of 1 mL zinc sulfate (0.3 N) and 1 mL barium hydroxide (0.3 N). The mixture is centrifuged (20 minutes, 1000× g) and 5 mL of the resulting supernatant is then combined with 1 g of a mixed bed ion exchange resin (1 part AG 50W-X8, 100–200 mesh, hydrogen form, and 2 parts AG 1-X8, 100–200 mesh, acetate form) to separate $^{14}$C-bicabonate from $^{14}$C-glucose. The slurry is shaken at room temperature for four hours and then allowed to settle. An aliquot of the supernatant (0.5 mL) is then counted in 5 mL scintillation cocktail. The percentage inhibition of gluconeogenesis in drug-treated rats is calculated by dividing the average cpm of C-glucose in samples from drug-treated animals by those from saline-injected animals.

Inhibition $^{14}$C-Glucose production provides evidence that the glucose lowering activity in the Zucker Diabetic Fatty rat (Example K) is due to the inhibition of gluconeogenesis.

Example M

Blood Glucose Lowering in the Streptozotocin-Treated Rat

Diabetes is induced in male Sprague-Dawley rats (250–300 g) by intraperitoneal injection of 55 mg/kg streptozotocin (Sigma Chemical Co.). Six days later, blood glucose is measured as described in Example F. Animals are selected with fed blood glucose values (8 am) between 350 and 600 mg/dl, and divided into two groups. One group is dosed orally with compound (up to about 300 mg/kg) and the second with an equivalent volume of saline. Food is removed from the animals. Blood glucose is measured again after 2 and 4 hours of drug/saline administration.

Example N

Oral Absorption Determinations of Prodrugs in the Rat

Prodrugs of the invention are administered to normal, fed rats at 30 mg/kg both by intraperitoneal injection and by oral gavage (n=3 rats/compound/route of administration). Rats are subsequently placed in metabolic cages and urine collected for 24 hours. Parent compound, is quantitated in urine by reverse phase HPLC as described in Example G. By comparison of the amount of parent compound excreted in urine following oral administration to that following intraperitoneal administration, the % oral absorption is calculated for each prodrug.

Example O

Chronic Oral Efficacy in the ZDF Rat

To determine the chronic glucose lowering effects of a prodrug of the invention, ZDF are administered the drug orally for 3 weeks.

Methods: ZDF rats (10 weeks of age) are maintained either on powdered Purina 5008 rat chow (n=10) or the same powdered chow supplemented with 1% of the drug (n=8). Blood glucose measurements are made as described in Example F at baseline and at weekly intervals thereafter for a total of 3 weeks. Statistical analysis is performed using the Student's t test.

Example P

Identification of the P450 Isozyme Involved in the Activation

Prodrugs are evaluated for human microsome-catalyzed conversion to parent compound in the absence and presence of specific inhibitors of three major P450 isozymes: ketoconazole (CYP3A4), furafylline (CYP1A2), and sulfaphenazole (CYP2C9).

Methods: Reaction (0.5 ml @ 37° C.) consist of 0.2 M $KH_2PO_4$, 13 mM glucose-6-phosphate, 2.2 mM NADP$^+$, 1 unit of glucose-6-phosphate dehydrogenase, 0–2.5 mg/ml human microsomal protein (In Vitro Technologies, In.), 250$\mu$ prodrug, and 0–100 $\mu$M P450 isozyme inhibitor. Reactions are stopped by addition of methanol to a concentration of 60%, filtered (0.2 $\mu$M filter), and lyophilized. Samples are resuspended in HPLC buffer (10 mM phosphate pH 5.5, 2.5 mM octyl-triethylammonium), loaded onto a YMC C8 HPLC column (250×4.6 mm), and eluted with a methanol gradient to 80%. Formuation of parent drug is confirmed by co-elution with an authentic parent drug standard.

Results: Prodrug is converted readily to parent drug in human liver microsomes. Ketoconazole will inhibit the formation of parent drugs in a dose-dependent fashion. The other inhibitor, fusafylline and sulfaphenazole, will show no significant inhibition. The results indicate that CYP3A4 is the primary P450 isoform responsible for activation of prodrugs in human liver.

While in accordance with the patent statures, description of the various embodiments and processing conditions have been provided, the scope of the invention is not to be limited thereto or thereby. Modifications and alterations of the present invention will be apparent to those skilled in the art without departing from the scope and spirit of the present invention. Therefore, it will be appreciated that the scope of this invention is to be defined by the appended claims, rather than by the specific examples which have been presented by way of example.

We claim:

1. A compound of formula (I):

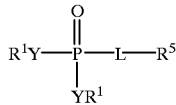

(I)

wherein $R^5$ is:

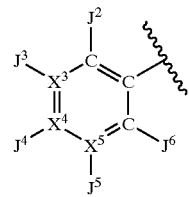

I (b)

wherein:
$X^3$, $X^4$, and $X^5$ are C;
$J^2$, $J^3$, $J^4$, $J^5$, and $J^6$ are independently selected from the group consisting of —H, —$NR^4{}_2$, —$CONR^4{}_2$, —$CO_2R^3$, halo, —$S(O)_2NR^4{}_2$, —$S(O)R^3$, —$SO_2R^3$, alkyl, alkenyl, alkynyl, alkylenearyl, perhaloalkyl, haloalkyl, aryl, heteroaryl, alkylene-OH, —$C(O)R^{11}$, —$OR^{11}$, -alkylene-$NR^4{}_2$, -alkylene-CN, —CN, —$C(S)NR^4{}_2$, —$OR^2$, —$SR^2$, —$N_3$, —$NO_2$, —$NHC(S)NR^4{}_2$, and —$NR^{18}COR^2$;
L is selected from the group consisting of:
 i) a linking group having 2–4 atoms measured by the fewest number of atoms connecting the carbon of the aromatic ring and the phosphorus atom and is selected from the group consisting of -furanyl-, -thienyl-, -pyridyl-, -oxazolyl-, -imidazolyl-, -pyrimidinyl-, -pyrazinyl-, and -alkynyl-, all of which may be optionally substituted; and
 ii) a linking group having 3–4 atoms measured by the fewest number of atoms connecting the carbon of the aromatic ring and the phosphorus atom and is optionally substituted -alkyeneoxy;
Y is independently selected from the group consisting of —O—, and —$NR^6$—;
when Y is —O—, then $R^1$ attached to —O— is independently selected from the group consisting of —H, alkyl, optionally substituted aryl, optionally substituted heterocyclic alkyl where the cyclic moiety contains a carbonate or thiocarbonate, optionally substituted arylalkylene-, —$C(R^2)_2OC(O)NR^2{}_2$, —$NR^2$—$C(O)$—$R^3$, —$C(R^2)_2$—$OC(O)R^3$, —$C(R^2)_2$—O—$C(O)OR^3$, —$C(R^2)_2OC(O)SR^3$, -alkylene-S—$C(O)R^3$, -alkylene-S—S-alkylenehydroxy, and -alkylene-S—S—S-alkylenehydroxy,
when one Y is —$NR^6$—, and $R^1$ attached to it is —$(CR^{12}R^{13})_n$—$C(O)$—$R^{14}$, then the other $YR^1$ is selected from the group consisting of —$NR^{15}R^{16}$, —$OR^7$, and $NR^6$—$(CR^{12}R^{13})_n$—$C(O)$—$R^{14}$;

or when either Y is independently selected from —O— and —$NR^6$—, then together $R^1$ and $R^1$ are -alkylene-S—S-alkylene- to form a cyclic group, or together $R^1$ and $R^1$ are

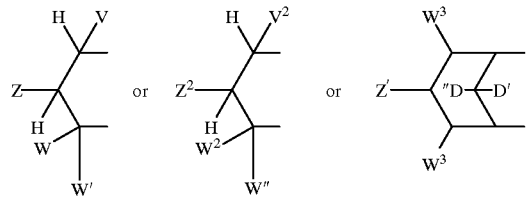

wherein
a) V is selected from the group of aryl, substituted aryl, heteroaryl, substituted heteroaryl, 1-alkynyl and 1-alkenyl;
 Z is selected from the group of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$OR^2$, —$SR^2$, —$CHR^2N_3$, —$CH_2$aryl, —CH(aryl)OH, —CH(CH=$CR^2{}_2$)OH, —CH(C≡$CR^2$)OH, —$R^2$, —$NR^2{}_2$, —$OCOR^3$, —$OCO_2R^3$, —$SCOR^3$, —$SCO_2R^3$, —$NHCOR^2$, —$NHCO_2R^3$, —$CH_2$NHaryl, —$(CH_2)_p$—$OR^{19}$, and —$(CH_2)_p$—$SR^{19}$; or
 together V and Z are connected via an additional 3–5 atoms to form a cyclic group, optionally containing 1 heteroatom, said cyclic group is fused to an aryl group at the beta and gamma position to the Y adjacent to V; or
 together Z and W are connected via an additional 3–5 atoms to form a cyclic group, optionally containing one heteroatom, and V must be aryl, substituted aryl, heteroaryl, or substituted heteroaryl; or
 W and W' are independently selected from the group of —H, alkyl, aralkyl, alicyclic, aryl, substituted aryl, heteroaryl, substituted heteroaryl, 1-alkenyl and 1-alkynyl and —$R^9$; or
 together W and W' are connected via an additional 2–5 atoms to form a cyclic group, optionally containing 0–2 heteroatoms, and V must be aryl, substituted aryl, heteroaryl, or substituted heteroaryl;
b) $V^2$, $W^2$ and W'" are independently selected from the group of —H, alkyl, aralkyl, alicyclic, aryl, substituted aryl, heteroaryl, substituted heteroaryl, 1-alkenyl, and 1-alkynyl;
 $Z^2$ is selected from the group of —$CHR^2OH$, —$CHR^2OC(O)R^3$, —$CHR^2OC(S)R^3$, —$CHR^2OCO_2R^3$, —$CHR^2OC(O)SR^3$, —$CHR^2OC(S)OR^3$, —CH(aryl)OH, —CH(CH=$CR^2{}_2$)OH, —CH(C≡$CR^2$)OH, —$SR^2$, —$CH_2$NHaryl, —$CH_2$aryl; or
 together $V^2$ and $Z^2$ are connected via an additional 3–5 atoms to form a cyclic group containing 5–7 ring atoms, optionally containing 1 heteroatom, and substituted with hydroxy, acyloxy, alkyleneoxycarbonyloxy, or aryloxycarbonyloxy attached to a carbon atom that is three atoms from a Y attached to phosphorus;
c) Z' is selected from the group of —OH, —$OC(O)R^3$, —$OCO_2R^3$, and —$OC(O)SR^3$;
 D' is —H;
 D" is selected from the group of —H, alkyl, —$OR^2$, —OH, and —$OC(O)R^3$;
 each $W^3$ is independently selected from the group consisting of —H, alkyl, aralkyl, alicyclic, aryl, substituted aryl, heteroaryl, substituted heteroaryl, 1-alkenyl, and 1-alkynyl;

p is an integer 2 or 3;
with the provisos that:
a) V, Z, W, W' are not all —H and V², Z², W², W" are not all —H; and
R² is selected from the group consisting of R³ and —H;
R³ is selected from the group consisting of alkyl, aryl, alicyclic, and aralkyl;
each R⁴ is independently selected from the group consisting of —H, alkylene, -alkylenearyl and aryl, or together R⁴ and R⁴ are connected via 2–6 atoms, optionally including one heteroatom selected from the group consisting of O, N, and S;
R⁶ is selected from the group consisting of —H, lower alkyl, acyloxyalkyl, aryl, aralkyl, alkyloxycarbonyloxyalkyl, and lower acyl, or together with R¹² is connected via 1–4 carbon atoms to form a cyclic group;
R⁷ is lower R³;
each R⁹ is independently selected from the group consisting of —H, alkyl, aralkyl, and alicyclic, or together R⁹ and R⁹ form a cyclic alkyl group;
R¹¹ is selected from the group consisting of alkyl, aryl, —NR²₂, and —OR²; and
each R¹² and R¹³ is independently selected from the group consisting of H, lower alkyl, lower aryl, lower aralkyl, all optionally substituted, or R¹² and R¹³ together are connected via a chain of 2–6 atoms, optionally including 1 heteroatom selected from the group consisting of O, N, and S, to form a cyclic group;
each R¹⁴ is independently selected from the group consisting of —OR¹⁷, —N(R¹⁷)₂, —NHR¹⁷, —SR¹⁷, and —NR²OR²⁰;
R¹⁵ is selected from the group consisting of —H, lower aralkyl, lower aryl, lower aralkyl, or together with R¹⁶ is connected via 2–6 atoms, optionally including 1 heteroatom selected from the group consisting of O, N, and S;
R¹⁶ is selected from the group consisting of —(CR¹²R¹³)ₙ—C(O)—R¹⁴, —H, lower alkyl, lower aryl, lower aralkyl, or together with R¹⁵ is connected via 2–6 atoms, optionally including 1 heteroatom selected from the group consisting of O, N, and S;
each R¹⁷ is independently selected from the group consisting of lower alkyl, lower aryl, and lower aralkyl, or together R¹⁷ and R¹⁷ on N is connected via 2–6 atoms, optionally including 1 heteroatom selected from the group consisting of O, N, and S;
R¹⁸ is selected from the group consisting of —H and lower R³;
R¹⁹ is selected from the group consisting of —H, and lower acyl;
R²⁰ is selected from the group consisting of —H, lower R³, and —C(O)-(lower R³);
n is an integer from 1 to 3;
with the provisos that:
1) when L is substituted furanyl, then at least one of J², J³, J⁴, and J⁵ is not —H or null;
2) when L is not substituted furanyl, then at least two of J², J³, J⁴, J⁵, and J⁶ on formula I(b) are not —H or null;
3) if both Y groups are —NR⁶—, and R¹ and R¹ are not connected to form a cyclic phosphoramidate, then at least one R¹ is —(CR¹²R¹³)ₙ—C(O)—R¹⁴;
4) when R⁵ is substituted phenyl, then J³, J⁴, and J⁵ is not purinyl, purinylalkylene, deaza-purinyl, or deazapurinylalkylene;

5) R¹ can be selected from the lower alkyl only when the other YR¹ is —NR⁶—C(R¹²R¹³)ₙ—C(O)—R¹⁴;
6) when R⁵ is substituted phenyl and L is 1,2-ethynyl, then J³ or J⁵ is not a heterocyclic group;
and pharmaceutically acceptable salts thereof.

2. The compounds of claim 1 wherein L is selected from the group consisting of:
i) 2,5-furanyl, 2,5-thienyl, 2,6-pyridyl, 2,5-oxazolyl, 5,2-oxazolyl, 2,4-oxazolyl, 4,2-oxazolyl, 2,4-imidazolyl, 2,6-pyrimidinyl, 2,6-pyrazinyl; and
ii) 1,2-ethynyl.

3. The compounds of claim 2 wherein L is selected from the group consisting of:
i) 2,5-furanyl, 2,5-thienyl, 2,6-pyridyl, 2,5-oxazolyl, 5,2-oxazolyl, 2,4-oxazolyl, 4,2-oxazolyl, 2,4-imidazolyl, 2,6-pyrimidinyl, 2,6-pyrazinyl; and
ii) 1,2-ethynyl.

4. The compounds of claim 2 wherein L is selected from the group consisting of:
i) 2,5-furanyl, 2,6-pyridyl, 2,5-oxazolyl, 2,4-imidazolyl; and
ii) 1,2-ethynyl.

5. The compounds of claim 4 wherein L is 2,5-furanyl.

6. The compounds of claim 1 wherein J², J³, J⁴, J⁵, and J⁶ are independently selected from the group consisting of —H, —NR⁴₂, —C(O)NR⁴₂, —CO₂R³, halo, —SO₂NR⁴₂, lower alkyl, lower alkenyl, lower alkynyl, lower perhaloalkyl, lower haloalkyl, lower aryl, lower alkylaryl, lower alkylene-OH, —OR¹¹, —CR²₂NR⁴₂, —CN, —C(S)NR⁴₂, —OR², —SR², —N₃, —NO₂, —NHC(S)NR⁴₂, —NR¹⁸C(O)R² and —CR²₂CN.

7. The compounds of claim 5 wherein J², J³, J⁴, J⁵, and J⁶ are independently selected from the group consisting of —H, —NO₂, lower alkyl, lower alkylaryl, lower alkoxy, lower perhaloalkyl, halo, —CH₂NHR⁴, —C(O)NR⁴₂, —S(O)₂NHR⁴, —OH, —NH₂, and —NHC(O)R².

8. The compounds of claim 1, where both Y groups are —O—.

9. The compounds of claim 1, where both Y groups are —NR⁶—.

10. The compounds of claim 1 where one Y is —NR⁶—, and one Y is —O—.

11. The compounds of claim 1 wherein each YR¹ is —OH.

12. The compounds of claim 1 wherein R¹ and R¹ together are

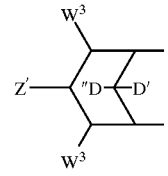

Z' is selected from the group of —OH, —OC(O)R³, —OCO₂R³, and —OC(O)SR³;
D' is —H;
D" is selected from the group of —H, alkyl, —OR², —OH, and —OC(O)R³; and
each W³ is independently selected from the group consisting of —H, alkyl, aralkyl, alicyclic, aryl, substituted aryl, heteroaryl, substituted heteroaryl, 1-alkenyl, and 1-alkynyl.

13. The compounds of claim 1 wherein R¹ and R¹ together are

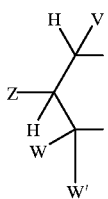

V is selected from the group of aryl, substituted aryl, heteroaryl, substituted heteroaryl, 1-alkynyl and 1-alkenyl;

Z is selected from the group of —CHR²OH, —CHR²OC(O)R³, —CHR²OC(S)R³, —CHR²OC(S)OR³, —CHR²OC(O)SR³, —CHR²OCO₂R³, —OR², —SR², —CHR²N₃, —CH₂aryl, —CH(aryl)OH, —CH(CH=CR²₂)OH, —CH(C≡CR²)OH, —R², —NR²₂, —OCOR³, —OCO₂R³, —SCOR³, —SCO₂R³, —NHCOR², —NHCO₂R³, —CH₂NHaryl, —(CH₂)ₚ—OR¹⁹, and —(CH₂)ₚ—SR¹⁹; or together V and Z are connected via an additional 3–5 atoms to form a cyclic group, optionally containing 1 heteroatom, said cyclic group is fused to an aryl group at the beta and gamma position to the Y adjacent to V; or together Z and W are connected via an additional 3–5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl and —R⁹; or together W and W' are connected via an additional 2–5 atoms to form a cyclic group, optionally containing 0–2 heteroatoms, and V must be aryl, substituted aryl, heteroaryl, or substituted heteroaryl.

14. The compounds of claim 1 wherein R¹ and R¹ together are

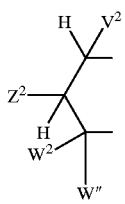

V², W² and W" are independently selected from the group of —H, alkyl, aralkyl, alicyclic, aryl, substituted aryl, heteroaryl, substituted heteroaryl, 1-alkenyl, and 1-alkynyl;

Z² is selected from the group of —CHR²OH, —CHR²OC(O)R³, —CHR²OC(S)R³, —CHR²OCO₂R³, —CHR²OC(O)SR³, —CHR²OC(S)OR³, —CH(aryl)OH, —CH(CH=CR²₂)OH, —CH(C≡CR²)OH, —SR², —CH₂NHaryl, —CH₂aryl; or together V² and Z² are connected via an additional 3–5 atoms to form a cyclic group containing 5–7 ring atoms, optionally containing 1 heteroatom, and substituted with hydroxy, acyloxy, alkyleneoxycarbonyloxy, or aryloxycarbonyloxy attached to a carbon atom that is three atoms from a Y attached to phosphorus.

15. The compounds of claim 1 wherein when both Y groups are —O—, then R¹ attached to —O— is optionally substituted aryl.

16. The compounds of claim 1 wherein when both Y groups are —O—, then R¹ is independently selected from the group consisting of optionally substituted aralkyl.

17. The compounds of claim 1 wherein both Y groups are —O—, and at least one R¹ is selected from the group consisting of —C(R²)₂—OC(O)R³, and —C(R²)₂—OC(O)OR³.

18. The compounds of claim 1 wherein at least one Y is —O—, and together R¹ and R¹ are

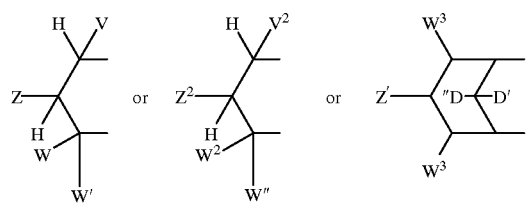

wherein a) V is selected from the group of aryl, substituted aryl, heteroaryl, substituted heteroaryl, 1-alkynyl and 1-alkenyl;

Z is selected from the group of —CHR²OH, —CHR²OC(O)R³, —CHR²OC(S)R³, —CHR²OC(S)OR³, —CHR²OC(O)SR³, —CHR²OCO₂R³, —OR², —SR², —CHR²N₃, —CH₂aryl, —CH(aryl)OH, —CH(CH=CR²₂)OH, —CH(C≡CR²)OH, —R², —NR²₂, —OCOR³, —OCO₂R³, —SCOR³, —SCO₂R³, —NHCOR², —NHCO₂R³, —CH₂NHaryl, —(CH₂)ₚ—OR¹⁹, and —(CH₂)ₚ—SR¹⁹; or together V and Z are connected via an additional 3–5 atoms to form a cyclic group, optionally containing 1 heteroatom, said cyclic group is fused to an aryl group at the beta and gamma position to the Y adjacent to V; or together Z and W are connected via an additional 3–5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl and —R⁹; or together W and W' are connected via an additional 2–5 atoms to form a cyclic group, optionally containing 0–2 heteroatoms, and V must be aryl, substituted aryl, heteroaryl, or substituted heteroaryl;

b) V², W² and W" are independently selected from the group of —H, alkyl, aralkyl, alicyclic, aryl, substituted aryl, heteroaryl, substituted heteroaryl, 1-alkenyl, and 1-alkynyl;

Z² is selected from the group of —CHR²OH, —CHR²OC(O)R³, —CHR²OC(S)R³, —CHR²OCO₂R³, —CHR²OC(O)SR³, —CHR²OC(S)OR³, —CH(aryl)OH, —CH(CH=CR²₂)OH, —CH(C≡CR²)OH, —SR², —CH₂NHaryl, —CH₂aryl; or together V² and Z² are connected via an additional 3–5 atoms to form a cyclic group containing 5–7 ring atoms, optionally containing 1 heteroatom, and substituted with hydroxy, acyloxy, alkyleneoxycarbonyloxy, or aryloxycarbonyloxy attached to a carbon atom that is three atoms from a Y attached to phosphorus;

c) Z' is selected from the group of —OH, —OC(O)R³, —OCO₂R³, and —OC(O)SR³;

D' is —H;

D" is selected from the group of —H, alkyl, —OR², —OH, and —OC(O)R³;

each W³ is independently selected from the group consisting of —H, alkyl, aralkyl, alicyclic, aryl, substituted aryl, heteroaryl, substituted heteroaryl, 1-alkenyl, and 1-alkynyl;

p is an integer 2 or 3;

with the provisos that:

a) V, Z, W, W' are not all —H and V², Z², W², W''' are not all —H; and b) both Y groups are not —NR⁶—;

R² is selected from the group consisting of R³ and —H;

R³ is selected from the group consisting of alkyl, aryl, alicyclic, and aralkyl;

R⁶ is selected from the group consisting of —H, and lower alkyl.

19. The compounds of claim 1 wherein one Y is —O—, and R¹ is optionally substituted aryl; and the other Y is —NR⁶—, where R¹ attached to said —NR⁶— is selected from the group consisting of —C(R⁴)₂C(O)OR³, and —C(R²)₂C(O)OR³.

20. The compounds of claim 1 wherein

J², J³, J⁴, J⁵, and J⁶ are independently selected from the group consisting of —H, —NR⁴₂, —CONR⁴₂, —CO₂R³, halo, —SO₂NR⁴₂, lower alkyl, lower alkenyl, lower alkylenearyl, lower alkynyl, lower perhaloalkyl, lower haloalkyl, lower aryl, lower alkylene-OH, —OR¹¹, —CR²₂NR⁴₂, —CN, —C(S)NR⁴₂, —OR², —SR², —N₃, —NO₂, —NHC(S)NR⁴₂, —NR¹⁸COR², CR²₂CN;

L is selected from the group consisting of i) 2,5-furanyl, 2,5-thienyl, 2,6-pyridyl, 2,5-oxazolyl, 5,2-oxazolyl, 2,4-oxazolyl, 4,2-oxazolyl, 2,4-imidazolyl, 2,6-pyrimidinyl, 2,6-pyrazinyl; and ii) 1,2-ethynyl;

when both Y groups are —O—, then R¹ is independently selected from the group consisting of optionally substituted aryl, optionally substituted benzyl, —C(R²)₂OC(O)R³, —C(R²)₂OC(O)OR³, and —H; or when one Y is —O—, then R¹ attached to —O— is optionally substituted aryl; and the other Y is —NR⁶—, then R¹ attached to —NR⁶— is selected from the group consisting of —C(R⁴)₂C(O)OR³, and —C(R²)₂C(O)OR³; or when Y is —O— or —NR⁶—, then together R¹ and R¹ are

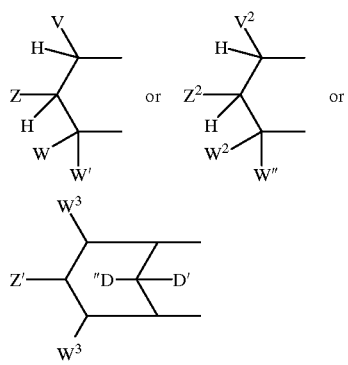

wherein a) V is selected from the group of aryl, substituted aryl, heteroaryl, substituted heteroaryl, 1-alkynyl and 1-alkenyl;

Z is selected from the group of —CHR²OH, —CHR²OC(O)R³, —CHR²OC(S)R³, —CHR OC(S)OR³, —CHR²OC(O)SR³, —CHR²OCO₂R³, —OR², —SR², —CHR²N₃, —CH₂aryl, —CH(aryl)OH, —CH(CH=CR²₂)OH, —CH(C≡CR²)OH, —R², —NR²₂, —OCOR³, —OCO₂R³, —SCOR³, —SCO₂R³, —NHCOR², —NHCO₂R³, —CH₂NHaryl, —(CH₂)ₚ—OR¹⁹, and —(CH₂)ₚ—SR¹⁹; or together V and Z are connected via an additional 3–5 atoms to form a cyclic group, optionally containing 1 heteroatom, said cyclic group is fused to an aryl group at the beta and gamma position to the Y adjacent to V; or together Z and W are connected via an additional 3–5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl and —R⁹; or together W and W' are connected via an additional 2–5 atoms to form a cyclic group, optionally containing 0–2 heteroatoms, and V must be aryl, substituted aryl, heteroaryl, or substituted heteroaryl;

b) V², W² and W''' are independently selected from the group of —H, alkyl, aralkyl, alicyclic, aryl, substituted aryl, heteroaryl, substituted heteroaryl, 1-alkenyl, and 1-alkynyl;

Z² is selected from the group of —CHR²OH, —CHR²OC(O)R³, —CHR²OC(S)R³, —CHR²OCO₂R³, —CHR²OC(O)SR³, —CHR²OC(S)OR³, —CH(aryl)OH, —CH(CH=CR²₂)OH, —CH(C≡CR²)OH, —SR², —CH₂NHaryl, —CH₂aryl; or together V² and Z² are connected via an additional 3–5 atoms to form a cyclic group containing 5–7 ring atoms, optionally containing 1 heteroatom, and substituted with hydroxy, acyloxy, alkyleneoxycarbonyloxy, or aryloxycarbonyloxy attached to a carbon atom that is three atoms from a Y attached to phosphorus;

c) Z' is selected from the group of —OH, —OC(O)R³, —OCO₂R³, and —OC(O)SR³;

D' is —H;

D'' is selected from the group of —H, alkyl, —OR², —OH, and —OC(O)R³;

each W³ is independently selected from the group consisting of —H, alkyl, aralkyl, alicyclic, aryl, substituted aryl, heteroaryl, substituted heteroaryl, 1-alkenyl, and 1-alkynyl;

p is an integer 2 or 3;

with the provisos that:

a) V, Z, W, W' are not all —H and V², Z², W², W''' are not all —H; and alicyclic; and b) both Y groups are not —NR⁶—;

R² is selected from the group consisting of R³ and —H;

R³ is selected from the group consisting of alkyl, aryl, alicyclic, and aralkyl;

R⁶ is selected from the group consisting of —H, and lower alkyl.

21. The compounds of claim 1 wherein R⁵ is substituted phenyl;

L is furan-2,5-diyl; J², J³, J⁴, J⁵, and J⁶ are independently selected from the group consisting of —OR³, —SO₂NHR⁴, —CN, —H, halo, —NR⁴₂, —(CH₂)₂aryl, —(CH₂)NHaryl, and —NO₂; at least one Y group is —O—.

22. The compounds of claim 1 wherein one Y is —NR⁶—, and R¹ attached to it is —(CR¹²R¹³)ₙ—C(O)—R¹⁴, then the other YR$^1$ is selected from the group consisting of —NR$^{15}$R$^{16}$, —OR$^7$, and NR$^6$—(CR$^{12}$R$^{13}$)$_n$—C(O)—R$^{14}$.

23. The compounds of claim 22 wherein the other YR$^1$ is —OR$^7$.

24. The compounds of claim 1 that are of the formula:

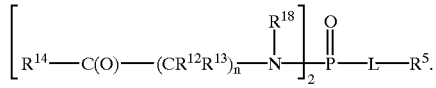

25. A compound of formula (I):

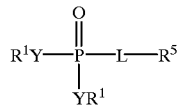

wherein R$^5$ is:

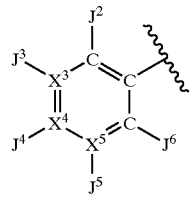

wherein:

X$^3$, X$^4$, and X$^5$ are C;

J$^2$, J$^3$, J$^4$, J$^5$, and J$^6$ are independently selected from the group consisting of —CONR$^4$$_2$, —CO$_2$R$^3$, —S(O)$_2$NR$^4$$_2$, —S(O)R$^3$, alkyl, alkenyl, alkynyl, alkylenearyl, perhaloalkyl, haloalkyl, aryl, heteroaryl, alkylene-OH, —C(O)R$^{11}$, —OR$^{11}$, -alkylene-NR$^4$$_2$, -alkylene-CN, —CN, —C(S)NR$^4$$_2$, —OR$^2$, —SR$^2$, —N$_3$, —NHC(S)NR$^4$$_2$, and —NR$^{18}$COR$^2$;

L is selected from the group consisting of:
i) a linking group having 2–4 atoms measured by the fewest number of atoms connecting the carbon of the aromatic ring and the phosphorus atom and is selected from the group consisting of -furanyl-, -thienyl-, -pyridyl-, -oxazolyl-, -imidazolyl-, -phenyl-, -pyrimidinyl-, -pyrazinyl-, and -alkynyl-, all of which may be optionally substituted; and
ii) a linking group having 3–4 atoms measured by the fewest number of atoms connecting the carbon of the aromatic ring and the phosphorus atom and is selected from the group consisting of -alkyleneoxycarbonyl-, -alkyleneoxy-, and -alkyleneoxyalkylene-, all of which may be optionally substituted;

Y is independently selected from the group consisting of —O—, and —NR$^6$—;

when Y is —O—, then R$^1$ attached to —O— is independently selected from the group consisting of —H, alkyl, optionally substituted aryl, optionally substituted alicyclic where the cyclic moiety contains a carbonate or thiocarbonate, optionally substituted arylalkylene-, —C(R$^2$)$_2$OC(O)NR$^2$$_2$, —NR$^2$—C(O)—R$^3$, —C(R$^2$)$_2$—OC(O)R$^3$, —C(R$^2$)$_2$—O—C(O)OR$^3$, —C(R$^2$)$_2$OC(O)SR$^3$, -alkylene-S—C(O)R$^3$, -alkylene-S—S-alkylenehydroxy, and -alkylene-S—S-alkylenehydroxy, when one Y is —NR$^6$—, and R$^1$ attached to it is —(CR$^{12}$R$^{13}$)$_n$—C(O)—R$^{14}$, then the other YR$^1$ is selected from the group consisting of —NR$^{15}$R$^{16}$, —OR$^7$, and NR$^6$—(CR$^{12}$R$^{13}$)$_n$—C(O)—R$^{14}$;

or when either Y is independently selected from —O— and —NR$^6$—, then together R$^1$ and R$^1$ are -alkylene-S—S-alkylene- to form a cyclic group, or together R$^1$ and R$^1$ are

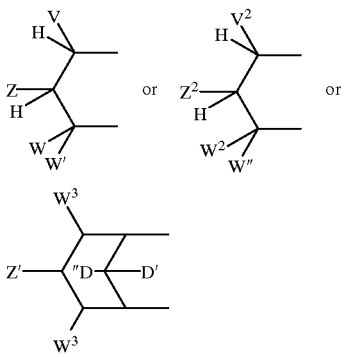

wherein
a) V is selected from the group of aryl, substituted aryl, heteroaryl, substituted heteroaryl, 1-alkynyl and 1-alkenyl;

Z is selected from the group of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2$$_2$)OH, —CH(C≡CR$^2$)OH, —R$^2$, —NR$^2$$_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^{19}$, and —(CH$_2$)$_p$—SR$^{19}$; or together V and Z are connected via an additional 3–5 atoms to form a cyclic group, optionally containing 1 heteroatom, said cyclic group is fused to an aryl group at the beta and gamma position to the Y adjacent to V; or together Z and W are connected via an additional 3–5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl and —R$^9$; or together W and W' are connected via an additional 2–5 atoms to form a cyclic group, optionally containing 0–2 heteroatoms, and V must be aryl, substituted aryl, heteroaryl, or substituted heteroaryl;

b) V$^2$, W$^2$ and W'' are independently selected from the group of —H, alkyl, aralkyl, alicyclic, aryl, substituted aryl, heteroaryl, substituted heteroaryl, 1-alkenyl, and 1-alkynyl;

Z$^2$ is selected from the group of —CHR$^2$OH, —CHR$^2$OC(O)R$^3$, —CHR$^2$OC(S)R$^3$, —CHR$^2$OCO$_2$R$^3$, —CHR$^2$OC(O)SR$^3$, —CHR$^2$OC(S)OR$^3$, —CH(aryl)OH, —CH(CH=CR$^2$$_2$)OH, —CH(C≡CR$^2$)OH, —SR$^2$, —CH$_2$NHaryl, —CH$_2$aryl; or together V$^2$ and Z$^2$ are connected via an additional 3–5 atoms to form a cyclic group containing 5–7 ring atoms, optionally containing 1 heteroatom, and substituted with hydroxy, acyloxy, alkyleneoxycarbonyloxy, or aryloxycarbonyloxy attached to a carbon atom that is three atoms from a Y attached to phosphorus;

c) Z' is selected from the group of —OH, —OC(O)R$^3$, —OCO$_2$R$^3$, and —OC(O)SR$^3$;

D' is —H;

D" is selected from the group of —H, alkyl, —OR$^2$, —OH, and —OC(O)R$^3$;

each W$^3$ is independently selected from the group consisting of —H, alkyl, aralkyl, alicyclic, aryl, substituted aryl, heteroaryl, substituted heteroaryl, 1-alkenyl, and 1-alkynyl;

p is an integer 2 or 3;

with the provisos that:

a) V, Z, W, W' are not all —H and V$^2$, Z$^2$, W$^2$, W" are not all —H; and

R$^2$ is selected from the group consisting of R$^3$ and —H;

R$^3$ is selected from the group consisting of alkyl, aryl, alicyclic, and aralkyl;

each R$^4$ is independently selected from the group consisting of —H, alkylene, -alkylenearyl and aryl, or together R$^4$ and R$^4$ are connected via 2–6 atoms, optionally including one heteroatom selected from the group consisting of O, N, and S;

R$^6$ is selected from the group consisting of —H, lower alky, acyloxyalkyl, aryl, aralkyl, alkyloxycarbonyloxyalkyl, and lower acyl, or together with R$^{12}$ is connected via 1–4 carbon atoms to form a cyclic group;

R$^7$ is lower R$^3$;

each R$^9$ is independently selected from the group consisting of —H, alkyl, aralkyl, and alicyclic, or together R$^9$ and R$^9$ form a cyclic alkyl group;

R$^{11}$ is selected from the group consisting of alkyl, aryl, —NR$^2_2$, and —OR$^2$; and each R$^{12}$ and R$^{13}$ is independently selected from the group consisting of H, lower alkyl, lower aryl, lower aralkyl, all optionally substituted, or R$^{12}$ and R$^{13}$ together are connected via a chain of 2–6 atoms, optionally including 1 heteroatom selected from the group consisting of O, N, and S, to form a cyclic group;

each R$^{14}$ is independently selected from the group consisting of —OR$^{17}$, —N(R$^{17}$)$_2$, —NHR$^{17}$, —SR$^{17}$, and —NR$^2$OR$^{20}$;

R$^{15}$ is selected from the group consisting of —H, lower aralkyl, lower aryl, lower aralkyl, or together with R$^{16}$ is connected via 2–6 atoms, optionally including 1 heteroatom selected from the group consisting of O, N, and S;

R$^{16}$ is selected from the group consisting of —(CR$^{12}$R$^{13}$)$_n$—C(O)—R$^{14}$, —H, lower alkyl, lower aryl, lower aralkyl, or together with R$^{15}$ is connected via 2–6 atoms, optionally including 1 heteroatom selected from the group consisting of O, N, and S;

each R$^{17}$ is independently selected from the group consisting of lower alkyl, lower aryl, and lower aralkyl, or together R$^{17}$ and R$^{17}$ on N is connected via 2–6 atoms, optionally including 1 heteroatom selected from the group consisting of O, N, and S;

R$^{18}$ is selected from the group consisting of —H and lower R$^3$;

R$^{19}$ is selected from the group consisting of —H, and lower acyl;

R$^{20}$ is selected from the group consisting of —H, lower R$^3$, and —C(O)-(lower R$^3$);

n is an integer from 1 to 3;

with the provisos that:

1) if both Y groups are —NR$^6$—, and R$^1$ and R$^1$ are not connected to form a cyclic phosphoramidate, then at least one R$^1$ is —(CR$^{12}$R$^{13}$)$_n$—C(O)—R$^{14}$;

2) when R$^5$ is substituted phenyl, then J$^3$, J$^4$, J$^5$ is not purinyl, purinylalkylene, deaza-purinyl, or deazapurinylalkylene;

3) R$^1$ can be selected from the lower alkyl only when the other YR$^1$ is —NR$^6$—C(R$^{12}$R$^{13}$)$_n$—C(O)—R$^{14}$;

when R$^5$ is substituted phenyl and L is 1,2-ethynyl, then J$^3$ or J$^5$ is not a heterocyclic group;

and pharmaceutically acceptable prodrugs and salts thereof.

26. The compounds of claim 25 with the further proviso that when L is -alkyleneoxyalkylene-, and R$^5$ substituted phenyl, then J$^3$, J$^4$, or J$^5$ is not alkenyl.

27. The compounds of claim 25 with the further proviso that when L is -alkyleneoxyalkylene-, then R$^5$ is substituted phenyl.

28. The compounds of claim 25 with the further proviso that when L is -alkyleneoxycarbonyl-, and X$^3$, X$^4$, and X$^5$ are all C, then neither J$^2$ nor J$^6$ is a group attached through a nitrogen atom.

29. The compounds of claim 25 wherein L is selected from the group consisting of:
   i) 2,5-furanyl, 2,5-thienyl, 2,6-pyridyl, 2,5-oxazolyl, 5,2-oxazolyl, 2,4-oxazolyl, 4,2-oxazolyl, 2,4-imidazolyl, 2,6-pyrimidinyl, 2,6-pyrazinyl, 1,3-phenyl;
   ii) 1,2-ethynyl; and
   iii) a linking group having 3 atoms measured by the fewest number of atoms connecting the carbon of the aromatic ring and the phosphorus atom and is selected from the group consisting of -alkyleneoxycarbonyl-, and -alkyleneoxyalkylene-.

30. The compounds of claim 29 wherein L is selected from the group consisting of:
   i) 2,5-furanyl, 2,5-thienyl, 2,6-pyridyl, 2,5-oxazolyl, 5,2-oxazolyl, 2,4-oxazolyl, 4,2-oxazolyl, 2,4-imidazolyl, 2,6-pyrimidinyl, 2,6-pyrazinyl, 1,3-phenyl; and
   ii) 1,2-ethynyl.

31. The compounds of claim 30 wherein L is selected from the group consisting of:
   i) 2,5-furanyl, 2,6-pyridyl, 2,5-oxazolyl, 2,4-imidazolyl. 113-phenyl;
   ii) 1,2-ethynyl; and
   iii) a linking group having 3 atoms measured by the fewest number of atoms connecting the carbon of the aromatic ring and the phosphorus atom and is selected from the group consisting of -methyleneoxycarbonyl-, and -methyleneoxymethylene-.

32. The compounds of claim 31 wherein L is selected from the group consisting of 2,5-furanyl, methyleneoxycarbonyl, and methyleneoxymethylene.

33. The compounds of claim 32 wherein L is 2,5-furanyl.

34. The compounds of claim 25 wherein J$^2$, J$^3$, J$^4$, J$^5$, and J$^6$ are independently selected from the group consisting of —C(O)NR$^4_2$, —CO$_2$R$^3$, —SO$_2$NR$^4_2$, lower alkyl, lower alkenyl, lower alkynyl, lower perhaloalkyl, lower haloalkyl, lower aryl, lower alkylaryl, lower alkylene-OH, —OR$^{11}$, —CR$^2_2$NR$^4_2$, —CN, —C(S)NR$^4_2$, —OR$^2$, —SR$^2$, —N$_3$, —NHC(S)NR$^{42}$, —NR$^{18}$C(O)R$^2$ and —CR$^2_2$CN.

35. The compounds of claim 32 wherein J$^2$, J$^3$, J$^4$, J$^5$, and J$^6$ are independently selected from the group consisting of lower alkyl, lower alkylaryl, lower alkoxy, lower perhaloalkyl, —CH$_2$NHR$^4$, —C(O)NR$^4_2$, —S(O)$_2$NHR$^4$, —OH, and —NHC(O)R$^2$.

36. The compounds of claim 25, where both Y groups are —O—.

37. The compounds of claim 25 where both Y groups are —NR$^6$—.

38. The compounds of claim 25 where one Y is —NR$^6$—, and one Y is —O—.

39. The compounds of claim 25 wherein each YR$^1$ is —OH.

40. The compounds of claim 25 wherein R$^1$ and R$^1$ together are

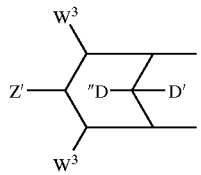

Z' is selected from the group of —OH, —OC(O)R$^3$, —OCO$_2$R$^3$, and —OC(O)SR$^3$;
D' is —H;
D" is selected from the group of —H, alkyl, —OR$^2$, —OH, and —OC(O)R$^3$; and
each W$^3$ is independently selected from the group consisting of —H, alkyl, aralkyl alicyclic, aryl, substituted aryl, heteroaryl, substituted heteroaryl, 1-alkenyl, and 1-alkynyl.

41. The compounds of claim 25 wherein R$^1$ and R$^1$ together are

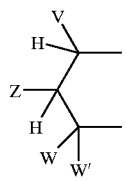

V is selected from the group of aryl, substituted aryl, heteroaryl, substituted heteroaryl, and 1-alkynyl 1-alkenyl;
Z is selected from the group of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2$$_2$)OH, —CH(C≡CR$^2$)OH, —R$^2$, —NR$^2$$_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^{19}$, and —(CH$_2$)$_p$—SR$^{19}$; or together V and Z are connected via an additional 3–5 atoms to form a cyclic group, optionally containing 1 heteroatom, said cyclic group is fused to an aryl group at the beta and gamma position to the Y adjacent to V; or together Z and W are connected via an additional 3–5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl and —R$^9$; or together W and W' are connected via an additional 2–5 atoms to form a cyclic group, optionally containing 0–2 heteroatoms, and V must be aryl, substituted aryl, heteroaryl, or substituted heteroaryl.

42. The compound of claim 25 wherein R$^1$ and R$^1$ together are

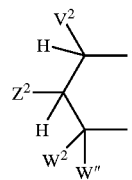

V$^2$, W$^2$ and W" are independently selected from the group of —H, alkyl, aralkyl, alicyclic, aryl, substituted aryl, heteroaryl, substituted heteroaryl, 1-alkenyl, and 1-alkynyl;

Z$^2$ is selected from the group of —CHR$^2$OH, —CHR$^2$OC(O)R$^3$, —CHR$^2$OC(S)R$^3$, —CHR$^2$OCO$_2$R$^3$, —CHR$^2$OC(O)SR$^3$, —CHR$^2$OC(S)OR$^3$, —CH(aryl)OH, —CH(C=CR$^2$$_2$)OH, —CH(C≡CR$^2$)OH, —SR$^2$, —CH$_2$NHaryl, —CH$_2$aryl; or together V$^2$ and Z$^2$ are connected via an additional 3–5 atoms to form a cyclic group containing 5–7 ring atoms, optionally containing 1 heteroatom, and substituted with hydroxy, acyloxy, alkyleneoxycarbonyloxy, or aryloxycarbonyloxy attached to a carbon atom that is three atoms from a Y attached to phosphorus.

43. The compounds of claim 25 wherein when both Y groups are —O—, then R$^1$ attached to —O— is optionally substituted aryl.

44. The compounds of claim 25 wherein when both Y groups are —O—, then R$^1$ is independently selected from the group consisting of optionally substituted aralkyl.

45. The compounds of claim 25 wherein both Y groups are —O—, and at least one R$^1$ is selected from the group consisting of —C(R$^2$)$_2$—OC(O)R$^3$, and —C(R$^2$)$_2$—OC(O)OR$^3$.

46. The compounds of claim 25 wherein at least one Y is —O—, and together R$^1$ and R$^1$ are

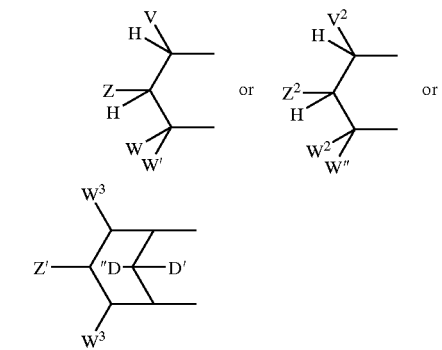

wherein
a) V is selected from the group of aryl, substituted aryl, heteroaryl, substituted heteroaryl, 1-alkynyl and 1-alkenyl;
Z is selected from the group of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2$$_2$)OH, —CH(C≡CR$^2$)OH, —R$^2$, —NR$^2$$_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^{19}$, and —(CH$_2$)$_p$—SR$^{19}$; or together V and Z are connected via an additional 3–5 atoms to form a cyclic group, optionally containing 1 heteroatom, said cyclic group is fused to an aryl group at the beta and gamma position to the Y adjacent to V; or together Z and W are connected via an additional 3–5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl and —$R^9$; or together W and W' are connected via an additional 2–5 atoms to form a cyclic group, optionally containing 0–2 heteroatoms, and V must be aryl, substituted aryl, heteroaryl, or substituted heteroaryl;

b) $V^2$, $W^2$ and W" are independently selected from the group of —H, alkyl, aralkyl, alicyclic, aryl, substituted aryl, heteroaryl, substituted heteroaryl, 1-alkenyl, and 1-alkynyl;

$Z^2$ is selected from the group of —$CHR^2OH$, —$CHR^2OC(O)R^3$, —$CHR^2OC(S)R^3$, —$CHR^2OCO_2R^3$, —$CHR^2OC(O)SR^3$, —$CHR^2OC(S)OR^3$, —CH(aryl)OH, —CH(CH=$CR^2_2$)OH, —CH(C≡$CR^2$)OH, —$SR^2$, —$CH_2$NHaryl, —$CH_2$aryl; or together $V^2$ and $Z^2$ are connected via an additional 3–5 atoms to form a cyclic group containing 5–7 ring atoms, optionally containing 1 heteroatom, and substituted with hydroxy, acyloxy, alkyleneoxycarbonyloxy, or aryloxycarbonyloxy attached to a carbon atom that is three atoms from a Y attached to phosphorus;

c) Z' is selected from the group of —OH, —OC(O)$R^3$, —$OCO_2R^3$, and —OC(O)$SR^3$;

D is —H;

D" is selected from the group of —H, alkyl, —$OR^2$, —OH, and —OC(O)$R^3$;

each $W^3$ is independently selected from the group consisting of —H, alkyl, aralkyl, alicyclic, aryl, substituted aryl, heteroaryl, substituted heteroaryl, 1-alkenyl, and 1-alkynyl;

p is an integer 2 or 3;

with the provisos that:

a) V, Z, W, W' are not all —H and $V^2$, $Z^2$, $W^2$, W" are not all —H; and b) both Y groups are not —$NR^6$—;

$R^2$ is selected from the group consisting of $R^3$ and —H;

$R^3$ is selected from the group consisting of alkyl, aryl, alicyclic, and aralkyl;

$R^6$ is selected from the group consisting of —H, and lower alkyl.

47. The compounds of claim 25 wherein one Y is —O—, and $R^1$ is optionally substituted aryl; and the other Y is —$NR^6$—, where $R^1$ attached to said —$NR^6$— is selected from the group consisting of —$C(R^4)_2C(O)OR^3$, and —$C(R^2)_2C(O)OR^3$.

48. The compounds of claim 25 wherein $J^2$, $J^3$, $J^4$, $J^5$, and $J^6$ are independently selected from the group consisting of —$CONR^4_2$, —$CO_2R^3$, —$SO_2NR^4_2$, lower alkyl, lower alkenyl, lower alkylenearyl, lower alkynyl, lower perhaloalkyl, lower haloalkyl, lower aryl, lower alkylene-OH, —$OR^{11}$, —$CR^2_2NR^4_2$, —CN, —C(S)$NR^4_2$, —$OR^2$, —$SR^2$, —$N_3$, —NHC(S)$NR^4$, —$NR^{18}COR^2$, —$CR^2_2$CN.

L is selected from the group consisting of i) 2,5-furanyl, 2,4-thienyl, 1,3-phenyl, 2,6-pyridyl, 2,5-oxazolyl, 5,2oxazolyl, 2,4-oxazolyl, 4,2-oxazolyl, 2,4-imidazolyl, 2,6-pyrimidinyl, 2,6-pyrazinyl;

ii) 1,2-ethynyl; and iii) a linking group having 3 atoms measured by the fewest number of atoms connecting the carbon of the aromatic ring and the phosphorus atom and is selected from the group consisting of alkyleneoxycarbonyl-, and -alkyleneoxyalkylene-;

when both Y groups are —O—, then $R^1$ is independently selected from the group consisting of optionally substituted aryl, optionally substituted benzyl, —$C(R^2)_2OC(O)R^3$, —$C(R^2)_2OC(O)OR^3$, and —H; or when one Y is —O—, then $R^1$ attached to —O— is optionally substituted aryl; and the other Y is —$NR^6$—, then $R^1$ attached to —$NR^6$— is selected from the group consisting of —$C(R^{42})_2C(O)OR^3$, and —$C(R^2)_2C(O)OR^3$; or when Y is —O— or —$NR^6$—, then together $R^1$ and $R^1$ are wherein a) V is selected from the group of aryl, substituted aryl, heteroaryl, substituted heteroaryl, 1-alkynyl and 1-alkenyl;

Z is selected from the group of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$OR^2$, —$SR^2$, —$CHR^2N_3$, —$CH_2$aryl, —CH(aryl)OH, —CH(CH=$CR^2_2$)OH, —CH(C≡$CR^2$)OH, —$R^2$, —$NR^2_2$, —$OCOR^3$, —$OCO_2R^3$, —$SCOR^3$, —$SCO_2R^3$, —$NHCOR^2$, —$NHCO_2R^3$, —$CH_2$NHaryl, —$(CH_2)_p$—$OR^{19}$, and —$(CH_2)_p$—$SR^{19}$; or together V and Z are connected via an additional 3–5 atoms to form a cyclic group, optionally containing 1 heteroatom, said cyclic group is fused to an aryl group at the beta and gamma position to the Y adjacent to V; or together Z and W are connected via an additional 3–5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl hand —$R^9$; or together W and W' are connected via an additional 2–5 atoms to form a cyclic group, optionally containing 0–2 heteroatoms, and V must be aryl, substituted aryl, heteroaryl, or substituted heteroaryl;

b) $V^2$, $W^2$ and W" are independently selected from the group of —H, alkyl, aralkyl alicyclic, aryl, substituted aryl, heteroaryl, substituted heteroaryl, 1-alkenyl, and 1-alkynyl;

$Z^2$ is selected from the group of —$CHR^2OH$, —$CHR^2OC(O)R^3$, —$CHR^2OC(S)R^3$, —$CHR^2OCO_2R^3$, —CHR²OC(O)SR³, —CHR²OC(S)OR³, —CH(aryl)OH, —CH(CH=CR²₂)OH, —CH(C=CR²)OH, —SR², —CH₂NHaryl, —CH₂aryl; or together V² and Z² are connected via an additional 3–5 atoms to form a cyclic group containing 5–7 ring atoms, optionally containing 1 heteroatom, and substituted with hydroxy, acyloxy, alkyleneoxycarbonyloxy, or aryloxycarbonyloxy attached to a carbon atom that is three atoms from a Y attached to phosphorus;

c) Z' is selected from the group of —OH, —OC(O)R³, —OCO₂R³, and —OC(O)SR³;

D' is —H;

D" is selected from the group of —H, alkyl, —OR², —OH, and —OC(O)R³;

each W³ is independently selected from the group consisting of —H, alkyl, aralkyl, alicyclic, aryl, substituted aryl, heteroaryl, substituted heteroaryl, 1-alkenyl, and 1-alkynyl;

p is an integer 2 or 3;

with the provisos that:

a) V, Z, W, W' are not all —H and V², Z², W², W" are not all —H; and alicyclic; and b) both Y groups are not —NR⁶—;

R² is selected from the group consisting of R³ and —H;

R³ is selected from the group consisting of alkyl, aryl, alicyclic, and aralkyl;

R⁶ is selected from the group consisting of —H, and lower alkyl.

49. The compounds of claim 25 wherein R⁵ is substituted phenyl;

L is furan-2,5-diyl; J², J³, J⁴, J⁵, and J⁶ are independently selected from the group consisting of —OR³, —SO₂NHR⁴, —CN, —(CH₂)₂aryl, and —(CH₂)NHaryl; at least one Y group is —O—.

50. The compounds of claim 25 wherein one Y is —NR⁶—, and R¹ attached to it is —(CR¹²R¹³)ₙ—C(O)—R¹⁴, then the other YR¹ is selected from the group consisting of —NR¹⁵R¹⁶, —OR⁷, and NR⁶—(CR¹²R¹³)ₙ—C(O)—R¹⁴.

51. The compounds of claim 50 wherein the other YR¹ is —OR⁷.

52. The compounds of claim 25 that are of the formula:

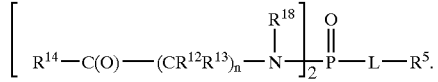

53. A compound of formula (I):

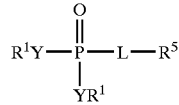

wherein R⁵ is:

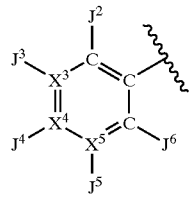

wherein:

X³, X⁴, and X⁵ are C;

J², J³, J⁴, J⁵, and J⁶ are independently selected from the group consisting of —H, —NR⁴₂, —CONR⁴₂, —CO₂R³, halo, —S(O)₂NR⁴₂, —S(O)R³, —SO₂R³, alkyl, alkenyl, alkynyl, alkylaryl, perhaloalkyl, haloalkyl, aryl, heteroaryl, alkylene-OH, —C(O)R¹¹, —OR¹¹, -alkylene-NR⁴₂, -alkylene-CN, —CN, —C(S)NR⁴₂, —OR², —SR², —N₃, —NO₂, —NHC(S)NR⁴₂, and —NR¹⁸COR²;

L is selected from the group consisting of:

i) a linking group having 2–4 atoms measured by the fewest number of atoms connecting the carbon of the aromatic ring and the phosphorus atom and is selected from the group consisting of -furanyl-, -thienyl-, -pyridyl-, -oxazolyl-, -imidazolyl-, -pyrimidinyl-, and -pyrazinyl-, all of which may be optionally substituted; and ii) a linking group having 3–4 atoms measured by the fewest number of atoms connecting the carbon of the aromatic ring and the phosphorus atom and is optionally substituted -alkoxy;

Y is independently selected from the group consisting of —O—, and —NR⁶—;

when Y is —O—, then R¹ attached to —O— is independently selected from the group consisting of —H, alkyl, optionally substituted aryl, optionally substituted heterocycloalkyl where the cyclic moiety contains a carbonate or thiocarbonate, optionally substituted -alkylaryl, —C(R²)₂OC(O)NR²₂, —NR²—C(O)—R³, —C(R²)₂—OC(O)R³, —C(R²)₂—O—C(O)OR³, —C(R²)₂OC(O)SR³, -alkyl-S—C(O)R³, -alkyl-S—S-alkylhydroxy, and -alkyl-S—S-alkylhydroxy, when one Y is —NR⁶—, and R¹ attached to it is —(CR¹²R¹³)ₙ—C(O)—R¹⁴, then the other Y is selected from the group consisting of —NR¹⁵R¹⁶, —OR⁷, and NR⁶—(CR¹²R¹³)ₙ—C(O)—R¹⁴;

or when either Y is independently selected from —O— and —NR⁶—, then together R¹ and R¹ are -alkyl-S—S-alkyl- to form a cyclic group, or together R¹ and R¹ are

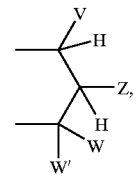

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 ring atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, optionally containing 1 heteroatom, said cyclic group is fused to an aryl group at the beta and gamma position to the Y adjacent to V;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group consisting of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$OR^2$, —$SR^2$, —$CHR^2N_3$, —$CH_2$aryl, —CH(aryl)OH, —CH(CH=$CR^2_2$)OH, —CH(C≡$CR^2$)OH, —$R^2$, —$NR^2_2$, —$OCOR^3$, —$OCO_2R^3$, —$SCOR^3$, —$SCO_2R^3$, —$NHCOR^2$, —$NHCO_2R^3$, —$CH_2$NHaryl, —$(CH_2)_p$—$OR^{19}$, and —$(CH_2)_p$—$SR^{19}$; or p is an integer 2 or 3;

with the provisos that:

a) V, Z, W, W' are not all —H; and b) when Z is —$R^2$, then at least one of V, W, and W' is not —H, alkyl, aralkyl, or alicyclic;

$R^2$ is selected from the group consisting of $R^3$ and —H;

$R^3$ is selected from the group consisting of alkyl, aryl, alicyclic, and aralkyl;

each $R^4$ is independently selected from the group consisting of —H, alkyl, and aryl, or together $R^4$ and $R^4$ are connected via 2–6 atoms, optionally including one heteroatom selected from the group consisting of O, N, and S;

$R^6$ is selected from the group consisting of —H, lower alkyl, acyloxyalkyl, aryl, aralkyl, alkoxycarbonyloxyalkyl, and lower aryl, or together with $R^{12}$ is connected via 1–4 carbon atoms to form a cyclic group;

$R^7$ is lower $R^3$;

each $R^9$ is independently selected from the group consisting of —H, alkyl, aralkyl, and alicyclic, or together $R^9$ and $R^9$ form a cyclic alkyl group;

$R^{11}$ is selected from the group consisting of alkyl, aryl, —$NR^2_2$, and —$OR^2$; and each $R^{12}$ and $R^{13}$ is independently selected from the group consisting of H, lower alkyl, lower aryl, lower aralkyl, all optionally substituted, or $R^{12}$ and $R^{13}$ together are connected via 2–6 carbon atoms to form a cyclic group;

each $R^{14}$ is independently selected from the group consisting of —$OR^{17}$, —$N(R^{17})_2$, —$NHR^{17}$, and —$SR^{17}$;

$R^{15}$ is selected from the group consisting of —H, lower aralkyl, lower aryl, lower aralkyl, or together with $R^{16}$ is connected via 2–6 atoms, optionally including 1 heteroatom selected from the group consisting of O, N, and S;

$R^{16}$ is selected from the group consisting of —$(CR^{12}R^{13})_n$—C(O)—$R^{14}$, lower alkyl, lower aryl, lower aralkyl, or together with $R^{15}$ is connected via 2–6 atoms, optionally including 1 heteroatom selected from the group consisting of O, N, and S;

each $R^{17}$ is independently selected from the group consisting of lower alkyl, lower aryl, and lower aralkyl, or together $R^{17}$ and $R^{17}$ on N is connected via 2–6 atoms, optionally including 1 heteroatom selected from the group consisting of O, N, and S;

$R^{18}$ is lower $R^2$;

$R^{19}$ is selected from the group consisting of —H, and lower acyl;

n is an integer from 1 to 3;

with the provisos that:

1) at least two of $J^2$, $J^3$, $J^4$, $J^5$, and $J^6$ on formula I(b) are not —H or null;

2) if both Y groups are —$NR^6$—, and $R^1$ and $R^1$ are not connected to form a cyclic phosphoramidate, then at least one $R^1$ is —$(CR^{12}R^{13})_n$—C(O)—$R^{14}$;

3) when $R^5$ is phenyl, then $J^3$, $J^4$, and $J^5$ is not purinyl, purinylalkylene, deaza-purinyl, or deazapurinylalkylene;

4) $R^1$ can be selected from the lower alkyl only when the other $YR^1$ is —$NR^6$—$C(R^{12}R^{13})_n$—C(O)—$R^{14}$;

and pharmaceutically acceptable salts thereof.

54. A compound of formula (I):

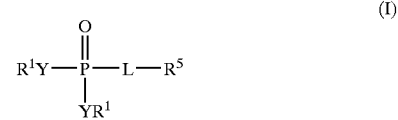

(I)

wherein $R^5$ is

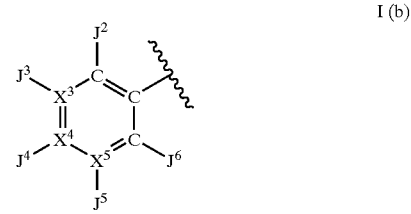

I(b)

wherein:

$X^3$, $X^4$, and $X^5$ are C;

$J^2$, $J^3$, $J^4$, $J^5$, and $J^6$ are independently selected from the group consisting of —$CONR^4_2$, —$CO_2R^3$, halo, —$S(O)_2NR^4_2$, —$S(O)R^3$, —$SO_2R^3$, alkyl, alkenyl, alkynyl, alkylaryl, perhaloalkyl, haloalkyl, aryl, heteroaryl, alkylene-OH, —$C(O)R^{11}$, —$OR^{11}$, -alkylene-$NR^4_2$, -alkylene-CN, —CN, —$C(S)NR^4_2$, —$OR^2$, —$SR^2$, —$N_3$—$NHC(S)NR^4_2$, and —$NR^{18}COR^2$;

L is selected from the group consisting of:

i) a linking group having 2–4 atoms measured by the fewest number of atoms connecting the carbon of the aromatic ring and the phosphorus atom and is selected from the group consisting of -furanyl-, -thienyl-, -pyridyl-, -oxazolyl-, -imidazolyl-, -pyrimidinyl-, -pyrazinyl-, and -alkynyl, all of which may be optionally substituted; and ii) a linking group having 3–4 atoms measured by the fewest number of atoms connecting the carbon of the aromatic ring and the phosphorus atom and is selected from the group consisting of -alkoxycarbonyl-, -alkoxy-, and -alkoxyalkyl-, all of which may be optionally substituted;

Y is independently selected from the group consisting of —O—, and —NR$^6$—;

when Y is —O—, then R$^1$ attached to —O— is independently selected from the group consisting of —H, alkyl, optionally substituted aryl, optionally substituted heterocycloalkyl where the cyclic moiety contains a carbonate or thiocarbonate, optionally substituted -alkylaryl, —C(R$^2$)$_2$OC(O)NR$^2$$_2$, —NR$^2$—C(O)—R$^3$, —C(R$^2$)$_2$—OC(O)R$^3$, —C(R$^2$)$_2$—O—C(O)OR$^3$, —C(R$^2$)$_2$OC(O)SR$^3$, -alkyl-S—C(O)R$^3$, -alkyl-S—S-alkylhydroxy, and -alkyl-S—S—S-alkylhydroxy, when one Y is —NR$^6$—, and R$^1$ attached to it is —(CR$^{12}$R$^{13}$)$_n$—C(O)—R$^{14}$, then the other Y is selected from the group consisting of —NR$^{15}$R$^{16}$, —OR$^7$, and NR$^6$—(CR$^{12}$R$^{13}$)$_n$—C(O)—R$^{14}$;

or when either Y is independently selected from —O— and —NR$^6$—, then together R$^1$ and R$^1$ are -alkyl-S—S-alkyl- to form a cyclic group, or together R$^1$ and R$^1$ are

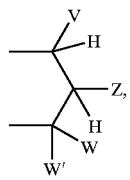

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 ring atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, optionally containing 1 heteroatom, said cyclic group is fused to an aryl group at the beta and gamma position to the Y adjacent to V;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2$$_2$)OH, —CH(C≡CR$^2$)OH, —R$^2$, —NR$^2$$_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^{19}$, and —(CH$_2$)$_p$—SR$^{19}$;

p is an integer 2 or 3;

with the provisos that:

a) V, Z, W, W' are not all —H; and b) when Z is —R$^2$, then at least one of V, W, and W' is not —H, alkyl, aralkyl, or alicyclic;

R$^2$ is selected from the group consisting of R$^3$ and —H;

R$^3$ is selected from the group consisting of alkyl, aryl, alicyclic, and aralkyl;

each R$^4$ is independently selected from the group consisting of —H, alkyl, and aryl, or together R$^4$ and R$^4$ are connected via 2–6 atoms, optionally including one heteroatom selected from the group consisting of O, N, and S;

R$^6$ is selected from the group consisting of —H, lower alkyl, acyloxyalkyl, aryl, aralkyl, alkoxycarbonyloxyalkyl, and lower aryl, or together with R$^{12}$ is connected via 1–4 carbon atoms to form a cyclic group;

R$^7$ is lower R$^3$;

each R$^9$ is independently selected from the group consisting of —H, alkyl, and alicyclic, or together R$^9$ and R$^9$ form a cyclic alkyl group;

R$^{11}$ is selected from the group consisting of alkyl, aryl, —NR$^2$$_2$, and —OR$^2$; and each R$^{12}$ and R$^{13}$ is independently selected from the group consisting of H, lower alkyl, lower aryl, lower aralkyl, all optionally substituted, or R$^{12}$ and R$^{13}$ together are connected via 2–6 carbon atoms to form a cyclic group;

each R$^{14}$ is independently selected from the group consisting of —OR$^{17}$, —N(R$^{17}$)$_2$, —NHR$^{17}$, and —SR$^{17}$;

R$^{15}$ is selected from the group consisting of —H, lower aralkyl, lower aryl, lower aralkyl, or together with R$^{16}$ is connected via 2–6 atoms, optionally including 1 heteroatom selected from the group consisting of O, N, and S;

R$^{16}$ is selected from the group consisting of —(CR$^{12}$R$^{13}$)$_n$—C(O)—R$^{14}$, lower alkyl, lower aryl, lower aralkyl, or together with R$^{15}$ is connected via 2–6 atoms, optionally including 1 heteroatom selected from the group consisting of O, N, and S;

each R$^{17}$ is independently selected from the group consisting of lower alkyl, lower aryl, and lower aralkyl, or together R$^{17}$ and R$^{17}$ on N is connected via 2–6 atoms, optionally including 1 heteroatom selected from the group consisting of O, N, and S;

R$^{18}$ is lower R$^2$;

R$^{19}$ is selected from the group consisting of —H, and lower acyl;

n is an integer from 1 to 3;

with the provisos that:

1) if both Y groups are —NR⁶—, and R¹ and R¹ are not connected form a cyclic phosphoramidate, then at least one R¹ is —(CR¹²R¹³)ₙ—C(O)—R¹⁴;
2) when L is -alkoxyalkyl-, and X³, X⁴, and X⁵ are all C, then neither J³ nor J⁵ can be substituted with an acylated amine;
3) when R⁵ is phenyl, then J³, J⁴, and J⁵ is not purinyl, purinylalkylene, deaza-purinyl, or deazapurinylalkylene;
4) R¹ can be selected from the lower alkyl only when the other YR¹ is —NR⁶—C(R¹²R¹³)ₙ—C(O)—R¹⁴;
5) when R⁵ is phenyl and L is 1,2-ethynyl, then J³ or J⁵ is not a heterocyclic group;
and pharmaceutically acceptable salts thereof.

55. A method of treating complications of diabetes or cardiovascular diseases associated with increased insulin levels in an animal which comprises administering to an animal suffering from complications of diabetes or cardiovascular diseases associated with increased insulin levels a pharmaceutically effective amount of a compound of formula (I):

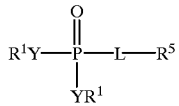

(I)

wherein R⁵ is:

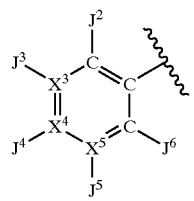

I(b)

wherein:
X³, X⁴, and X⁵ are C;
J², J³, J⁴, J⁵, and J⁶ are independently selected from the group consisting of —H, —NR⁴₂, —CONR⁴₂, —CO₂R³, halo, —S(O)₂NR⁴₂, —S(O)R³, —SO₂R³, alkyl, alkenyl, alkynyl, alkylenearyl, perhaloalkyl, haloalkyl, aryl, heteroaryl, alkylene-OH, —C(O)R¹¹, —OR¹¹, -alkylene-NR⁴₂, -alkylene-CN, —CN, —C(S)NR⁴₂, —OR², —SR², —N₃, —NO₂, —NHC(S)NR⁴₂, and —NR¹⁸COR²;
L is selected from the group consisting of:
i) a linking group having 2–4 atoms measured by the fewest number of atoms connecting the carbon of the aromatic ring and the phosphorus atom and is selected from the group consisting of -furanyl-, -thienyl-, -pyridyl-, -oxazolyl-, -imidazolyl-, -phenyl-, -pyrimidinyl-, -pyrazinyl-, and -alkynyl-, all of which may be optionally substituted; and
ii) a linking group having 3–4 atoms measured by the fewest number of atoms connecting the carbon of the aromatic ring and the phosphorus atom and is selected from the group consisting of -alkylenecarbonylamino-, -alkyleneaminocarbonyl-, -alkyleneoxycarbonyl-, -alkyleneoxy-, -alkylenethio-, -alkylenecarbonyloxy-, -alkylene-S(O)—, -alkylene-S(O)₂—, and -alkyleneoxyalkylene-, all of which may be optionally substituted;

Y is independently selected from the group consisting of —O—, and —NR⁶—;
when Y is —O—, then R¹ attached to —O— is independently selected from the group consisting of —H, alkyl, optionally substituted aryl, optionally substituted heterocyclic alkyl where the cyclic moiety contains a carbonate or thiocarbonate, optionally substituted arylalkylene-, —C(R²)₂OC(O)NR²₂, —NR²—C(O)—R³, —C(R²)₂—OC(O)R³, —C(R²)₂—O—C(O)OR³, —C(R²)₂OC(O)SR³, -alkylene-S—C(O)R³, -alkylene-S—S-alkylenehydroxy, and -alkylene-S—S—S-alkylenehydroxy,
when one Y is —NR⁶—, and R¹ attached to it is —(CR¹²R¹³)ₙ—C(O)—R¹⁴, then the other YR¹ is selected from the group consisting of —NR¹⁵R¹⁶, —OR⁷, and NR⁶—(CR¹²R¹³)ₙ—C(O)—R¹⁴;
or when either Y is independently selected from —O— and —NR⁶—, then together R¹ and R¹ are -alkylene-S—S-alkylene- to form a cyclic group, or together R¹ and R¹ are

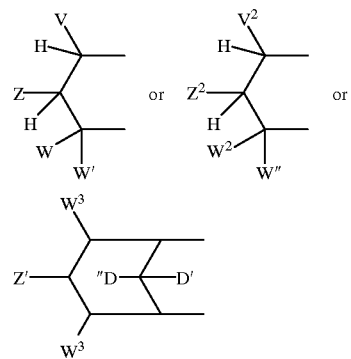

wherein
a) V is selected from the group of aryl, substituted aryl, heteroaryl, substituted heteroaryl, 1-alkynyl and 1-alkenyl;
Z is selected from the group of —CHR²OH, —CHR²OC(O)R³, —CHR²OC(S)R³, —CHR²OC(S)OR³, —CHR²OC(O)SR³, —CHR²OCO₂R³, —OR², —SR², —CHR²N₃, —CH₂aryl, —CH(aryl)OH, —CH(CH=CR²₂)OH, —CH(C≡CR²)OH, —R², —NR²₂, —OCOR³, —OCO₂R³, —SCOR³, —SCO₂R³, —NHCOR², —NHCO₂R³, —CH₂NHaryl, —(CH₂)ₚ—OR¹⁹, and —(CH₂)ₚ—SR¹⁹; or
together V and Z are connected via an additional 3–5 atoms to form a cyclic group, optionally containing 1 heteroatom, said cyclic group is fused to an aryl group at the beta and gamma position to the Y adjacent to V; or
together Z and W are connected via an additional 3–5 atoms to form a cyclic group, optionally containing one heteroatom, and V must be aryl, substituted aryl, heteroaryl, or substituted heteroaryl; or
W and W' are independently selected from the group of —H, alkyl, aralkyl, alicyclic, aryl, substituted aryl, heteroaryl, substituted heteroaryl, 1-alkenyl and 1-alkynyl and —R⁹; or
together W and W' are connected via an additional 2–5 atoms to form a cyclic group, optionally containing 0–2 heteroatoms, and V must be aryl, substituted aryl, heteroaryl, or substituted heteroaryl;
b) V² W² and W" are independently selected from the group of —H, alkyl, aralkyl, alicyclic, aryl, substituted aryl, heteroaryl, substituted heteroaryl, 1-alkenyl, and 1-alkynyl;

$Z^2$ is selected from the group of —$CHR^2OH$, —$CHR^2OC(O)R^3$, —$CHR^2OC(S)R^3$, —$CHR^2OCO_2R^3$, —$CHR^2OC(O)SR^3$, —$CHR^2OC(S)OR^3$, —CH(aryl)OH, —CH(CH=$CR^2_2$)OH, —CH(C≡$CR^2$)OH, —$SR^2$, —$CH_2$NHaryl, —$CH_2$aryl; or together $V^2$ and $Z^2$ are connected via an additional 3–5 atoms to form a cyclic group containing 5–7 ring atoms, optionally containing 1 heteroatom, and substituted with hydroxy, acyloxy, alkyleneoxycarbonyloxy, or aryloxycarbonyloxy attached to a carbon atom that is three atoms from a Y attached to phosphorus;

c) Z' is selected from the group of —OH, —$OC(O)R^3$, —$OCO_2R^3$, and —$OC(O)SR^3$;

$D^-$ is —H;

D" is selected from the group of —H, alkyl, —$OR^2$, —OH, and —$OC(O)R^3$;

each $W^3$ is independently selected from the group consisting of —H, alkyl, aralkyl, alicyclic, aryl, substituted aryl, heteroaryl, substituted heteroaryl, 1-alkenyl, and 1-alkynyl;

p is an integer 2 or 3;

with the provisos that:

a) V, Z, W, W' are not all —H and $V^2$, $Z^2$, $W^2$, W" are not all —H; and $R^2$ is selected from the group consisting of $R^3$ and —H;

$R^3$ is selected from the group consisting of alkyl, aryl, alicyclic, and aralkyl;

each $R^4$ is independently selected from the group consisting of —H, alkylene, -alkylenearyl and aryl, or together $R^4$ and $R^4$ are connected via 2–6 atoms, optionally including one heteroatom selected from the group consisting of O, N, and S;

$R^6$ is selected from the group consisting of —H, lower alkyl, acyloxyalkyl, aryl, aralkyl, alkyloxycarbonyloxyalkyl, and lower acyl, or together with $R^{12}$ is connected via 1–4 carbon atoms to form a cyclic group;

$R^7$ is lower $R^3$;

each $R^9$ is independently selected from the group consisting of —H, alkyl, aralkyl, and alicyclic, or together $R^9$ and $R^9$ form a cyclic alkyl group;

$R^{11}$ is selected from the group consisting of alkyl, aryl, —$NR^2_2$, and —$OR^2$; and each $R^{12}$ and $R^{13}$ is independently selected from the group consisting of H, lower alkyl, lower aryl, lower aralkyl, all optionally substituted, or $R^{12}$ and $R^{13}$ together are connected via a chain of 2–6 atoms, optionally including 1 heteroatom selected from the group consisting of O, N, and S, to form a cyclic group;

each $R^{14}$ is independently selected from the group consisting of —$OR^{17}$, —$N(R^{17})_2$, —$NHR^{17}$, —$SR^{17}$, and —$NR^2OR^{20}$;

$R^{15}$ is selected from the group consisting of —H, lower aralkyl, lower aryl, lower aralkyl, or together with $R^{16}$ is connected via 2–6 atoms, optionally including 1 heteroatom selected from the group consisting of O, N, and S;

$R^{16}$ is selected from the group consisting of —($CR^{12}R^{13})_n$—C(O)—$R^{14}$, —H, lower alkyl, lower aryl, lower aralkyl, or together with $R^{15}$ is connected via 2–6 atoms, optionally including 1 heteroatom selected from the group consisting of O, N, and S;

each $R^{17}$ is independently selected from the group consisting of lower alkyl, lower aryl, and lower aralkyl, or together $R^{17}$ and $R^{17}$ on N is connected via 2–6 atoms, optionally including 1 heteroatom selected from the group consisting of O, N, and S;

$R^{18}$ is selected from the group consisting of —H and lower $R^3$;

$R^{19}$ is selected from the group consisting of —H, and lower acyl;

$R^{20}$ is selected from the group consisting of —H, lower $R^3$, and —C(O)-(lower $R^3$);

n is an integer from 1 to 3;

with the provisos that:

1) if both Y groups are —$NR^6$—, and $R^1$ and $R^1$ are not connected to form a cyclic phosphoramidate, then at least one $R^1$ is —$(CR^{12}R^{13})_n$—C(O)—$R^{14}$;

2) $R^1$ can be selected from the lower alkyl only when the other $YR^1$ is —$NR^6$—$C(R^{12}R^{13})_n$—C(O)—$R^{14}$;

and pharmaceutically acceptable prodrugs and salts thereof.

56. A method of treating diabetes, by administering to patient a pharmaceutically effective amount of an FBPase inhibitor of Formula I:

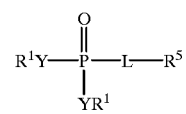

(I)

wherein $R^5$ is:

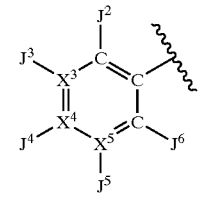

I(b)

wherein:

$X^3$, $X^4$, and $X^5$ are C;

$J^2$, $J^3$, $J^4$, $J^5$, and $J^6$ are independently selected from the group consisting of —H, —$NR^4_2$, —$CONR^4_2$, —$CO_2R^3$, halo, —$S(O)_2NR^4_2$, —$S(O)R^3$, —$SO_2R^3$, alkyl, alkenyl, alkynyl, alkylenearyl, perhaloalkyl, haloalkyl, aryl, heteroaryl, alkylene-OH, —$C(O)R^{11}$, —$OR^{11}$, -alkylene-$NR^4_2$, -alkylene-CN, —CN, —C(S)$NR^4_2$, —$OR^2$, —$SR^2$, —$N_3$, —$NO_2$, —$NHC(S)NR^4_2$, and —$NR^{18}COR^2$;

L is selected from the group consisting of:

i) a linking group having 2–4 atoms measured by the fewest number of atoms connecting the carbon of the aromatic ring and the phosphorus atom and is selected from the group consisting of -furanyl-, -thienyl-, -pyridyl-, -oxazolyl-, -imidazolyl-, -phenyl-, -pyrimidinyl-, -pyrazinyl-, and -alkynyl-, all of which may be optionally substituted; and ii) a linking group having 3–4 atoms measured by the fewest number of atoms connecting the carbon of the aromatic ring and the phosphorus atom and is selected from the group consisting of -alkylenecarbonylamino-, -alkyleneaminocarbonyl-, -alkyleneoxycarbonyl-, -alkyleneoxy-, -alkylenethio-, -alkylenecarbonyloxy-, -alkylene-S(O)—, -alkylene-S(O)_2—, and -alkyleneoxyalkylene-, all of which may be optionally substituted;

Y is independently selected from the group consisting of —O—, and —NR$^6$—;

when Y is —O—, then R$^1$ attached to —O— is independently selected from the group consisting of —H, alkyl, optionally substituted aryl, optionally substituted heterocyclic alkyl where the cyclic moiety contains a carbonate or thiocarbonate, optionally substituted arylalkylene-, —C(R$^2$)$_2$OC(O)NR$^2$$_2$, —NR$^2$—C(O)—R$^3$, —C(R$^2$)$_2$—OC(O)R$^3$, —C(R$^2$)$_2$—O—C(O)OR$^3$, —C(R$^2$)$_2$OC(O)SR$^3$, -alkylene-S—C(O)R$^3$, -alkylene-S—S-alkylenehydroxy, and -alkylene-S—S—S-alkylenehydroxy, when one Y is —NR$^6$—, and R$^1$ attached to it is —(CR$^{12}$R$^{13}$)$_n$—C(O)—R$^{14}$, then the other YR$^1$ is selected from the group consisting of —NR$^{15}$R$^{16}$, —OR$^7$, and NR$^6$—(CR$^{12}$R$^{13}$)$_n$—C(O)—R$^{14}$;

or when either Y is independently selected from —O— and —NR$^6$—, then together R$^1$ and R$^1$ are -alkylene-S—S-alkylene- to form a cyclic group, or together R$^1$ and R$^1$ are

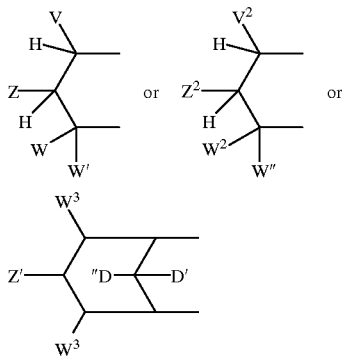

wherein
a) V is selected from the group of aryl, substituted aryl, heteroaryl, substituted heteroaryl, 1-alkynyl and 1-alkenyl;

Z is selected from the group of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2$$_2$)OH, —CH(C≡CR$^2$)OH, —R$^2$, —NR$^2$$_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^{19}$, and —(CH$_2$)$_p$—SR$^{19}$; or together V and Z are connected via an additional 3–5 atoms to form a cyclic group, optionally containing 1 heteroatom, said cyclic group is fused to an aryl group at the beta and gamma position to the Y adjacent to V; or together Z and W are connected via an additional 3–5 atoms to form a cyclic group, optionally containing one heteroatom, and V must be aryl, substituted aryl, heteroaryl, or substituted heteroaryl; or W and W' are independently selected from the group of —H, alkyl, aralkyl, alicyclic, aryl, substituted aryl, heteroaryl, substituted heteroaryl, 1-alkenyl and 1-alkynyl and —R$^9$; or together W and W' are connected via an additional 2–5 atoms to form a cyclic group, optionally containing 0–2 heteroatoms, and V must be aryl, substituted aryl, heteroaryl, or substituted heteroaryl;

b) V$^2$, W$^2$ and W" are independently selected from the group of —H, alkyl, aralkyl, alicyclic, aryl, substituted aryl, heteroaryl, substituted heteroaryl, 1-alkenyl, and 1-alkynyl;

Z$^2$ is selected from the group of —CHR$^2$OH, —CHR$^2$OC(O)R$^3$, —CHR$^2$OC(S)R$^3$, —CHR$^2$OCO$_2$R$^3$, —CHR$^2$OC(O)SR$^3$, —CHR$^2$OC(S)OR$^3$, —CH(aryl)OH, —CH(CH=CR$^2$$_2$)OH, —CH(C≡CR$^2$)OH, —SR$^2$, —CH$_2$NHaryl, —CH$_2$aryl; or together V$^2$ and Z$^2$ are connected via an additional 3–5 atoms to form a cyclic group containing 5–7 ring atoms, optionally containing 1 heteroatom, and substituted with hydroxy, acyloxy, alkyleneoxycarbonyloxy, or aryloxycarbonyloxy attached to a carbon atom that is three atoms from a Y attached to phosphorus;

c) Z' is selected from the group of —OH, —OC(O)R$^3$, —OCO$_2$R$^3$, and —OC(O)SR$^3$;

D' is —H;

D" is selected from the group of —H, alkyl, —OR$^2$, —OH, and —OC(O)R$^3$;

each W$^3$ is independently selected from the group consisting of —H, alkyl, aralkyl, alicyclic, aryl, substituted aryl, heteroaryl, substituted heteroaryl, 1-alkenyl, and 1-alkynyl;

p is an integer 2 or 3;

with the provisos that:

a) V, Z, W, W' are not all —H and V$^2$, Z, W$^2$, W" are not all —H; and

R$^2$ is selected from the group consisting of R$^3$ and —H;

R$^3$ is selected from the group consisting of alkyl, aryl, alicyclic, and aralkyl;

each R$^4$ is independently selected from the group consisting of —H, alkylene, -alkylenearyl and aryl, or together R$^4$ and R$^4$ are connected via 2–6 atoms, optionally including one heteroatom selected from the group consisting of O, N, and S;

R$^6$ is selected from the group consisting of —H, lower alkyl, acyloxyalkyl, aryl, aralkyl, alkyloxycarbonyloxyalkyl, and lower acyl, or together with R$^{12}$ is connected via 1–4 carbon atoms to form a cyclic group;

R$^7$ is lower R$^3$;

each R$^9$ is independently selected from the group consisting of —H, alkyl, aralkyl, and alicyclic, or together R$^9$ and R$^9$ form a cyclic alkyl group;

R$^{11}$ is selected from the group consisting of alkyl, aryl, —NR$^2$, and —OR$^2$; and each R$^{12}$ and R$^{13}$ is independently selected from the group consisting of H, lower alkyl, lower aryl, lower aralkyl, all optionally substituted, or R$^{12}$ and R$^{13}$ together are connected via a chain of 2–6 atoms, optionally including 1 heteroatom selected from the group consisting of O, N, and S, to form a cyclic group;

each R$^{14}$ is independently selected from the group consisting of —OR$^{17}$, —N(R$^{17}$)$_2$, —NHR$^{17}$, —SR$^{17}$, and —NR$^2$OR$^{20}$;

R$^{15}$ is selected from the group consisting of —H, lower aralkyl, lower aryl, lower aralkyl, or together with R$^{16}$ is connected via 2–6 atoms, optionally including 1 heteroatom selected from the group consisting of O, N, and S;

R$^{16}$ is selected from the group consisting of —(CR$^{12}$R$^{13}$)$_n$—C(O)—R$^{14}$, —H, lower alkyl, lower aryl, lower aralkyl, or together with $R^{15}$ is connected via 2–6 atoms, optionally including 1 heteroatom selected from the group consisting of O, N, and S;

each $R^{17}$ is independently selected from the group consisting of lower alkyl, lower aryl, and lower aralkyl, or together $R^{17}$ and $R^{17}$ on N is connected via 2–6 atoms, optionally including 1 heteroatom selected from the group consisting of O, N, and S;

$R^{18}$ is selected from the group consisting of —H and lower $R^3$;

$R^{19}$ is selected from the group consisting of —H, and lower acyl;

$R^{20}$ is selected from the group consisting of —H, lower $R^3$, and —C(O)-(lower $R^3$);

n is an integer from 1 to 3;

with the provisos that:
1) if both Y groups are —$NR^6$—, and $R^1$ and $R^1$ are not connected to form a cyclic phosphoramidate, then at least one $R^1$ is —$(CR^{12}R^{13})_n$—C(O)—$R^{14}$;
2) $R^1$ can be selected from the lower alkyl only when the other $YR^1$ is —$NR^6$—$C(R^{12}R^{13})_n$—C(O)—$R^{14}$;

and pharmaceutically acceptable prodrugs and salts thereof.

* * * * *